US007541039B2

(12) United States Patent
Leenhouts et al.

(10) Patent No.: US 7,541,039 B2
(45) Date of Patent: *Jun. 2, 2009

(54) IMMUNIZATION WITH BACTERIAL GHOST-BASED VACCINES

(75) Inventors: Cornelis Johannes Leenhouts, Haren (NL); Ranjan Ramasamy, Colombo (LK); Anton Steen, Groningen (NL); Jan Kok, Groningen (NL); Girbe Buist, Sappemeer (NL); Oscar Paul Kuipers, Groningen (NL)

(73) Assignee: Applied NanoSystems, B.V., Groningen (NL)

( * ) Notice: Subject to any disclaimer, the term of this patent is extended or adjusted under 35 U.S.C. 154(b) by 422 days.

This patent is subject to a terminal disclaimer.

(21) Appl. No.: 11/299,304

(22) Filed: Dec. 9, 2005

(65) Prior Publication Data

US 2006/0115491 A1 Jun. 1, 2006

Related U.S. Application Data

(60) Division of application No. 10/321,857, filed on Dec. 16, 2002, now Pat. No. 7,067,639, which is a continuation of application No. PCT/NL02/00383, filed on Jun. 11, 2002.

(30) Foreign Application Priority Data

Jun. 11, 2001 (EP) ................... 01202239

(51) Int. Cl.
*A61K 39/02* (2006.01)
*A61K 39/00* (2006.01)
*A61K 39/002* (2006.01)
*A61K 39/385* (2006.01)
*A61K 39/116* (2006.01)
*A61K 39/09* (2006.01)
*A61K 45/00* (2006.01)
*A61K 39/07* (2006.01)
*A61K 39/04* (2006.01)
*A61K 39/015* (2006.01)
*C12N 1/00* (2006.01)
*C12N 1/06* (2006.01)

(52) U.S. Cl. .............. 424/234.1; 424/193.1; 424/190.1; 424/191.1; 424/203.1; 424/244.1; 424/266.1; 424/265.1; 424/279.1; 424/278.1; 424/282.1; 424/246.1; 424/248.1; 424/268.1; 424/272.1; 435/259; 435/243

(58) Field of Classification Search ........................ None
See application file for complete search history.

(56) References Cited

U.S. PATENT DOCUMENTS

| 5,470,573 | A | 11/1995 | Lubitz et al. |
| 5,616,686 | A | 4/1997 | Fischetti et al. |
| 5,786,205 | A | 7/1998 | Fischetti et al. |
| 5,821,088 | A | 10/1998 | Darzins et al. |
| 5,955,258 | A | 9/1999 | Buist et al. |
| 6,027,910 | A | 2/2000 | Klis et al. |
| 6,114,147 | A | 9/2000 | Frenken et al. |
| 6,177,083 | B1 | 1/2001 | Lubitz |
| 6,423,316 | B1 | 7/2002 | Riesbeck et al. |
| 6,827,940 | B1 | 12/2004 | Riordan et al. |
| 6,896,887 | B2 | 5/2005 | Leenhouts et al. |
| 7,067,639 | B2 * | 6/2006 | Leenhouts et al. .......... 530/412 |
| 2003/0180816 | A1 * | 9/2003 | Leenhouts et al. ......... 435/7.22 |
| 2003/0186851 | A1 | 10/2003 | Leenhouts et al. |
| 2006/0115491 | A1 * | 6/2006 | Leenhouts et al. ....... 424/190.1 |
| 2008/0193427 | A1 * | 8/2008 | Kaesler et al. ........... 424/93.45 |

FOREIGN PATENT DOCUMENTS

| DE | 3919644 A1 | 12/1990 |
| DE | 198 00 746 A1 | 7/1999 |
| EP | 0 545 352 A1 | 6/1993 |
| EP | 0 712 935 A2 | 5/1996 |
| JP | 02065790 A | 3/1990 |
| JP | 10117783 A | 5/1998 |
| JP | 2002017357 A | 1/2002 |
| WO | WO 91/13155 | 9/1991 |
| WO | WO 92/01791 | 2/1992 |
| WO | WO 94/01567 | 1/1994 |
| WO | WO 94/18330 | 8/1994 |
| WO | WO 95/31561 | 11/1995 |
| WO | WO 96/00579 | 1/1996 |
| WO | WO 96/11263 | 4/1996 |
| WO | WO 96/40943 | 12/1996 |
| WO | WO 97/28263 | 8/1997 |
| WO | WO 98/07874 | 2/1998 |
| WO | WO 98/42850 | 10/1998 |
| WO | WO 99/25836 | 5/1999 |
| WO | WO 00/44878 | 8/2000 |
| WO | WO 00/53163 | 9/2000 |
| WO | WO 01-09350 A2 | 2/2001 |
| WO | WO 01/54672 A2 | 8/2001 |
| WO | WO 01/91791 A2 | 12/2001 |
| WO | WO 02/101026 A2 | 12/2002 |

OTHER PUBLICATIONS

Ramasamy et al, Vaccine, 2006, 24:3900-3908.*
Jalava et al, Expert Review of Vaccine, Feb. 2003, 2/1:45-51 (abstract only).*
Moorthy et al, Vaccine, 2007, 25:3636-3645.*

(Continued)

*Primary Examiner*—N. M Minnifield
(74) *Attorney, Agent, or Firm*—TraskBritt

(57) ABSTRACT

Methods for improving binding of a proteinaceous substance to cell-wall material of a Gram-positive bacterium are disclosed. The proteinaceous substance includes an AcmA cell-wall binding domain, homolog or functional derivative thereof. The method includes treating the cell-wall material with a solution capable of removing a cell-wall component such as a protein, lipoteichoic acid or carbohydrate from the cell-wall material and contacting the proteinaceous substance with the cell-wall material.

14 Claims, 21 Drawing Sheets

OTHER PUBLICATIONS

Bolotin et al., The Complete Genome Sequence of the Lactic Acid Bacterium *Lactococcus lactis* ssp. lactis IL 1403, Genome Research, 2001, pp. 731-753, vol. 11.

Brown et al., Comparison of Various Procedures for Removing Proteins and Nucleic Acids from Cell Walls of *Bacillus subtilis*, 1976, pp. 479-488.

Buist et al., Molecular Cloning and Nucleotide Sequence of the Gene Encoding the Major Peptidoglycan Hydrolase of *Lactococcus lactis*, a Muramidase Needed for Cell Separation, Journal of Bacteriology, Mar. 1995, pp. 155463, vol. 177, No. 6.

CIBIK et al., Identification of Mur, an Atypical Peptidoglycan Hydrolase Derived from *Leuconostoc citreum*, Applied And Environmental Microbiology, Feb. 2001, pp. 85864, vol. 67, No. 2.

Fischetti et al., 1996, Gram-positive commensal bacteria for mucosal vaccine delivery. Current Opinions in Biotechnology v7:659-666.

Furst-Ladani et al., Vaccine, 2000, 18:440-448.

Gasson et al., Plasmid Complements of *Streptococcus lactis* NCDO 712 and OtherLactic *Streptococci* After Protoplast-Induced Curing, Journal of Bacteriology, Apr. 1983, pp. 1-9, vol. 154, No. 1.

Haslberger et al., J. Biotechnology, 2000, 83:57-66.

Hatfaludi et al., J. Agric. Food Chem., 2004, 52:5627-5634.

Huter et al., J. Controlled Release, 1999, 61:51-63.

Jalava et al., J. Controlled Release, 2002, 85:17-25.

Kok et al., Nucleotide Sequence of the Cell Wall Proteinase Gene of *Streptococcus cremoris* Wg2, Applied and Environmental Microbiology, Jan. 1988, p. 231-238, vol. 54, No. 1.

Kuipers et al., Controlled overproduction of proteins by lactic acid bacteria, Trends in Biotechnology, Apr. 1997, pp. 135-140, vol. 15.

European Search Report, EP 01 20 2239, dated Jan. 14, 2002.

Marchart et al., Vaccine, 2003, 21:1415-22.

Medaglini et al., Mucosal and systemic immune responses to a recombinant protein expressed on the surface of the oral commensal bacterium *Streptococcus gordonii* after oral colonization, Proc. Natl. Acad. Sci.,Jul. 1995, pp. 6868-72, vol. 92.

Morata et al., Study of the Morphology of the Cell Walls of Some Strains of Lactic Acid Bacteria and Related Species, Journal of Food Protection, 1998, pp. 557-562, vol. 61, No. 5.

Navarre et al., Proteolytic cleavage and cell wall anchoring at the LPXTG motif of surface proteins in Grampositive bacteria, Molecular Microbiology, 1994, pp. 115-121, vol. 14, No. 1.

Norton et al., Factors affecting the immunogenicityof tetanus toxin fragment C expressed in *Lactococcus lactis*, FEMS Immunology and Medical Microbiology, 1996, pp. 167-177, vol. 14.

Norton et al., The immune response to *Lactococcus lactis*: Implications for its use as avaccine delivery vehicle, Federation of European Microbiological Societies, 1994, pp. 249-256, vol. 120.

Paukner et al., J. Controlled Release, 2004, 94:63-74.

Paukner et al., J. Drug Targeting, Apr. 2003, 11/3:151-61.

Poquet et al., HtrA is the unique surface housekeeping protease in *Lactococcus lactis* and is required for natural protein processing, Molecular Microbiology, 2000, p. 1042-1051, vol. 35, No. 5.

Pozzi et al., 1992, Delivery and expression of a heterologous antigen on the surface of *Streptococci*, Infection and Immunity, v60(5):1902-07.

Ramasamy et al., Antibodies to a merozoite surface protein promote multiple invasion of red blood cells by malaria parasites, Parasite Immunology, 1999, pp. 397-407, vol. 21.

Ramasamy et al., Studies on glycoproteins in the human malaria parasite Plasmodiunfalciparum. Identification of a myristilated 45kDa merozoite membrane glycoprotein, Immunol. Cell Biol., 1987, pp. 419-424, vol. 65, Pt. 5.

Robinson et al., Oral vaccination of mice against tetanus with recombinan *Lactococcus lactis*, Nature Biotechnology, Jul. 1997, pp. 653-657, vol. 15.

Sauve et al., Concentration of Dilute Protein for Gel Electrophoresis, Analytical Biochemistry, 1995, pp. 382-383, vol. 226.

Stahl et al., Bacterial surface display: trends and progress, Trends in Biotechnology, pp. 185-192, vol. 15.

Szostak et al., J. Biotechnology, 1996, 44, 161-170.

\* cited by examiner

A
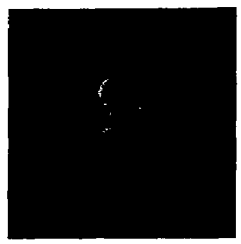  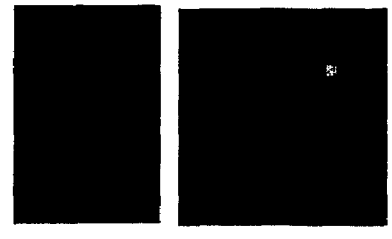
*Lb. curvatus* NCFB2739  *Lb. sake* NCFB2714  *L. lactis*
B
*L. lactis* TCA pretreated
Fig. 2

```
AcmA(A1)   YTVKSGDTLWGISQRYGISVAQIQSANN-LKSTI-IYIGQKLVLT    (SEQ ID NO:16)
AcmD(D1)   YKVQEGDSLSAIAAQYGTTVDALVSANS-LENANDIHVGEVLQVA    (SEQ ID NO:19)
              *      **    **  *  *        *      *

AcmA(A2)   VKVKSGDTLWALSVKYKTSIAQLKSWNH-LSSDT-IYIGQNLIVS    (SEQ ID NO:17)
AcmD(D2)   YTVKSGDSLYSIAEQYGMTVSSLMSANGIYDVNSMLQVGQVLQVTV   (SEQ ID NO:20)
           ****  *   *   *  **             *    *   *

AcmA(A3)   HKVVKGDTLWGLSQKSGSPIASIKAWN-HLSSDT-ILIGQYLRIK    (SEQ ID NO:18)
AcmD(D3)   YTIQNGDSIYSIATANGMTADQLAALNGFGINDM-IHPGQTIRI     (SEQ ID NO:21)
              * ***  *  *                      *    **

Consensus  YxVKxGDTLxxIAxxxxxxxxxxLxxxNxxLxxxxxIxxGQxIxVx   (SEQ ID NO:163)
repeat     H  IR   ESV  LS           I      I   L   LI    (SEQ ID NO:164)
           L   I    V                              V L    (SEQ ID NO:165)
```

Fig. 6

TCA-pretreated *L. lactis* loaded with:
MSA2::cA
MSA2::cD
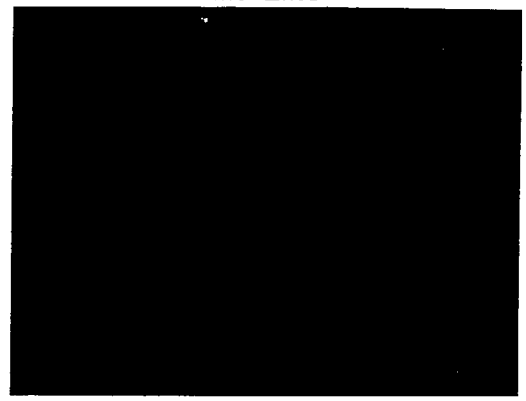
Fig. 8

Effect of TCA pretreatment on *L. lactis* and binding of MSA2::cA

*Lb. casei* ATCC393
 
Non-TCA pretreated   TCA pretreated
Fig. 11

Binding to TCA pretreated *Mycobacterium smegmatis*

MSA2::cA

MSA2::cD

Fig. 12

A. 
B. 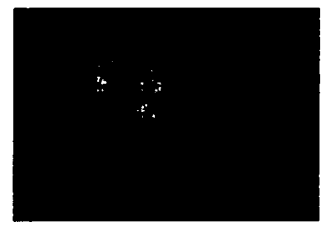
C. 
Fig. 14

SEQUENCE LISTING

```
<160> NUMBER OF SEQ ID NOS: 165

<210> SEQ ID NO 1
<211> LENGTH: 5
<212> TYPE: PRT
<213> ORGANISM: Artificial Sequence
<220> FEATURE:
<221> NAME/KEY: SITE
<222> LOCATION: (1)..(5)
<223> OTHER INFORMATION: motif, anchoring portion, "Xaa" can be any
      amino acid

<400> SEQUENCE: 1

Leu Pro Xaa Thr Gly
 1               5

<210> SEQ ID NO 2
<211> LENGTH: 30
<212> TYPE: DNA
<213> ORGANISM: Artificial Sequence
<220> FEATURE:
<223> OTHER INFORMATION: synthesized sequence, primer MSA2.1

<400> SEQUENCE: 2
```
accatggcaa aaaatgaaag taaatatagc         30

<210> SEQ ID NO 3
<211> LENGTH: 48
<212> TYPE: DNA
<213> ORGANISM: Artificial Sequence
<220> FEATURE:
<223> OTHER INFORMATION: synthesized sequence, primer MSA2.4

<400> SEQUENCE: 3
cggtctctag cttataagct tagaattcgg gatgttgctg ctccacag         48

<210> SEQ ID NO 4
<211> LENGTH: 32
<212> TYPE: DNA
<213> ORGANISM: Artificial Sequence
<220> FEATURE:
<223> OTHER INFORMATION: synthesized sequence, primer PrtP.sspro.fw

<400> SEQUENCE: 4
ccgtctccca tgcaaaggaa aaagaaagg gc         32

<210> SEQ ID NO 5
<211> LENGTH: 46
<212> TYPE: DNA
<213> ORGANISM: Artificial Sequence
<220> FEATURE:
<223> OTHER INFORMATION: synthesized sequence, primer PrtP.sspro.rev

<400> SEQUENCE: 5
aaaaaaagct tgaattccca tggcagtcgg ataataaact ttcgcc         46

<210> SEQ ID NO 6
<211> LENGTH: 44
<212> TYPE: DNA
<213> ORGANISM: Artificial Sequence
<220> FEATURE:
<223> OTHER INFORMATION: synthesized sequence, primer pACMB2

<400> SEQUENCE: 6
cgcaagcttc tgcagagctc ttagattcta attgtttgtc ctgg         44

<210> SEQ ID NO 7
<211> LENGTH: 30
<212> TYPE: DNA
<213> ORGANISM: Artificial Sequence
<220> FEATURE:
<223> OTHER INFORMATION: synthesized sequence, primer pACMB3

<400> SEQUENCE: 7
cggaattcaa ggaggagaaa tatcaggagg         30

<210> SEQ ID NO 8
<211> LENGTH: 31
<212> TYPE: DNA
<213> ORGANISM: Artificial Sequence
<220> FEATURE:
<223> OTHER INFORMATION: synthesized sequence, primer PrtP.cwa.fw3

<400> SEQUENCE: 8
atataaagct tgcaaagtct gaaaacgaag g         31

<210> SEQ ID NO 9
<211> LENGTH: 35
<212> TYPE: DNA
<213> ORGANISM: Artificial Sequence

```
<220> FEATURE:
<223> OTHER INFORMATION: synthesized sequence, primer PrtP.cwa.rev

<400> SEQUENCE: 9
ccgtctcaag ctcactattc ttcacgttgt ttccg                               35

<210> SEQ ID NO 10
<211> LENGTH: 35
<212> TYPE: DNA
<213> ORGANISM: Artificial Sequence
<220> FEATURE:
<223> OTHER INFORMATION: synthesized sequence, primer cArepeat3.fw

<400> SEQUENCE: 10
ccgtctccaa ttcaatctgc tgctgcttca aatcc                               35

<210> SEQ ID NO 11
<211> LENGTH: 58
<212> TYPE: DNA
<213> ORGANISM: Artificial Sequence
<220> FEATURE:
<223> OTHER INFORMATION: synthesized sequence, primer cArepeat3.rev

<400> SEQUENCE: 11
taataagctt aaaggtctcc aattcctttt attcgtagat actgaccaat taaaatag     58

<210> SEQ ID NO 12
<211> LENGTH: 38
<212> TYPE: DNA
<213> ORGANISM: Artificial Sequence
<220> FEATURE:
<223> OTHER INFORMATION: synthesized sequence, primer cDrepeat1.fw

<400> SEQUENCE: 12
ccgtctccaa tttcaggagg aactgctgtt acaactag                            38

<210> SEQ ID NO 13
<211> LENGTH: 50
<212> TYPE: DNA
<213> ORGANISM: Artificial Sequence
<220> FEATURE:
<223> OTHER INFORMATION: synthesized sequence, primer cDrepeat3.rev

<400> SEQUENCE: 13
taataagctt aaaggtctcc aattccagca acttgcaaaa cttctcctac               50

<210> SEQ ID NO 14
<211> LENGTH: 37
<212> TYPE: DNA
<213> ORGANISM: Artificial Sequence
<220> FEATURE:
<223> OTHER INFORMATION: synthesized sequence, primer ppmA.1

<400> SEQUENCE: 14
cggtctcaca tgtcgaaagg gtcagaaggt gcagacc                             37

<210> SEQ ID NO 15
<211> LENGTH: 39
<212> TYPE: DNA
<213> ORGANISM: Artificial Sequence
<220> FEATURE:
<223> OTHER INFORMATION: synthesized sequence, primer ppmA.2

<400> SEQUENCE: 15
cggtctcgaa ttgcttcgtt tgatgtacta ctgcttgag                           39
```

```
<210> SEQ ID NO 16
<211> LENGTH: 43
<212> TYPE: PRT
<213> ORGANISM: Lactococcus lactis
<220> FEATURE:
<221> NAME/KEY: SITE
<222> LOCATION: (1)..(43)
<223> OTHER INFORMATION: AcmA cell wall binding domain homologue

<400> SEQUENCE: 16

Tyr Thr Val Lys Ser Gly Asp Thr Leu Trp Gly Ile Ser Gln Arg Tyr
 1               5                  10                  15

Gly Ile Ser Val Ala Gln Ile Gln Ser Ala Asn Asn Leu Lys Ser Thr
                20                  25                  30

Ile Ile Tyr Ile Gly Gln Lys Leu Val Leu Thr
            35                  40

<210> SEQ ID NO 17
<211> LENGTH: 43
<212> TYPE: PRT
<213> ORGANISM: Lactococcus lactis
<220> FEATURE:
<221> NAME/KEY: SITE
<222> LOCATION: (1)..(43)
<223> OTHER INFORMATION: AcmA cell wall binding domain homologue

<400> SEQUENCE: 17

Val Lys Val Lys Ser Gly Asp Thr Leu Trp Ala Leu Ser Val Lys Tyr
 1               5                  10                  15

Lys Thr Ser Ile Ala Gln Leu Lys Ser Trp Asn His Leu Ser Ser Asp
                20                  25                  30

Thr Ile Tyr Ile Gly Gln Asn Leu Ile Val Ser
            35                  40

<210> SEQ ID NO 18
<211> LENGTH: 43
<212> TYPE: PRT
<213> ORGANISM: Lactococcus lactis
<220> FEATURE:
<221> NAME/KEY: SITE
<222> LOCATION: (1)..(43)
<223> OTHER INFORMATION: AcmA cell wall binding domain homologue

<400> SEQUENCE: 18

His Lys Val Val Lys Gly Asp Thr Leu Trp Gly Leu Ser Gln Lys Ser
 1               5                  10                  15

Gly Ser Pro Ile Ala Ser Ile Lys Ala Trp Asn His Leu Ser Ser Asp
                20                  25                  30

Thr Ile Leu Ile Gly Gln Tyr Leu Arg Ile Lys
            35                  40

<210> SEQ ID NO 19
<211> LENGTH: 44
<212> TYPE: PRT
<213> ORGANISM: Lactococcus lactis
<220> FEATURE:
<221> NAME/KEY: SITE
<222> LOCATION: (1)..(44)
<223> OTHER INFORMATION: AcmA cell wall binding domain homologue

<400> SEQUENCE: 19

Tyr Lys Val Gln Glu Gly Asp Ser Leu Ser Ala Ile Ala Ala Gln Tyr
 1               5                  10                  15

Gly Thr Thr Val Asp Ala Leu Val Ser Ala Asn Ser Leu Glu Asn Ala
```

-continued

```
                20                  25                  30

Asn Asp Ile His Val Gly Glu Val Leu Gln Val Ala
        35                  40

<210> SEQ ID NO 20
<211> LENGTH: 46
<212> TYPE: PRT
<213> ORGANISM: Lactococcus lactis
<220> FEATURE:
<221> NAME/KEY: SITE
<222> LOCATION: (1)..(46)
<223> OTHER INFORMATION: AcmA cell wall binding domain homologue

<400> SEQUENCE: 20

Tyr Thr Val Lys Ser Gly Asp Ser Leu Tyr Ser Ile Ala Glu Gln Tyr
  1               5                  10                  15

Gly Met Thr Val Ser Ser Leu Met Ser Ala Asn Gly Ile Tyr Asp Val
                 20                  25                  30

Asn Ser Met Leu Gln Val Gly Gln Val Leu Gln Val Thr Val
        35                  40                  45

<210> SEQ ID NO 21
<211> LENGTH: 43
<212> TYPE: PRT
<213> ORGANISM: Lactococcus lactis
<220> FEATURE:
<221> NAME/KEY: SITE
<222> LOCATION: (1)..(43)
<223> OTHER INFORMATION: AcmA cell wall binding domain homologue

<400> SEQUENCE: 21

Tyr Thr Ile Gln Asn Gly Asp Ser Ile Tyr Ser Ile Ala Thr Ala Asn
  1               5                  10                  15

Gly Met Thr Ala Asp Gln Leu Ala Ala Leu Asn Gly Phe Gly Ile Asn
                 20                  25                  30

Asp Met Ile His Pro Gly Gln Thr Ile Arg Ile
        35                  40

<210> SEQ ID NO 22
<211> LENGTH: 44
<212> TYPE: PRT
<213> ORGANISM: Lactococcus bacteriophage Tuc2009
<220> FEATURE:
<221> NAME/KEY: SITE
<222> LOCATION: (1)..(44)
<223> OTHER INFORMATION: AcmA cell wall binding domain homologue

<400> SEQUENCE: 22

Tyr Val Val Lys Gln Gly Asp Thr Leu Ser Gly Ile Ala Ser Asn Trp
  1               5                  10                  15

Gly Thr Asn Trp Gln Glu Leu Ala Arg Gln Asn Ser Leu Ser Asn Pro
                 20                  25                  30

Asn Met Ile Tyr Ala Gly Gln Val Ile Ser Phe Thr
        35                  40

<210> SEQ ID NO 23
<211> LENGTH: 43
<212> TYPE: PRT
<213> ORGANISM: Lactococcus bacteriophage Tuc2009
<220> FEATURE:
<221> NAME/KEY: SITE
<222> LOCATION: (1)..(43)
<223> OTHER INFORMATION: AcmA cell wall binding domain homologue

<400> SEQUENCE: 23
```

```
Tyr Thr Val Gln Ser Gly Asp Asn Leu Ser Ser Ile Ala Ile Leu Leu
 1               5                  10                  15

Gly Thr Thr Val Gln Ser Leu Val Ser Met Asn Gly Ile Ser Asn Pro
            20                  25                  30

Asn Leu Ile Tyr Ala Gly Gln Thr Leu Asn Tyr
        35                  40
```

<210> SEQ ID NO 24
<211> LENGTH: 44
<212> TYPE: PRT
<213> ORGANISM: Lactococcus bacteriophage LC3
<220> FEATURE:
<221> NAME/KEY: SITE
<222> LOCATION: (1)..(44)
<223> OTHER INFORMATION: AcmA cell wall binding domain homologue

<400> SEQUENCE: 24

```
Tyr Ile Val Lys Gln Gly Asp Thr Leu Ser Gly Ile Ala Ser Asn Leu
 1               5                  10                  15

Gly Thr Asn Trp Gln Glu Leu Ala Arg Gln Asn Ser Leu Ser Asn Pro
            20                  25                  30

Asn Met Ile Tyr Ser Gly Gln Val Ile Ser Leu Thr
        35                  40
```

<210> SEQ ID NO 25
<211> LENGTH: 43
<212> TYPE: PRT
<213> ORGANISM: Lactococcus bacteriophage LC3
<220> FEATURE:
<221> NAME/KEY: SITE
<222> LOCATION: (1)..(43)
<223> OTHER INFORMATION: AcmA cell wall binding domain homologue

<400> SEQUENCE: 25

```
Tyr Thr Val Gln Ser Gly Asp Asn Leu Ser Ser Ile Ala Arg Arg Leu
 1               5                  10                  15

Gly Thr Thr Val Gln Ser Leu Val Ser Met Asn Gly Ile Ser Asn Pro
            20                  25                  30

Asn Leu Ile Tyr Ala Gly Gln Thr Leu Asn Tyr
        35                  40
```

<210> SEQ ID NO 26
<211> LENGTH: 43
<212> TYPE: PRT
<213> ORGANISM: Enterococcus faecalis
<220> FEATURE:
<221> NAME/KEY: SITE
<222> LOCATION: (1)..(43)
<223> OTHER INFORMATION: AcmA cell wall binding domain homologue

<400> SEQUENCE: 26

```
Tyr Thr Val Lys Ser Gly Asp Thr Leu Asn Lys Ile Ala Ala Gln Tyr
 1               5                  10                  15

Gly Val Ser Val Ala Asn Leu Arg Ser Trp Asn Gly Ile Ser Gly Asp
            20                  25                  30

Leu Ile Phe Val Gly Gln Lys Leu Ile Val Lys
        35                  40
```

<210> SEQ ID NO 27
<211> LENGTH: 43
<212> TYPE: PRT
<213> ORGANISM: Enterococcus faecalis
<220> FEATURE:

```
<221> NAME/KEY: SITE
<222> LOCATION: (1)..(43)
<223> OTHER INFORMATION: AcmA cell wall binding domain homologue

<400> SEQUENCE: 27

Tyr Thr Val Lys Ser Gly Asp Thr Leu Asn Lys Ile Ala Ala Gln Tyr
1               5                   10                  15
Gly Val Thr Val Ala Asn Leu Arg Ser Trp Asn Gly Ile Ser Gly Asp
            20                  25                  30
Leu Ile Phe Val Gly Gln Lys Leu Ile Val Lys
            35                  40

<210> SEQ ID NO 28
<211> LENGTH: 43
<212> TYPE: PRT
<213> ORGANISM: Enterococcus faecalis
<220> FEATURE:
<221> NAME/KEY: SITE
<222> LOCATION: (1)..(43)
<223> OTHER INFORMATION: AcmA cell wall binding domain homologue

<400> SEQUENCE: 28

Tyr Thr Ile Lys Ser Gly Asp Thr Leu Asn Lys Ile Ala Ala Gln Tyr
1               5                   10                  15
Gly Val Ser Val Ala Asn Leu Arg Ser Trp Asn Gly Ile Ser Gly Asp
            20                  25                  30
Leu Ile Phe Ala Gly Gln Lys Ile Ile Val Lys
            35                  40

<210> SEQ ID NO 29
<211> LENGTH: 43
<212> TYPE: PRT
<213> ORGANISM: Enterococcus faecalis
<220> FEATURE:
<221> NAME/KEY: SITE
<222> LOCATION: (1)..(43)
<223> OTHER INFORMATION: AcmA cell wall binding domain homologue

<400> SEQUENCE: 29

Tyr Thr Ile Lys Ser Gly Asp Thr Leu Asn Lys Ile Ser Ala Gln Phe
1               5                   10                  15
Gly Val Ser Val Ala Asn Leu Arg Ser Trp Asn Gly Ile Lys Gly Asp
            20                  25                  30
Leu Ile Phe Ala Gly Gln Thr Ile Ile Val Lys
            35                  40

<210> SEQ ID NO 30
<211> LENGTH: 43
<212> TYPE: PRT
<213> ORGANISM: Enterococcus faecalis
<220> FEATURE:
<221> NAME/KEY: SITE
<222> LOCATION: (1)..(43)
<223> OTHER INFORMATION: AcmA cell wall binding domain homologue

<400> SEQUENCE: 30

His Thr Val Lys Ser Gly Asp Ser Leu Trp Gly Leu Ser Met Gln Tyr
1               5                   10                  15
Gly Ile Ser Ile Gln Lys Ile Lys Gln Leu Asn Gly Leu Ser Gly Asp
            20                  25                  30
Thr Ile Tyr Ile Gly Gln Thr Leu Lys Val Gly
            35                  40
```

<210> SEQ ID NO 31
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 31

Tyr Thr Val Lys Ser Gly Asp Ser Val Trp Gly Ile Ser His Ser Phe
 1               5                  10                  15

Gly Ile Thr Met Ala Gln Leu Ile Glu Trp Asn Asn Ile Lys Asn Asn
            20                  25                  30

Phe Ile Tyr Pro Gly Gln Lys Leu Thr Ile Lys
        35                  40

<210> SEQ ID NO 32
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 32

Tyr Thr Val Lys Ser Gly Asp Ser Val Trp Lys Ile Ala Asn Asp His
 1               5                  10                  15

Gly Ile Ser Met Asn Gln Leu Ile Glu Trp Asn Asn Ile Lys Asn Asn
            20                  25                  30

Phe Val Tyr Pro Gly Gln Gln Leu Val Val Ser
        35                  40

<210> SEQ ID NO 33
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 33

Tyr Thr Val Lys Ala Gly Glu Ser Val Trp Ser Val Ser Asn Lys Phe
 1               5                  10                  15

Gly Ile Ser Met Asn Gln Leu Ile Gln Trp Asn Asn Ile Lys Asn Asn
            20                  25                  30

Phe Ile Tyr Pro Gly Gln Lys Leu Ile Val Lys
        35                  40

<210> SEQ ID NO 34
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 34

Tyr Thr Val Lys Ala Gly Glu Ser Val Trp Gly Val Ala Asn Lys Asn
 1               5                  10                  15

Gly Ile Ser Met Asn Gln Leu Ile Glu Trp Asn Asn Ile Lys Asn Asn
            20                  25                  30

Phe Ile Tyr Pro Gly Gln Lys Leu Ile Val Lys
          35                  40

<210> SEQ ID NO 35
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 35

Tyr Thr Val Lys Ala Gly Glu Ser Val Trp Gly Val Ala Asn Lys His
 1               5                  10                  15

His Ile Thr Met Asp Gln Leu Ile Glu Trp Asn Asn Ile Lys Asn Asn
             20                  25                  30

Phe Ile Tyr Pro Gly Gln Glu Val Ile Val Lys
          35                  40

<210> SEQ ID NO 36
<211> LENGTH: 43
<212> TYPE: PRT
<213> ORGANISM: Enterococcus hirae
<220> FEATURE:
<221> NAME/KEY: SITE
<222> LOCATION: (1)..(43)
<223> OTHER INFORMATION: AcmA cell wall binding domain homologue

<400> SEQUENCE: 36

Tyr Thr Val Lys Ala Gly Glu Ser Val Trp Gly Val Ala Asp Ser His
 1               5                  10                  15

Gly Ile Thr Met Asn Gln Leu Ile Glu Trp Asn Asn Ile Lys Asn Asn
             20                  25                  30

Phe Ile Tyr Pro Gly Gln Gln Leu Ile Val Lys
          35                  40

<210> SEQ ID NO 37
<211> LENGTH: 43
<212> TYPE: PRT
<213> ORGANISM: Listeria monocytogenes
<220> FEATURE:
<221> NAME/KEY: SITE
<222> LOCATION: (1)..(43)
<223> OTHER INFORMATION: AcmA cell wall binding domain homologue

<400> SEQUENCE: 37

Val Val Val Glu Ala Gly Asp Thr Leu Trp Gly Ile Ala Gln Ser Lys
 1               5                  10                  15

Gly Thr Thr Val Asp Ala Ile Lys Lys Ala Asn Asn Leu Thr Thr Asp
             20                  25                  30

Lys Ile Val Pro Gly Gln Lys Leu Gln Val Asn
          35                  40

<210> SEQ ID NO 38
<211> LENGTH: 43
<212> TYPE: PRT
<213> ORGANISM: Listeria monocytogenes
<220> FEATURE:
<221> NAME/KEY: SITE
<222> LOCATION: (1)..(43)
<223> OTHER INFORMATION: AcmA cell wall binding domain homologue

<400> SEQUENCE: 38

```
His Ala Val Lys Ser Gly Asp Thr Ile Trp Ala Leu Ser Val Lys Tyr
1               5                   10                  15

Gly Val Ser Val Gln Asp Ile Met Ser Trp Asn Asn Leu Ser Ser Ser
                20                  25                  30

Ser Ile Tyr Val Gly Gln Lys Leu Ala Ile Lys
            35                  40
```

<210> SEQ ID NO 39
<211> LENGTH: 43
<212> TYPE: PRT
<213> ORGANISM: Listeria monocytogenes
<220> FEATURE:
<221> NAME/KEY: SITE
<222> LOCATION: (1)..(43)
<223> OTHER INFORMATION: AcmA cell wall binding domain homologue

<400> SEQUENCE: 39

```
Val Val Val Glu Ala Gly Asp Thr Leu Trp Gly Ile Ala Gln Ser Lys
1               5                   10                  15

Gly Thr Thr Val Asp Ala Ile Lys Lys Ala Asn Asn Leu Thr Thr Asp
                20                  25                  30

Lys Ile Val Pro Gly Gln Lys Leu Gln Val Asn
            35                  40
```

<210> SEQ ID NO 40
<211> LENGTH: 43
<212> TYPE: PRT
<213> ORGANISM: Listeria innocua
<220> FEATURE:
<221> NAME/KEY: SITE
<222> LOCATION: (1)..(43)
<223> OTHER INFORMATION: AcmA cell wall binding domain homologue

<400> SEQUENCE: 40

```
His Asn Val Lys Ser Gly Asp Thr Ile Trp Ala Leu Ser Val Lys Tyr
1               5                   10                  15

Gly Val Ser Val Gln Asp Ile Met Ser Trp Asn Asn Leu Ser Ser Ser
                20                  25                  30

Ser Ile Tyr Val Gly Gln Lys Pro Ala Ile Lys
            35                  40
```

<210> SEQ ID NO 41
<211> LENGTH: 43
<212> TYPE: PRT
<213> ORGANISM: Listeria ivanovii
<220> FEATURE:
<221> NAME/KEY: SITE
<222> LOCATION: (1)..(43)
<223> OTHER INFORMATION: AcmA cell wall binding domain homologue

<400> SEQUENCE: 41

```
Val Val Val Glu Ala Gly Asp Thr Leu Trp Gly Ile Ala Gln Asp Lys
1               5                   10                  15

Gly Thr Thr Val Asp Ala Leu Lys Lys Ala Asn Asn Leu Thr Ser Asp
                20                  25                  30

Lys Ile Val Pro Gly Gln Lys Leu Gln Ile Thr
            35                  40
```

<210> SEQ ID NO 42
<211> LENGTH: 43
<212> TYPE: PRT
<213> ORGANISM: Listeria ivanovii
<220> FEATURE:
<221> NAME/KEY: SITE

```
<222> LOCATION: (1)..(43)
<223> OTHER INFORMATION: AcmA cell wall binding domain homologue

<400> SEQUENCE: 42

Tyr Thr Val Lys Ser Gly Asp Thr Ile Trp Ala Leu Ser Ser Lys Tyr
  1               5                  10                  15

Gly Thr Ser Val Gln Asn Ile Met Ser Trp Asn Asn Leu Ser Ser Ser
             20                  25                  30

Ser Ile Tyr Val Gly Gln Val Leu Ala Val Lys
         35                  40

<210> SEQ ID NO 43
<211> LENGTH: 43
<212> TYPE: PRT
<213> ORGANISM: Listeria ivanovii
<220> FEATURE:
<221> NAME/KEY: SITE
<222> LOCATION: (1)..(43)
<223> OTHER INFORMATION: AcmA cell wall binding domain homologue

<400> SEQUENCE: 43

Tyr Thr Val Lys Ser Gly Asp Thr Leu Ser Lys Ile Ala Thr Thr Phe
  1               5                  10                  15

Gly Thr Thr Val Ser Lys Ile Lys Ala Leu Asn Gly Leu Asn Ser Asp
             20                  25                  30

Asn Leu Gln Val Gly Gln Val Leu Lys Val Lys
         35                  40

<210> SEQ ID NO 44
<211> LENGTH: 43
<212> TYPE: PRT
<213> ORGANISM: Listeria seeligeri
<220> FEATURE:
<221> NAME/KEY: SITE
<222> LOCATION: (1)..(43)
<223> OTHER INFORMATION: AcmA cell wall binding domain homologue

<400> SEQUENCE: 44

Val Val Val Glu Ala Gly Asp Thr Leu Trp Gly Ile Ala Gln Asp Asn
  1               5                  10                  15

Gly Thr Thr Val Asp Ala Leu Lys Lys Ala Asn Lys Leu Thr Thr Asp
             20                  25                  30

Lys Ile Val Pro Gly Gln Lys Leu Gln Val Thr
         35                  40

<210> SEQ ID NO 45
<211> LENGTH: 43
<212> TYPE: PRT
<213> ORGANISM: Listeria seeligeri
<220> FEATURE:
<221> NAME/KEY: SITE
<222> LOCATION: (1)..(43)
<223> OTHER INFORMATION: AcmA cell wall binding domain homologue

<400> SEQUENCE: 45

His Thr Val Lys Ser Gly Asp Thr Ile Trp Ala Leu Ser Val Lys Tyr
  1               5                  10                  15

Gly Ala Ser Val Gln Asp Leu Met Ser Trp Asn Asn Leu Ser Ser Ser
             20                  25                  30

Ser Ile Tyr Val Gly Gln Asn Ile Ala Val Lys
         35                  40

<210> SEQ ID NO 46
```

```
<210> SEQ ID NO 46
<211> LENGTH: 43
<212> TYPE: PRT
<213> ORGANISM: Listeria seeligeri
<220> FEATURE:
<221> NAME/KEY: SITE
<222> LOCATION: (1)..(43)
<223> OTHER INFORMATION: AcmA cell wall binding domain homologue

<400> SEQUENCE: 46

Tyr Thr Val Lys Ser Gly Asp Thr Leu Gly Lys Ile Ala Ser Thr Phe
 1               5                  10                  15

Gly Thr Thr Val Ser Lys Ile Lys Ala Leu Asn Gly Leu Thr Ser Asp
                20                  25                  30

Asn Leu Gln Val Gly Asp Val Leu Lys Val Lys
            35                  40

<210> SEQ ID NO 47
<211> LENGTH: 43
<212> TYPE: PRT
<213> ORGANISM: Listeria welshimeri
<220> FEATURE:
<221> NAME/KEY: SITE
<222> LOCATION: (1)..(43)
<223> OTHER INFORMATION: AcmA cell wall binding domain homologue

<400> SEQUENCE: 47

Val Val Val Glu Ala Gly Asp Thr Leu Trp Gly Ile Ala Gln Ser Lys
 1               5                  10                  15

Gly Thr Thr Val Asp Ala Leu Lys Lys Ala Asn Asn Leu Thr Ser Asp
                20                  25                  30

Lys Ile Val Pro Gly Gln Lys Leu Gln Val Thr
            35                  40

<210> SEQ ID NO 48
<211> LENGTH: 43
<212> TYPE: PRT
<213> ORGANISM: Listeria welshimeri
<220> FEATURE:
<221> NAME/KEY: SITE
<222> LOCATION: (1)..(43)
<223> OTHER INFORMATION: AcmA cell wall binding domain homologue

<400> SEQUENCE: 48

His Thr Val Lys Ser Gly Asp Thr Ile Trp Ala Leu Ser Val Lys Tyr
 1               5                  10                  15

Gly Ala Ser Val Gln Asp Leu Met Ser Trp Asn Asn Leu Ser Ser Ser
                20                  25                  30

Ser Ile Tyr Val Gly Gln Lys Ile Ala Val Lys
            35                  40

<210> SEQ ID NO 49
<211> LENGTH: 43
<212> TYPE: PRT
<213> ORGANISM: Listeria welshimeri
<220> FEATURE:
<221> NAME/KEY: SITE
<222> LOCATION: (1)..(43)
<223> OTHER INFORMATION: AcmA cell wall binding domain homologue

<400> SEQUENCE: 49

Tyr Thr Val Lys Ser Gly Asp Ser Leu Ser Lys Ile Ala Asn Thr Phe
 1               5                  10                  15

Gly Thr Ser Val Ser Lys Ile Lys Ala Leu Asn Asn Leu Thr Ser Asp
                20                  25                  30
```

-continued

```
Asn Leu Gln Val Gly Thr Val Leu Lys Val Lys
            35                  40

<210> SEQ ID NO 50
<211> LENGTH: 43
<212> TYPE: PRT
<213> ORGANISM: Listeria grayi
<220> FEATURE:
<221> NAME/KEY: SITE
<222> LOCATION: (1)..(43)
<223> OTHER INFORMATION: AcmA cell wall binding domain homologue

<400> SEQUENCE: 50

Val Val Val Ala Ser Gly Asp Thr Leu Trp Gly Ile Ala Ser Lys Thr
 1               5                  10                  15

Gly Thr Thr Val Asp Gln Leu Lys Gln Leu Asn Lys Leu Asp Ser Asp
            20                  25                  30

Arg Ile Val Pro Gly Gln Lys Leu Thr Ile Lys
            35                  40

<210> SEQ ID NO 51
<211> LENGTH: 43
<212> TYPE: PRT
<213> ORGANISM: Listeria grayi
<220> FEATURE:
<221> NAME/KEY: SITE
<222> LOCATION: (1)..(43)
<223> OTHER INFORMATION: AcmA cell wall binding domain homologue

<400> SEQUENCE: 51

Tyr Lys Val Lys Ser Gly Asp Thr Ile Trp Ala Leu Ser Val Lys Tyr
 1               5                  10                  15

Gly Val Pro Val Gln Lys Leu Ile Glu Trp Asn Asn Leu Ser Ser Ser
            20                  25                  30

Ser Ile Tyr Val Gly Gln Thr Ile Ala Val Lys
            35                  40

<210> SEQ ID NO 52
<211> LENGTH: 44
<212> TYPE: PRT
<213> ORGANISM: Listeria grayi
<220> FEATURE:
<221> NAME/KEY: SITE
<222> LOCATION: (1)..(44)
<223> OTHER INFORMATION: AcmA cell wall binding domain homologue

<400> SEQUENCE: 52

Tyr Lys Val Gln Asn Gly Asp Ser Leu Gly Lys Ile Ala Ser Leu Phe
 1               5                  10                  15

Lys Val Ser Val Ala Asp Leu Thr Asn Trp Asn Asn Leu Asn Ala Thr
            20                  25                  30

Ile Thr Ile Tyr Ala Gly Gln Glu Leu Ser Val Lys
            35                  40

<210> SEQ ID NO 53
<211> LENGTH: 43
<212> TYPE: PRT
<213> ORGANISM: Haemophilus influenzae
<220> FEATURE:
<221> NAME/KEY: SITE
<222> LOCATION: (1)..(43)
<223> OTHER INFORMATION: AcmA cell wall binding domain homologue

<400> SEQUENCE: 53

His Ile Val Lys Lys Gly Glu Ser Leu Gly Ser Leu Ser Asn Lys Tyr
```

```
                 1               5                  10                 15
His Val Lys Val Ser Asp Ile Ile Lys Leu Asn Gln Leu Lys Arg Lys
                20                 25                 30

Thr Leu Trp Leu Asn Glu Ser Ile Lys Ile Pro
        35                 40

<210> SEQ ID NO 54
<211> LENGTH: 44
<212> TYPE: PRT
<213> ORGANISM: Haemophilus influenzae
<220> FEATURE:
<221> NAME/KEY: SITE
<222> LOCATION: (1)..(44)
<223> OTHER INFORMATION: AcmA cell wall binding domain homologue

<400> SEQUENCE: 54

His Lys Val Thr Lys Asn Gln Thr Leu Tyr Ala Ile Ser Arg Glu Tyr
 1               5                  10                 15

Asn Ile Pro Val Asn Ile Leu Leu Ser Leu Asn Pro His Leu Lys Asn
                20                 25                 30

Gly Lys Val Ile Thr Gly Gln Lys Ile Lys Leu Arg
        35                 40

<210> SEQ ID NO 55
<211> LENGTH: 45
<212> TYPE: PRT
<213> ORGANISM: Haemophilus influenzae
<220> FEATURE:
<221> NAME/KEY: SITE
<222> LOCATION: (1)..(45)
<223> OTHER INFORMATION: AcmA cell wall binding domain homologue

<400> SEQUENCE: 55

Tyr Thr Val Thr Glu Gly Asp Thr Leu Lys Asp Val Leu Val Leu Ser
 1               5                  10                 15

Gly Leu Asp Asp Ser Ser Val Gln Pro Leu Ile Ala Leu Asp Pro Glu
                20                 25                 30

Leu Ala His Leu Lys Ala Gly Gln Gln Phe Tyr Trp Ile
        35                 40                 45

<210> SEQ ID NO 56
<211> LENGTH: 45
<212> TYPE: PRT
<213> ORGANISM: Haemophilus influenzae
<220> FEATURE:
<221> NAME/KEY: SITE
<222> LOCATION: (1)..(45)
<223> OTHER INFORMATION: AcmA cell wall binding domain homologue

<400> SEQUENCE: 56

Tyr Lys Val Asn Lys Gly Asp Thr Met Phe Leu Ile Ala Tyr Leu Ala
 1               5                  10                 15

Gly Ile Asp Val Lys Glu Leu Ala Ala Leu Asn Asn Leu Ser Glu Pro
                20                 25                 30

Asn Tyr Asn Leu Ser Leu Gly Gln Val Leu Lys Ile Ser
        35                 40                 45

<210> SEQ ID NO 57
<211> LENGTH: 44
<212> TYPE: PRT
<213> ORGANISM: Haemophilus somnus
<220> FEATURE:
<221> NAME/KEY: SITE
<222> LOCATION: (1)..(44)
```

<223> OTHER INFORMATION: AcmA cell wall binding domain homologue

<400> SEQUENCE: 57

Tyr Lys Val Arg Lys Gly Asp Thr Met Phe Leu Ile Ala Tyr Ile Ser
1               5                   10                  15

Gly Met Asp Ile Lys Glu Leu Ala Thr Leu Asn Asn Met Ser Glu Pro
            20                  25                  30

Tyr His Leu Ser Ile Gly Gln Val Leu Lys Ile Ala
        35                  40

<210> SEQ ID NO 58
<211> LENGTH: 43
<212> TYPE: PRT
<213> ORGANISM: Helicobacter pylori
<220> FEATURE:
<221> NAME/KEY: SITE
<222> LOCATION: (1)..(43)
<223> OTHER INFORMATION: AcmA cell wall binding domain homologue

<400> SEQUENCE: 58

His Val Val Leu Pro Lys Glu Thr Leu Ser Ser Ile Ala Lys Arg Tyr
1               5                   10                  15

Gln Val Ser Ile Ser Asn Ile Gln Leu Ala Asn Asp Leu Lys Asp Ser
            20                  25                  30

Asn Ile Phe Ile His Gln Arg Leu Ile Ile Arg
        35                  40

<210> SEQ ID NO 59
<211> LENGTH: 44
<212> TYPE: PRT
<213> ORGANISM: Pseudomonas aeruginosa
<220> FEATURE:
<221> NAME/KEY: SITE
<222> LOCATION: (1)..(44)
<223> OTHER INFORMATION: AcmA cell wall binding domain homologue

<400> SEQUENCE: 59

Tyr Ile Val Arg Arg Gly Asp Thr Leu Tyr Ser Ile Ala Phe Arg Phe
1               5                   10                  15

Gly Trp Asp Trp Lys Ala Leu Ala Ala Arg Asn Gly Ile Ala Pro Pro
            20                  25                  30

Tyr Thr Ile Gln Val Gly Gln Ala Ile Gln Phe Gly
        35                  40

<210> SEQ ID NO 60
<211> LENGTH: 44
<212> TYPE: PRT
<213> ORGANISM: Pseudomonas putida
<220> FEATURE:
<221> NAME/KEY: SITE
<222> LOCATION: (1)..(44)
<223> OTHER INFORMATION: AcmA cell wall binding domain homologue

<400> SEQUENCE: 60

Tyr Ile Val Lys Pro Gly Asp Thr Leu Phe Ser Ile Ala Phe Arg Tyr
1               5                   10                  15

Gly Trp Asp Tyr Lys Glu Leu Ala Ala Arg Asn Gly Ile Pro Ala Pro
            20                  25                  30

Tyr Thr Ile Arg Pro Gly Gln Pro Ile Arg Phe Ser
        35                  40

<210> SEQ ID NO 61

```
<211> LENGTH: 44
<212> TYPE: PRT
<213> ORGANISM: Sinorhizobium meliloti
<220> FEATURE:
<221> NAME/KEY: SITE
<222> LOCATION: (1)..(44)
<223> OTHER INFORMATION: AcmA cell wall binding domain homologue

<400> SEQUENCE: 61

Ile Met Val Arg Gln Gly Asp Thr Val Thr Val Leu Ala Arg Arg Phe
 1               5                  10                  15

Gly Val Pro Glu Lys Glu Ile Leu Lys Ala Asn Gly Leu Lys Ser Ala
             20                  25                  30

Ser Gln Val Glu Pro Gly Gln Arg Leu Val Ile Pro
         35                  40

<210> SEQ ID NO 62
<211> LENGTH: 44
<212> TYPE: PRT
<213> ORGANISM: Synechocystis sp.
<220> FEATURE:
<221> NAME/KEY: SITE
<222> LOCATION: (1)..(44)
<223> OTHER INFORMATION: AcmA cell wall binding domain homologue

<400> SEQUENCE: 62

His Gln Val Lys Glu Gly Glu Ser Leu Trp Gln Ile Ser Gln Ala Phe
 1               5                  10                  15

Gln Val Asp Ala Lys Ala Ile Ala Leu Ala Asn Ser Ile Ser Thr Asp
             20                  25                  30

Thr Glu Leu Gln Ala Gly Gln Val Leu Asn Ile Pro
         35                  40

<210> SEQ ID NO 63
<211> LENGTH: 44
<212> TYPE: PRT
<213> ORGANISM: Synechocystis sp.
<220> FEATURE:
<221> NAME/KEY: SITE
<222> LOCATION: (1)..(44)
<223> OTHER INFORMATION: AcmA cell wall binding domain homologue

<400> SEQUENCE: 63

His Val Val Lys Ala Gly Glu Thr Ile Asp Ser Ile Ala Ala Gln Tyr
 1               5                  10                  15

Gln Leu Val Pro Ala Thr Leu Ile Ser Val Asn Asn Gln Leu Ser Ser
             20                  25                  30

Gly Gln Val Thr Pro Gly Gln Thr Ile Leu Ile Pro
         35                  40

<210> SEQ ID NO 64
<211> LENGTH: 45
<212> TYPE: PRT
<213> ORGANISM: Aquifex aeolicus
<220> FEATURE:
<221> NAME/KEY: SITE
<222> LOCATION: (1)..(45)
<223> OTHER INFORMATION: AcmA cell wall binding domain homologue

<400> SEQUENCE: 64

Tyr Lys Val Lys Lys Gly Asp Ser Leu Trp Lys Ile Ala Lys Glu Tyr
 1               5                  10                  15

Lys Thr Ser Ile Gly Lys Leu Leu Glu Leu Asn Pro Lys Leu Lys Asn
             20                  25                  30
```

```
Arg Lys Tyr Leu Arg Pro Gly Glu Lys Ile Cys Leu Lys
            35                  40                  45

<210> SEQ ID NO 65
<211> LENGTH: 43
<212> TYPE: PRT
<213> ORGANISM: Aquifex aeolicus
<220> FEATURE:
<221> NAME/KEY: SITE
<222> LOCATION: (1)..(43)
<223> OTHER INFORMATION: AcmA cell wall binding domain homologue

<400> SEQUENCE: 65

Tyr Arg Val Lys Arg Gly Asp Ser Leu Ile Lys Ile Ala Lys Lys Phe
 1               5                  10                  15

Gly Val Ser Val Lys Glu Ile Lys Arg Val Asn Lys Leu Lys Gly Asn
            20                  25                  30

Arg Ile Tyr Val Gly Gln Lys Leu Lys Ile Pro
            35                  40

<210> SEQ ID NO 66
<211> LENGTH: 43
<212> TYPE: PRT
<213> ORGANISM: Aquifex aeolicus
<220> FEATURE:
<221> NAME/KEY: SITE
<222> LOCATION: (1)..(43)
<223> OTHER INFORMATION: AcmA cell wall binding domain homologue

<400> SEQUENCE: 66

Tyr Arg Val Arg Arg Gly Asp Thr Leu Ile Lys Ile Ala Lys Arg Phe
 1               5                  10                  15

Arg Thr Ser Val Lys Glu Ile Lys Arg Ile Asn Arg Leu Lys Gly Asn
            20                  25                  30

Leu Ile Arg Val Gly Gln Lys Leu Lys Ile Pro
            35                  40

<210> SEQ ID NO 67
<211> LENGTH: 44
<212> TYPE: PRT
<213> ORGANISM: Volvox carteri
<220> FEATURE:
<221> NAME/KEY: SITE
<222> LOCATION: (1)..(44)
<223> OTHER INFORMATION: AcmA cell wall binding domain homologue

<400> SEQUENCE: 67

Tyr Thr Ile Gln Pro Gly Asp Thr Phe Trp Ala Ile Ala Gln Arg Arg
 1               5                  10                  15

Gly Thr Thr Val Asp Val Ile Gln Ser Leu Asn Pro Gly Val Val Pro
            20                  25                  30

Thr Arg Leu Gln Val Gly Gln Val Ile Asn Val Pro
            35                  40

<210> SEQ ID NO 68
<211> LENGTH: 44
<212> TYPE: PRT
<213> ORGANISM: F. nagariensis
<220> FEATURE:
<221> NAME/KEY: SITE
<222> LOCATION: (1)..(44)
<223> OTHER INFORMATION: AcmA cell wall binding domain homologue

<400> SEQUENCE: 68

Tyr Thr Ile Gln Pro Gly Asp Thr Phe Trp Ala Ile Ala Gln Arg Arg
```

-continued

```
                1               5              10              15
Gly Thr Thr Val Asp Val Ile Gln Ser Leu Asn Pro Gly Val Asn Pro
                    20                  25                  30

Ala Arg Leu Gln Val Gly Gln Val Ile Asn Val Pro
        35                  40

<210> SEQ ID NO 69
<211> LENGTH: 44
<212> TYPE: PRT
<213> ORGANISM: Staphylococcus aureus
<220> FEATURE:
<221> NAME/KEY: SITE
<222> LOCATION: (1)..(44)
<223> OTHER INFORMATION: AcmA cell wall binding domain homologue

<400> SEQUENCE: 69

His Val Val Lys Pro Gly Asp Thr Val Asn Asp Ile Ala Lys Ala Asn
  1               5                  10                  15

Gly Thr Thr Ala Asp Lys Ile Ala Ala Asp Asn Lys Leu Ala Asp Lys
                    20                  25                  30

Asn Met Ile Lys Pro Gly Gln Glu Leu Val Val Asp
        35                  40

<210> SEQ ID NO 70
<211> LENGTH: 44
<212> TYPE: PRT
<213> ORGANISM: Staphylococcus aureus
<220> FEATURE:
<221> NAME/KEY: SITE
<222> LOCATION: (1)..(44)
<223> OTHER INFORMATION: AcmA cell wall binding domain homologue

<400> SEQUENCE: 70

Tyr Thr Val Lys Lys Gly Asp Thr Leu Ser Ala Ile Ala Leu Lys Tyr
  1               5                  10                  15

Lys Thr Thr Val Ser Asn Ile Gln Asn Thr Asn Asn Ile Ala Asn Pro
                    20                  25                  30

Asn Leu Ile Phe Ile Gly Gln Lys Leu Lys Val Pro
        35                  40

<210> SEQ ID NO 71
<211> LENGTH: 44
<212> TYPE: PRT
<213> ORGANISM: Colletotrichum
<220> FEATURE:
<221> NAME/KEY: SITE
<222> LOCATION: (1)..(44)
<223> OTHER INFORMATION: AcmA cell wall binding domain homologue

<400> SEQUENCE: 71

His Lys Val Lys Ser Gly Glu Ser Leu Thr Thr Ile Ala Glu Lys Tyr
  1               5                  10                  15

Asp Thr Gly Ile Cys Asn Ile Ala Lys Leu Asn Asn Leu Ala Asp Pro
                    20                  25                  30

Asn Phe Ile Asp Leu Asn Gln Asp Leu Gln Ile Pro
        35                  40

<210> SEQ ID NO 72
<211> LENGTH: 44
<212> TYPE: PRT
<213> ORGANISM: Colletotrichum lindemuthianum
<220> FEATURE:
<221> NAME/KEY: SITE
<222> LOCATION: (1)..(44)
```

-continued

<223> OTHER INFORMATION: AcmA cell wall binding domain homologue

<400> SEQUENCE: 72

```
Tyr Ser Val Val Ser Gly Asp Thr Leu Thr Ser Ile Ala Gln Ala Leu
  1               5                  10                  15

Gln Ile Thr Leu Gln Ser Leu Lys Asp Ala Asn Pro Gly Val Val Pro
             20                  25                  30

Glu His Leu Asn Val Gly Gln Lys Leu Asn Val Pro
         35                  40
```

<210> SEQ ID NO 73
<211> LENGTH: 43
<212> TYPE: PRT
<213> ORGANISM: Colletotrichum chlamydophila
<220> FEATURE:
<221> NAME/KEY: SITE
<222> LOCATION: (1)..(43)
<223> OTHER INFORMATION: AcmA cell wall binding domain homologue

<400> SEQUENCE: 73

```
Ile Val Tyr Arg Glu Gly Asp Ser Leu Ser Lys Ile Ala Lys Lys Tyr
  1               5                  10                  15

Lys Leu Ser Val Thr Glu Leu Lys Lys Ile Asn Lys Leu Asp Ser Asp
             20                  25                  30

Ala Ile Tyr Ala Gly Gln Arg Leu Cys Leu Gln
         35                  40
```

<210> SEQ ID NO 74
<211> LENGTH: 43
<212> TYPE: PRT
<213> ORGANISM: Colletotrichum pneumoniae
<220> FEATURE:
<221> NAME/KEY: SITE
<222> LOCATION: (1)..(43)
<223> OTHER INFORMATION: AcmA cell wall binding domain homologue

<400> SEQUENCE: 74

```
Tyr Val Val Gln Asp Gly Asp Ser Leu Trp Leu Ile Ala Lys Arg Phe
  1               5                  10                  15

Gly Ile Pro Met Asp Lys Ile Ile Gln Lys Asn Gly Leu Asn His His
             20                  25                  30

Arg Leu Phe Pro Gly Lys Val Leu Lys Leu Pro
         35                  40
```

<210> SEQ ID NO 75
<211> LENGTH: 43
<212> TYPE: PRT
<213> ORGANISM: Colletotrichum pneumoniae
<220> FEATURE:
<221> NAME/KEY: SITE
<222> LOCATION: (1)..(43)
<223> OTHER INFORMATION: AcmA cell wall binding domain homologue

<400> SEQUENCE: 75

```
Val Val Val Lys Lys Gly Asp Phe Leu Glu Arg Ile Ala Arg Ala Asn
  1               5                  10                  15

His Thr Thr Val Ala Lys Leu Met Gln Ile Asn Asp Leu Thr Thr Thr
             20                  25                  30

Gln Leu Lys Ile Gly Gln Val Ile Lys Val Pro
         35                  40
```

<210> SEQ ID NO 76
<211> LENGTH: 46

-continued

```
<212> TYPE: PRT
<213> ORGANISM: Colletotrichum pneumoniae
<220> FEATURE:
<221> NAME/KEY: SITE
<222> LOCATION: (1)..(46)
<223> OTHER INFORMATION: Acma cell wall binding domain homologue

<400> SEQUENCE: 76

Tyr Ile Val Gln Glu Gly Asp Ser Pro Trp Thr Ile Ala Leu Arg Asn
  1               5                  10                  15

His Ile Arg Leu Asp Asp Leu Leu Lys Met Asn Asp Leu Asp Glu Tyr
             20                  25                  30

Lys Ala Arg Arg Leu Lys Pro Gly Asp Gln Leu Arg Ile Arg
         35                  40                  45

<210> SEQ ID NO 77
<211> LENGTH: 43
<212> TYPE: PRT
<213> ORGANISM: Chlamydia trachomatis
<220> FEATURE:
<221> NAME/KEY: SITE
<222> LOCATION: (1)..(43)
<223> OTHER INFORMATION: AcmA cell wall binding domain homologue

<400> SEQUENCE: 77

Val Ile Val Lys Lys Gly Asp Phe Leu Glu Arg Ile Ala Arg Ser Asn
  1               5                  10                  15

His Thr Thr Val Ser Ala Leu Met Gln Leu Asn Asp Leu Ser Ser Thr
             20                  25                  30

Gln Leu Gln Ile Gly Gln Val Leu Arg Val Pro
         35                  40

<210> SEQ ID NO 78
<211> LENGTH: 46
<212> TYPE: PRT
<213> ORGANISM: Chlamydia trachomatis
<220> FEATURE:
<221> NAME/KEY: SITE
<222> LOCATION: (1)..(46)
<223> OTHER INFORMATION: AcmA cell wall binding domain homologue

<400> SEQUENCE: 78

Tyr Val Val Lys Glu Gly Asp Ser Pro Trp Ala Ile Ala Leu Ser Asn
  1               5                  10                  15

Gly Ile Arg Leu Asp Glu Leu Leu Lys Leu Asn Gly Leu Asp Glu Gln
             20                  25                  30

Lys Ala Arg Arg Leu Arg Pro Gly Asp Arg Leu Arg Ile Arg
         35                  40                  45

<210> SEQ ID NO 79
<211> LENGTH: 43
<212> TYPE: PRT
<213> ORGANISM: Chlamydia trachomatis
<220> FEATURE:
<221> NAME/KEY: SITE
<222> LOCATION: (1)..(43)
<223> OTHER INFORMATION: AcmA cell wall binding domain homologue

<400> SEQUENCE: 79

His Ile Val Lys Gln Gly Glu Thr Leu Ser Lys Ile Ala Ser Lys Tyr
  1               5                  10                  15

Asn Ile Pro Val Val Glu Leu Lys Lys Leu Asn Lys Leu Asn Ser Asp
             20                  25                  30

Thr Ile Phe Thr Asp Gln Arg Ile Arg Leu Pro
```

```
<210> SEQ ID NO 80
<211> LENGTH: 43
<212> TYPE: PRT
<213> ORGANISM: Prevotella intermedia
<220> FEATURE:
<221> NAME/KEY: SITE
<222> LOCATION: (1)..(43)
<223> OTHER INFORMATION: AcmA cell wall binding domain homologue

<400> SEQUENCE: 80

His Thr Val Arg Ser Asn Glu Ser Leu Tyr Asp Ile Ser Gln Gln Tyr
  1               5                  10                  15

Gly Val Arg Leu Lys Asn Ile Met Lys Ala Asn Arg Lys Ile Val Lys
             20                  25                  30

Arg Gly Ile Lys Ala Gly Asp Arg Val Val Leu
         35                  40

<210> SEQ ID NO 81
<211> LENGTH: 44
<212> TYPE: PRT
<213> ORGANISM: Leuconostoc oenos bacteriophage 10MC
<220> FEATURE:
<221> NAME/KEY: SITE
<222> LOCATION: (1)..(44)
<223> OTHER INFORMATION: AcmA cell wall binding domain homologue

<400> SEQUENCE: 81

Tyr Thr Val Gln Ser Gly Asp Thr Leu Gly Ala Ile Ala Ala Lys Tyr
  1               5                  10                  15

Gly Thr Thr Tyr Gln Lys Leu Ala Ser Leu Asn Gly Ile Gly Ser Pro
             20                  25                  30

Tyr Ile Ile Ile Pro Gly Glu Lys Leu Lys Val Ser
         35                  40

<210> SEQ ID NO 82
<211> LENGTH: 44
<212> TYPE: PRT
<213> ORGANISM: Leuconostoc oenos bacteriophage 10MC
<220> FEATURE:
<221> NAME/KEY: SITE
<222> LOCATION: (1)..(44)
<223> OTHER INFORMATION: AcmA cell wall binding domain homologue

<400> SEQUENCE: 82

Tyr Lys Val Ala Ser Gly Asp Thr Leu Ser Ala Ile Ala Ser Lys Tyr
  1               5                  10                  15

Gly Thr Ser Val Ser Lys Leu Val Ser Leu Asn Gly Leu Lys Asn Ala
             20                  25                  30

Asn Tyr Ile Tyr Val Gly Glu Asn Leu Lys Ile Lys
         35                  40

<210> SEQ ID NO 83
<211> LENGTH: 44
<212> TYPE: PRT
<213> ORGANISM: Oenococcus oeni
<220> FEATURE:
<221> NAME/KEY: SITE
<222> LOCATION: (1)..(44)
<223> OTHER INFORMATION: AcmA cell wall binding domain homologue

<400> SEQUENCE: 83

Tyr Thr Val Arg Ser Gly Asp Thr Leu Gly Ala Ile Ala Ala Lys Tyr
  1               5                  10                  15
```

Gly Thr Thr Tyr Gln Lys Leu Ala Ser Leu Asn Gly Ile Gly Ser Pro
            20                  25                  30

Tyr Ile Ile Ile Pro Gly Glu Lys Leu Lys Val Ser
            35                  40

<210> SEQ ID NO 84
<211> LENGTH: 44
<212> TYPE: PRT
<213> ORGANISM: Oenococcus oeni
<220> FEATURE:
<221> NAME/KEY: SITE
<222> LOCATION: (1)..(44)
<223> OTHER INFORMATION: AcmA cell wall binding domain homologue

<400> SEQUENCE: 84

Tyr Lys Val Ala Ser Gly Asp Thr Leu Ser Ala Ile Ala Ser Lys Tyr
1               5                   10                  15

Gly Thr Ser Val Ser Lys Leu Val Ser Leu Asn Gly Leu Lys Asn Ala
            20                  25                  30

Asn Tyr Ile Tyr Val Gly Gln Thr Leu Arg Ile Lys
            35                  40

<210> SEQ ID NO 85
<211> LENGTH: 44
<212> TYPE: PRT
<213> ORGANISM: Thermotoga maritima
<220> FEATURE:
<221> NAME/KEY: SITE
<222> LOCATION: (1)..(44)
<223> OTHER INFORMATION: AcmA cell wall binding domain homologue

<400> SEQUENCE: 85

Tyr Lys Val Gln Lys Asn Asp Thr Leu Tyr Ser Ile Ser Leu Asn Phe
1               5                   10                  15

Gly Ile Ser Pro Ser Leu Leu Leu Asp Trp Asn Pro Gly Leu Asp Pro
            20                  25                  30

His Ser Leu Arg Val Gly Gln Glu Ile Val Ile Pro
            35                  40

<210> SEQ ID NO 86
<211> LENGTH: 43
<212> TYPE: PRT
<213> ORGANISM: Thermotoga maritima
<220> FEATURE:
<221> NAME/KEY: SITE
<222> LOCATION: (1)..(43)
<223> OTHER INFORMATION: AcmA cell wall binding domain homologue

<400> SEQUENCE: 86

Tyr Thr Val Lys Lys Gly Asp Thr Leu Asp Ala Ile Ala Lys Arg Phe
1               5                   10                  15

Phe Thr Thr Ala Thr Phe Ile Lys Glu Ala Asn Gln Leu Lys Ser Tyr
            20                  25                  30

Thr Ile Tyr Ala Gly Gln Lys Leu Phe Ile Pro
            35                  40

<210> SEQ ID NO 87
<211> LENGTH: 44
<212> TYPE: PRT
<213> ORGANISM: Thermotoga maritima
<220> FEATURE:
<221> NAME/KEY: SITE
<222> LOCATION: (1)..(44)
<223> OTHER INFORMATION: AcmA cell wall binding domain homologue

<400> SEQUENCE: 87

His Val Lys Arg Gly Glu Thr Leu Trp Ser Ile Ala Asn Gln Tyr
1               5                   10                  15

Gly Val Arg Val Gly Asp Ile Val Leu Ile Asn Arg Leu Glu Asp Pro
            20                  25                  30

Asp Arg Ile Val Ala Gly Gln Val Leu Lys Ile Gly
        35                  40

<210> SEQ ID NO 88
<211> LENGTH: 44
<212> TYPE: PRT
<213> ORGANISM: Treponema pallidum
<220> FEATURE:
<221> NAME/KEY: SITE
<222> LOCATION: (1)..(44)
<223> OTHER INFORMATION: AcmA cell wall binding domain homologue

<400> SEQUENCE: 88

His Thr Ile Arg Ser Gly Asp Thr Leu Tyr Ala Leu Ala Arg Arg Tyr
1               5                   10                  15

Gly Leu Gly Val Asp Thr Leu Lys Ala His Asn Arg Ala His Ser Ala
            20                  25                  30

Thr His Leu Lys Ile Gly Gln Lys Leu Ile Ile Pro
        35                  40

<210> SEQ ID NO 89
<211> LENGTH: 44
<212> TYPE: PRT
<213> ORGANISM: Treponema pallidum
<220> FEATURE:
<221> NAME/KEY: SITE
<222> LOCATION: (1)..(44)
<223> OTHER INFORMATION: AcmA cell wall binding domain homologue

<400> SEQUENCE: 89

His Val Val Gln Gln Gly Asp Thr Leu Trp Ser Leu Ala Lys Arg Tyr
1               5                   10                  15

Gly Val Ser Val Glu Asn Leu Ala Glu Glu Asn Asn Leu Ala Val Asp
            20                  25                  30

Ala Thr Leu Ser Leu Gly Met Ile Leu Lys Thr Pro
        35                  40

<210> SEQ ID NO 90
<211> LENGTH: 44
<212> TYPE: PRT
<213> ORGANISM: Treponema pallidum
<220> FEATURE:
<221> NAME/KEY: SITE
<222> LOCATION: (1)..(44)
<223> OTHER INFORMATION: AcmA cell wall binding domain homologue

<400> SEQUENCE: 90

Tyr Glu Val Arg Glu Gly Asp Val Val Gly Arg Ile Ala Gln Arg Tyr
1               5                   10                  15

Asp Ile Ser Gln Asp Ala Ile Ile Ser Leu Asn Lys Leu Arg Ser Thr
            20                  25                  30

Arg Ala Leu Gln Val Gly Gln Leu Leu Lys Ile Pro
        35                  40

<210> SEQ ID NO 91
<211> LENGTH: 44
<212> TYPE: PRT

```
<213> ORGANISM: Treponema pallidum
<220> FEATURE:
<221> NAME/KEY: SITE
<222> LOCATION: (1)..(44)
<223> OTHER INFORMATION: AcmA cell wall binding domain homologue

<400> SEQUENCE: 91

His Val Ile Ala Lys Gly Glu Thr Leu Phe Ser Leu Ser Arg Arg Tyr
  1               5                  10                  15

Gly Val Pro Leu Ser Ala Leu Ala Gln Ala Asn Asn Leu Ala Asn Val
             20                  25                  30

His Gln Leu Val Pro Gly Gln Arg Ile Val Val Pro
         35                  40

<210> SEQ ID NO 92
<211> LENGTH: 44
<212> TYPE: PRT
<213> ORGANISM: Borrelia burgdorferi
<220> FEATURE:
<221> NAME/KEY: SITE
<222> LOCATION: (1)..(44)
<223> OTHER INFORMATION: AcmA cell wall binding domain homologue

<400> SEQUENCE: 92

His Lys Ile Lys Pro Gly Glu Thr Leu Ser His Val Ala Ala Arg Tyr
  1               5                  10                  15

Gln Ile Thr Ser Glu Thr Leu Ile Ser Phe Asn Glu Ile Lys Asp Val
             20                  25                  30

Arg Asn Ile Lys Pro Asn Ser Val Ile Lys Val Pro
         35                  40

<210> SEQ ID NO 93
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 93

Tyr Ile Val Lys Lys Asn Asp Ser Ile Ser Ser Ile Ala Ser Ala Tyr
  1               5                  10                  15

Asn Val Pro Lys Val Asp Ile Leu Asp Ser Asn Asn Leu Asp Asn Glu
             20                  25                  30

Val Leu Phe Leu Gly Gln Lys Leu Phe Ile Pro
         35                  40

<210> SEQ ID NO 94
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 94

Tyr Lys Val Val Lys Gly Asp Thr Leu Phe Ser Ile Ala Ile Lys Tyr
  1               5                  10                  15

Lys Val Lys Val Ser Asp Leu Lys Arg Ile Asn Lys Leu Asn Val Asp
             20                  25                  30

Asn Ile Lys Ala Gly Gln Ile Leu Ile Ile Pro
         35                  40
```

<210> SEQ ID NO 95
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 95

Tyr Thr Ala Lys Glu Gly Asp Thr Ile Glu Ser Ile Ser Lys Leu Val
 1               5                  10                  15

Gly Leu Ser Gln Glu Glu Ile Ile Ala Trp Asn Asp Leu Arg Ser Lys
            20                  25                  30

Asp Leu Lys Val Gly Met Lys Leu Val Leu Thr
        35                  40

<210> SEQ ID NO 96
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 96

Tyr Met Val Arg Lys Gly Asp Ser Leu Ser Lys Leu Ser Gln Asp Phe
 1               5                  10                  15

Asp Ile Ser Ser Lys Asp Ile Leu Lys Phe Asn Phe Leu Asn Asp Asp
            20                  25                  30

Lys Leu Lys Ile Gly Gln Gln Leu Phe Leu Lys
        35                  40

<210> SEQ ID NO 97
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 97

His Tyr Val Lys Arg Gly Glu Thr Leu Gly Arg Ile Ala Tyr Ile Tyr
 1               5                  10                  15

Gly Val Thr Ala Lys Asp Leu Val Ala Leu Asn Gly Asn Arg Ala Ile
            20                  25                  30

Asn Leu Lys Ala Gly Ser Leu Leu Asn Val Leu
        35                  40

<210> SEQ ID NO 98
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 98

His Ser Val Ala Val Gly Glu Thr Leu Tyr Ser Ile Ala Arg His Tyr
 1               5                  10                  15

-continued

```
Gly Val Leu Ile Glu Asp Leu Lys Asn Trp Asn Asn Leu Ser Ser Asn
            20                  25                  30

Asn Ile Met His Asp Gln Lys Leu Lys Ile Phe
            35                  40
```

<210> SEQ ID NO 99
<211> LENGTH: 43
<212> TYPE: PRT
<213> ORGANISM: Borrelia burgdorferi
<220> FEATURE:
<221> NAME/KEY: SITE
<222> LOCATION: (1)..(43)
<223> OTHER INFORMATION: AcmA cell wall binding domain homologue

<400> SEQUENCE: 99

```
Tyr Lys Val Lys Lys Gly Asp Thr Phe Phe Lys Ile Ala Asn Lys Ile
 1               5                  10                  15

Asn Gly Trp Gln Ser Gly Ile Ala Thr Ile Asn Leu Leu Asp Ser Pro
            20                  25                  30

Ala Val Ser Val Gly Gln Glu Ile Leu Ile Pro
            35                  40
```

<210> SEQ ID NO 100
<211> LENGTH: 44
<212> TYPE: PRT
<213> ORGANISM: Lactobacillus
<220> FEATURE:
<221> NAME/KEY: SITE
<222> LOCATION: (1)..(44)
<223> OTHER INFORMATION: AcmA cell wall binding domain homologue

<400> SEQUENCE: 100

```
Tyr Thr Val Val Ser Gly Asp Ser Trp Trp Lys Ile Ala Gln Arg Asn
 1               5                  10                  15

Gly Leu Ser Met Tyr Thr Leu Ala Ser Gln Asn Gly Lys Ser Ile Tyr
            20                  25                  30

Ser Thr Ile Tyr Pro Gly Asn Lys Leu Ile Ile Lys
            35                  40
```

<210> SEQ ID NO 101
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 101

```
Ile Lys Val Lys Lys Gly Asp Thr Leu Trp Asp Leu Ser Arg Lys Tyr
 1               5                  10                  15

Asp Thr Thr Ile Ser Lys Ile Lys Ser Glu Asn His Leu Arg Ser Asp
            20                  25                  30

Ile Ile Tyr Val Gly Gln Thr Leu Ser Ile Asn
            35                  40
```

<210> SEQ ID NO 102
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue -continued

```
<400> SEQUENCE: 102

Tyr Lys Val Lys Ser Gly Asp Ser Leu Trp Lys Ile Ser Lys Lys Tyr
 1               5                  10                  15

Gly Met Thr Ile Asn Glu Leu Lys Lys Leu Asn Gly Leu Lys Ser Asp
             20                  25                  30

Leu Leu Arg Val Gly Gln Val Leu Lys Leu Lys
         35                  40

<210> SEQ ID NO 103
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 103

Tyr Lys Val Lys Ser Gly Asp Ser Leu Ser Lys Ile Ala Ser Lys Tyr
 1               5                  10                  15

Gly Thr Thr Val Ser Lys Leu Lys Ser Leu Asn Gly Leu Lys Ser Asp
             20                  25                  30

Val Ile Tyr Val Asn Gln Val Leu Lys Val Lys
         35                  40

<210> SEQ ID NO 104
<211> LENGTH: 44
<212> TYPE: PRT
<213> ORGANISM: Bacillus subtilis
<220> FEATURE:
<221> NAME/KEY: SITE
<222> LOCATION: (1)..(44)
<223> OTHER INFORMATION: AcmA cell wall binding domain homologue

<400> SEQUENCE: 104

Cys Ile Val Gln Gln Glu Asp Thr Ile Glu Arg Leu Cys Glu Arg Tyr
 1               5                  10                  15

Glu Ile Thr Ser Gln Gln Leu Ile Arg Met Asn Ser Leu Ala Leu Asp
             20                  25                  30

Asp Glu Leu Lys Ala Gly Gln Ile Leu Tyr Ile Pro
         35                  40

<210> SEQ ID NO 105
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 105

Met Val Lys Gln Gly Asp Thr Leu Ser Ala Ile Ala Ser Gln Tyr Arg
 1               5                  10                  15

Thr Thr Thr Asn Asp Ile Thr Thr Asn Glu Ile Pro Asn Pro Asp
             20                  25                  30

Ser Leu Val Val Gly Gln Thr Ile Val Ile Pro
         35                  40

<210> SEQ ID NO 106
<211> LENGTH: 44
<212> TYPE: PRT
<213> ORGANISM: Bacillus subtilis
```

```
<220> FEATURE:
<221> NAME/KEY: SITE
<222> LOCATION: (1)..(44)
<223> OTHER INFORMATION: AcmA cell wall binding domain homologue

<400> SEQUENCE: 106

Tyr Asp Val Lys Arg Gly Asp Thr Leu Thr Ser Ile Ala Arg Gln Phe
 1               5                  10                  15

Asn Thr Thr Ala Ala Glu Leu Ala Arg Val Asn Arg Ile Gln Leu Asn
             20                  25                  30

Thr Val Leu Gln Ile Gly Phe Arg Leu Tyr Ile Pro
         35                  40

<210> SEQ ID NO 107
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 107

Ile Lys Val Lys Ser Gly Asp Ser Leu Trp Lys Leu Ala Gln Thr Tyr
 1               5                  10                  15

Asn Thr Ser Val Ala Ala Leu Thr Ser Ala Asn His Leu Ser Thr Thr
             20                  25                  30

Val Leu Ser Ile Gly Gln Thr Leu Thr Ile Pro
         35                  40

<210> SEQ ID NO 108
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 108

Tyr Thr Val Lys Ser Gly Asp Ser Leu Trp Leu Ile Ala Asn Glu Phe
 1               5                  10                  15

Lys Met Thr Val Gln Glu Leu Lys Lys Leu Asn Gly Leu Ser Ser Asp
             20                  25                  30

Leu Ile Arg Ala Gly Gln Lys Leu Lys Val Ser
         35                  40

<210> SEQ ID NO 109
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 109

Tyr Lys Val Gln Leu Gly Asp Ser Leu Trp Lys Ile Ala Asn Lys Val
 1               5                  10                  15

Asn Met Ser Ile Ala Glu Leu Lys Val Leu Asn Asn Leu Lys Ser Asp
             20                  25                  30

Thr Ile Tyr Val Asn Gln Val Leu Lys Thr Lys
         35                  40
```

<210> SEQ ID NO 110
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 110

Tyr Thr Val Lys Ser Gly Asp Ser Leu Trp Lys Ile Ala Asn Asn Tyr
 1               5                  10                  15

Asn Leu Thr Val Gln Gln Ile Arg Asn Ile Asn Asn Leu Lys Ser Asp
            20                  25                  30

Val Leu Tyr Val Gly Gln Val Leu Lys Leu Thr
        35                  40

<210> SEQ ID NO 111
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 111

Tyr Thr Val Lys Ser Gly Asp Ser Leu Trp Val Ile Ala Gln Lys Phe
 1               5                  10                  15

Asn Val Thr Ala Gln Gln Ile Arg Glu Lys Asn Asn Leu Lys Thr Asp
            20                  25                  30

Val Leu Gly Val Gly Gln Lys Leu Val Ile Ser
        35                  40

<210> SEQ ID NO 112
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 112

Ile Lys Val Lys Ser Gly Asp Ser Leu Trp Lys Leu Ser Arg Gln Tyr
 1               5                  10                  15

Asp Thr Thr Ile Ser Ala Leu Lys Ser Glu Asn Lys Leu Lys Ser Thr
            20                  25                  30

Val Leu Tyr Val Gly Gln Ser Leu Lys Val Pro
        35                  40

<210> SEQ ID NO 113
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 113

Tyr Thr Val Ala Tyr Gly Asp Ser Leu Trp Met Ile Ala Lys Asn His
 1               5                  10                  15

Lys Met Ser Val Ser Glu Leu Lys Ser Leu Asn Ser Leu Ser Ser Asp

```
                    20                  25                  30

Leu Ile Arg Pro Gly Gln Lys Leu Lys Ile Lys
            35                  40

<210> SEQ ID NO 114
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 114

Tyr Thr Val Lys Leu Gly Asp Ser Leu Trp Lys Ile Ala Asn Ser Leu
 1               5                  10                  15

Asn Met Thr Val Ala Glu Leu Lys Thr Leu Asn Gly Leu Thr Ser Asp
                20                  25                  30

Thr Leu Tyr Pro Lys Gln Val Leu Lys Ile Gly
            35                  40

<210> SEQ ID NO 115
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 115

Tyr Lys Val Lys Ala Gly Asp Ser Leu Trp Lys Ile Ala Asn Arg Leu
 1               5                  10                  15

Gly Val Thr Val Gln Ser Ile Arg Asp Lys Asn Asn Leu Ser Ser Asp
                20                  25                  30

Val Leu Gln Ile Gly Gln Val Leu Thr Ile Ser
            35                  40

<210> SEQ ID NO 116
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 116

Ile Thr Val Gln Lys Gly Asp Thr Leu Trp Gly Ile Ser Gln Lys Asn
 1               5                  10                  15

Gly Val Asn Leu Lys Asp Leu Lys Glu Trp Asn Lys Leu Thr Ser Asp
                20                  25                  30

Lys Ile Ile Ala Gly Glu Lys Leu Thr Ile Ser
            35                  40

<210> SEQ ID NO 117
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 117
```

-continued

Tyr Thr Ile Lys Ala Gly Asp Thr Leu Ser Lys Ile Ala Gln Lys Phe
 1               5                   10                  15

Gly Thr Thr Val Asn Asn Leu Lys Val Trp Asn Asn Leu Ser Ser Asp
                20                  25                  30

Met Ile Tyr Ala Gly Ser Thr Leu Ser Val Lys
            35                  40

<210> SEQ ID NO 118
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 118

His His Val Thr Pro Gly Glu Thr Leu Ser Ile Ile Ala Ser Lys Tyr
 1               5                   10                  15

Asn Val Ser Leu Gln Gln Leu Met Glu Leu Asn His Phe Lys Ser Asp
                20                  25                  30

Gln Ile Tyr Ala Gly Gln Ile Ile Lys Ile Arg
            35                  40

<210> SEQ ID NO 119
<211> LENGTH: 44
<212> TYPE: PRT
<213> ORGANISM: Bacillus subtilis
<220> FEATURE:
<221> NAME/KEY: SITE
<222> LOCATION: (1)..(44)
<223> OTHER INFORMATION: AcmA cell wall binding domain homologue

<400> SEQUENCE: 119

Tyr His Val Lys Lys Gly Asp Thr Leu Ser Gly Ile Ala Ala Ser His
 1               5                   10                  15

Gly Ala Ser Val Lys Thr Leu Gln Ser Ile Asn His Ile Thr Asp Pro
                20                  25                  30

Asn His Ile Lys Ile Gly Gln Val Ile Lys Leu Pro
            35                  40

<210> SEQ ID NO 120
<211> LENGTH: 45
<212> TYPE: PRT
<213> ORGANISM: Bacillus subtilis
<220> FEATURE:
<221> NAME/KEY: SITE
<222> LOCATION: (1)..(45)
<223> OTHER INFORMATION: AcmA cell wall binding domain homologue

<400> SEQUENCE: 120

His Ile Val Gln Lys Gly Asp Ser Leu Trp Lys Ile Ala Glu Lys Tyr
 1               5                   10                  15

Gly Val Asp Val Glu Glu Val Lys Lys Leu Asn Thr Gln Leu Ser Asn
                20                  25                  30

Pro Asp Leu Ile Met Pro Gly Met Lys Ile Lys Val Pro
            35                  40                  45

<210> SEQ ID NO 121
<211> LENGTH: 43
<212> TYPE: PRT
<213> ORGANISM: Bacillus subtilis
<220> FEATURE:

```
<221> NAME/KEY: SITE
<222> LOCATION: (1)..(43)
<223> OTHER INFORMATION: AcmA cell wall binding domain homologue

<400> SEQUENCE: 121

His Ile Val Gly Pro Gly Asp Ser Leu Phe Ser Ile Gly Arg Arg Tyr
 1               5                  10                  15

Gly Ala Ser Val Asp Gln Ile Arg Gly Val Asn Gly Leu Asp Glu Thr
             20                  25                  30

Asn Ile Val Pro Gly Gln Ala Leu Leu Ile Pro
         35                  40

<210> SEQ ID NO 122
<211> LENGTH: 43
<212> TYPE: PRT
<213> ORGANISM: Bacillus subtilis
<220> FEATURE:
<221> NAME/KEY: SITE
<222> LOCATION: (1)..(43)
<223> OTHER INFORMATION: AcmA cell wall binding domain homologue

<400> SEQUENCE: 122

Tyr Gln Val Lys Gln Gly Asp Thr Leu Asn Ser Ile Ala Ala Asp Phe
 1               5                  10                  15

Arg Ile Ser Thr Ala Ala Leu Leu Gln Ala Asn Pro Ser Leu Gln Ala
             20                  25                  30

Gly Leu Thr Ala Gly Gln Ser Ile Val Ile Pro
         35                  40

<210> SEQ ID NO 123
<211> LENGTH: 44
<212> TYPE: PRT
<213> ORGANISM: Bacillus subtilis phage PBSX
<220> FEATURE:
<221> NAME/KEY: SITE
<222> LOCATION: (1)..(44)
<223> OTHER INFORMATION: AcmA cell wall binding domain homologue

<400> SEQUENCE: 123

Tyr Val Val Lys Gln Gly Asp Thr Leu Thr Ser Ile Ala Arg Ala Phe
 1               5                  10                  15

Gly Val Thr Val Ala Gln Leu Gln Glu Trp Asn Asn Ile Glu Asp Pro
             20                  25                  30

Asn Leu Ile Arg Val Gly Gln Val Leu Ile Val Ser
         35                  40

<210> SEQ ID NO 124
<211> LENGTH: 45
<212> TYPE: PRT
<213> ORGANISM: Bacillus subtilis phage PZA
<220> FEATURE:
<221> NAME/KEY: SITE
<222> LOCATION: (1)..(45)
<223> OTHER INFORMATION: AcmA cell wall binding domain homologue

<400> SEQUENCE: 124

Tyr Lys Val Lys Ser Gly Asp Asn Leu Thr Lys Ile Ala Lys Lys His
 1               5                  10                  15

Asn Thr Thr Val Ala Thr Leu Leu Lys Leu Asn Pro Ser Ile Lys Asp
             20                  25                  30

Pro Asn Met Ile Arg Val Gly Gln Thr Ile Asn Val Thr
         35                  40                  45
```

-continued

```
<210> SEQ ID NO 125
<211> LENGTH: 45
<212> TYPE: PRT
<213> ORGANISM: Bacillus subtilis phage PZA
<220> FEATURE:
<221> NAME/KEY: SITE
<222> LOCATION: (1)..(45)
<223> OTHER INFORMATION: AcmA cell wall binding domain homologue

<400> SEQUENCE: 125

His Lys Val Lys Ser Gly Asp Thr Leu Ser Lys Ile Ala Val Asp Asn
  1               5                  10                  15

Lys Thr Thr Val Ser Arg Leu Met Ser Leu Asn Pro Glu Ile Thr Asn
             20                  25                  30

Pro Asn His Ile Lys Val Gly Gln Thr Ile Arg Leu Ser
         35                  40                  45

<210> SEQ ID NO 126
<211> LENGTH: 45
<212> TYPE: PRT
<213> ORGANISM: Bacillus subtilis phage B103
<220> FEATURE:
<221> NAME/KEY: SITE
<222> LOCATION: (1)..(45)
<223> OTHER INFORMATION: AcmA cell wall binding domain homologue

<400> SEQUENCE: 126

His Val Val Lys Lys Gly Asp Thr Leu Ser Glu Ile Ala Lys Lys Ile
  1               5                  10                  15

Lys Thr Ser Thr Lys Thr Leu Leu Glu Leu Asn Pro Thr Ile Lys Asn
             20                  25                  30

Pro Asn Lys Ile Tyr Val Gly Gln Arg Ile Asn Val Gly
         35                  40                  45

<210> SEQ ID NO 127
<211> LENGTH: 45
<212> TYPE: PRT
<213> ORGANISM: Bacillus subtilis phage B103
<220> FEATURE:
<221> NAME/KEY: SITE
<222> LOCATION: (1)..(45)
<223> OTHER INFORMATION: AcmA cell wall binding domain homologue

<400> SEQUENCE: 127

Tyr Lys Ile Lys Arg Gly Glu Thr Leu Thr Gly Ile Ala Lys Lys Asn
  1               5                  10                  15

Lys Thr Thr Val Ser Gln Leu Met Lys Leu Asn Pro Asn Ile Lys Asn
             20                  25                  30

Ala Asn Asn Ile Tyr Ala Gly Gln Thr Ile Arg Leu Lys
         35                  40                  45

<210> SEQ ID NO 128
<211> LENGTH: 44
<212> TYPE: PRT
<213> ORGANISM: Bacillus sphaericus
<220> FEATURE:
<221> NAME/KEY: SITE
<222> LOCATION: (1)..(44)
<223> OTHER INFORMATION: AcmA cell wall binding domain homologue

<400> SEQUENCE: 128

Ile Leu Ile Arg Pro Gly Asp Ser Leu Trp Tyr Phe Ser Asp Leu Phe
  1               5                  10                  15

Lys Ile Pro Leu Gln Leu Leu Leu Asp Ser Asn Arg Asn Ile Asn Pro
             20                  25                  30
```

```
Gln Leu Leu Gln Val Gly Gln Arg Ile Gln Ile Pro
        35                  40
```

<210> SEQ ID NO 129
<211> LENGTH: 44
<212> TYPE: PRT
<213> ORGANISM: Bacillus sphaericus
<220> FEATURE:
<221> NAME/KEY: SITE
<222> LOCATION: (1)..(44)
<223> OTHER INFORMATION: AcmA cell wall binding domain homologue

<400> SEQUENCE: 129

```
Tyr Thr Ile Thr Gln Gly Asp Ser Leu Trp Gln Ile Ala Gln Asn Lys
 1               5                  10                  15

Asn Leu Pro Leu Asn Ala Ile Leu Leu Val Asn Pro Glu Ile Gln Pro
            20                  25                  30

Ser Arg Leu His Ile Gly Gln Thr Ile Gln Val Pro
        35                  40
```

<210> SEQ ID NO 130
<211> LENGTH: 44
<212> TYPE: PRT
<213> ORGANISM: Salmonella dublin
<220> FEATURE:
<221> NAME/KEY: SITE
<222> LOCATION: (1)..(44)
<223> OTHER INFORMATION: AcmA cell wall binding domain homologue

<400> SEQUENCE: 130

```
Tyr Thr Val Lys Lys Gly Asp Thr Leu Phe Tyr Ile Ala Trp Ile Thr
 1               5                  10                  15

Gly Asn Asp Phe Arg Asp Leu Ala Gln Arg Asn Ser Ile Ser Ala Pro
            20                  25                  30

Tyr Ser Leu Asn Val Gly Gln Thr Leu Gln Val Gly
        35                  40
```

<210> SEQ ID NO 131
<211> LENGTH: 45
<212> TYPE: PRT
<213> ORGANISM: Escherichia coli
<220> FEATURE:
<221> NAME/KEY: SITE
<222> LOCATION: (1)..(45)
<223> OTHER INFORMATION: AcmA cell wall binding domain homologue

<400> SEQUENCE: 131

```
Tyr Val Val Ser Thr Gly Asp Thr Leu Ser Ser Ile Leu Asn Gln Tyr
 1               5                  10                  15

Gly Ile Asp Met Gly Asp Ile Ser Gln Leu Ala Ala Ala Asp Lys Glu
            20                  25                  30

Leu Arg Asn Leu Lys Ile Gly Gln Gln Leu Ser Trp Thr
        35                  40                  45
```

<210> SEQ ID NO 132
<211> LENGTH: 43
<212> TYPE: PRT
<213> ORGANISM: Escherichia coli
<220> FEATURE:
<221> NAME/KEY: SITE
<222> LOCATION: (1)..(43)
<223> OTHER INFORMATION: AcmA cell wall binding domain homologue

<400> SEQUENCE: 132

-continued

Tyr Thr Val Arg Ser Gly Asp Thr Leu Ser Ser Ile Ala Ser Arg Leu
 1               5                  10                  15

Gly Val Ser Thr Lys Asp Leu Gln Gln Trp Asn Lys Leu Arg Gly Ser
             20                  25                  30

Lys Leu Lys Pro Gly Gln Ser Leu Thr Ile Gly
         35                  40

<210> SEQ ID NO 133
<211> LENGTH: 42
<212> TYPE: PRT
<213> ORGANISM: Escherichia coli
<220> FEATURE:
<221> NAME/KEY: SITE
<222> LOCATION: (1)..(42)
<223> OTHER INFORMATION: AcmA cell wall binding domain homologue

<400> SEQUENCE: 133

Tyr Arg Val Arg Lys Gly Asp Ser Leu Ser Ser Ile Ala Lys Arg His
 1               5                  10                  15

Gly Val Asn Ile Lys Asp Val Met Arg Trp Asn Ser Asp Thr Ala Asn
             20                  25                  30

Leu Gln Pro Gly Asp Lys Leu Thr Leu Phe
         35                  40

<210> SEQ ID NO 134
<211> LENGTH: 44
<212> TYPE: PRT
<213> ORGANISM: Escherichia coli
<220> FEATURE:
<221> NAME/KEY: SITE
<222> LOCATION: (1)..(44)
<223> OTHER INFORMATION: AcmA cell wall binding domain homologue

<400> SEQUENCE: 134

Tyr Thr Val Lys Arg Gly Asp Thr Leu Tyr Arg Ile Ser Arg Thr Thr
 1               5                  10                  15

Gly Thr Ser Val Lys Glu Leu Ala Arg Leu Asn Gly Ile Ser Pro Pro
             20                  25                  30

Tyr Thr Ile Glu Val Gly Gln Lys Leu Lys Leu Gly
         35                  40

<210> SEQ ID NO 135
<211> LENGTH: 44
<212> TYPE: PRT
<213> ORGANISM: Staphylococcus
<220> FEATURE:
<221> NAME/KEY: SITE
<222> LOCATION: (1)..(44)
<223> OTHER INFORMATION: AcmA cell wall binding domain homologue

<400> SEQUENCE: 135

Tyr Thr Val Lys Lys Gly Asp Thr Leu Phe Tyr Ile Ala Trp Ile Thr
 1               5                  10                  15

Gly Asn Asp Phe Arg Asp Leu Ala Gln Arg Asn Asn Ile Gln Ala Pro
             20                  25                  30

Tyr Ala Leu Asn Val Gly Gln Thr Leu Gln Val Gly
         35                  40

<210> SEQ ID NO 136
<211> LENGTH: 43
<212> TYPE: PRT
<213> ORGANISM: Drosophila melanogaster
<220> FEATURE:
<221> NAME/KEY: SITE

```
<222> LOCATION: (1)..(43)
<223> OTHER INFORMATION: AcmA cell wall binding domain homologue

<400> SEQUENCE: 136

Tyr Thr Val Gly Asn Arg Asp Thr Leu Thr Ser Val Ala Ala Arg Phe
 1               5                  10                  15

Asp Thr Thr Pro Ser Glu Leu Thr His Leu Asn Arg Leu Asn Ser Ser
            20                  25                  30

Phe Ile Tyr Pro Gly Gln Gln Leu Leu Val Pro
        35                  40

<210> SEQ ID NO 137
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 137

Arg Lys Val Lys Asn Gly Asp Thr Leu Asn Lys Leu Ala Ile Lys Tyr
 1               5                  10                  15

Gln Val Asn Val Ala Glu Ile Lys Arg Val Asn Asn Met Val Ser Glu
            20                  25                  30

Gln Asp Phe Met Ala Leu Ser Lys Val Lys Ile Pro
        35                  40

<210> SEQ ID NO 138
<211> LENGTH: 43
<212> TYPE: PRT
<213> ORGANISM: Caenorhabditis elegans
<220> FEATURE:
<221> NAME/KEY: SITE
<222> LOCATION: (1)..(43)
<223> OTHER INFORMATION: AcmA cell wall binding domain homologue

<400> SEQUENCE: 138

Tyr Thr Ile Thr Glu Thr Asp Thr Leu Glu Arg Val Ala Ala Ser His
 1               5                  10                  15

Asp Cys Thr Val Gly Glu Leu Met Lys Leu Asn Lys Met Ala Ser Arg
            20                  25                  30

Met Val Phe Pro Gly Gln Lys Ile Leu Val Pro
        35                  40

<210> SEQ ID NO 139
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 139

Thr Glu Ile Lys Ser Gly Asp Ser Cys Trp Asn Ile Ala Ser Asn Ala
 1               5                  10                  15

Lys Ile Ser Val Glu Arg Leu Gln Gln Leu Asn Lys Gly Met Lys Cys
            20                  25                  30

Asp Lys Leu Pro Leu Gly Asp Lys Leu Cys Leu Ala
        35                  40

<210> SEQ ID NO 140
```

```
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 140
```

Leu Lys Leu Lys Ala Glu Asp Thr Cys Phe Lys Ile Trp Ser Ser Gln
 1               5                  10                  15

Lys Leu Ser Glu Arg Gln Phe Leu Gly Met Asn Glu Gly Met Asp Cys
            20                  25                  30

Asp Lys Leu Lys Val Gly Lys Glu Val Cys Val Ala
        35                  40

```
<210> SEQ ID NO 141
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 141
```

His Lys Ile Gln Lys Gly Asp Thr Cys Phe Lys Ile Trp Thr Thr Asn
 1               5                  10                  15

Lys Ile Ser Glu Lys Gln Phe Arg Asn Leu Asn Lys Gly Leu Asp Cys
            20                  25                  30

Asp Lys Leu Glu Ile Gly Lys Glu Val Cys Ile Ser
        35                  40

```
<210> SEQ ID NO 142
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 142
```

Leu Lys Ile Lys Glu Gly Asp Thr Cys Tyr Asn Ile Trp Thr Ser Gln
 1               5                  10                  15

Lys Ile Ser Glu Gln Glu Phe Met Glu Leu Asn Lys Gly Leu Asp Cys
            20                  25                  30

Asp Lys Leu Glu Ile Gly Lys Glu Val Cys Val Thr
        35                  40

```
<210> SEQ ID NO 143
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 143
```

Tyr Arg Phe Lys Lys Gly Asp Thr Cys Tyr Lys Ile Trp Thr Ser His
 1               5                  10                  15

Lys Met Ser Glu Lys Gln Phe Arg Ala Leu Asn Arg Gly Ile Asp Cys
            20                  25                  30

Asp Arg Leu Val Pro Gly Lys Glu Leu Cys Val Gly
         35                  40

<210> SEQ ID NO 144
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 144

Ile Thr Val Lys Pro Gly Asp Thr Cys Phe Ser Ile Trp Thr Ser Gln
1               5                   10                  15

Lys Met Thr Gln Gln Gln Phe Met Asp Ile Asn Pro Glu Leu Asp Cys
            20                  25                  30

Asp Lys Leu Glu Ile Gly Lys Glu Val Cys Val Thr
         35                  40

<210> SEQ ID NO 145
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 145

Val Lys Ile Asn Pro Gly Asp Thr Cys Phe Asn Ile Trp Thr Ser Gln
1               5                   10                  15

Arg Met Thr Gln Gln Gln Phe Met Asp Leu Asn Lys Arg Leu Asp Cys
            20                  25                  30

Asp Lys Leu Glu Val Gly Lys Glu Val Cys Val Thr
         35                  40

<210> SEQ ID NO 146
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 146

Val Gln Ile Asn Pro Gly Asp Thr Cys Phe Lys Ile Trp Ser Ala Gln
1               5                   10                  15

Lys Leu Thr Glu Gln Gln Phe Met Glu Leu Asn Lys Gly Leu Asp Cys
            20                  25                  30

Asp Arg Leu Glu Val Gly Lys Glu Val Cys Ile Ala
         35                  40

<210> SEQ ID NO 147
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 147

Thr Glu Val Lys Glu Gly Asp Thr Cys Phe Lys Ile Trp Ser Ala His

```
                1               5              10              15

Lys Ile Thr Glu Gln Gln Phe Met Glu Met Asn Arg Gly Leu Asp Cys
                   20                  25                  30

Asn Arg Leu Glu Val Gly Lys Glu Val Cys Ile Val
        35                  40
```

<210> SEQ ID NO 148
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 148

```
Ile Lys Val Lys Glu Gly Asp Thr Cys Phe Lys Ile Trp Ser Ala Gln
 1               5                  10                  15

Lys Met Thr Glu Gln Gln Phe Met Glu Met Asn Arg Gly Leu Asp Cys
                    20                  25                  30

Asn Lys Leu Met Val Gly Lys Glu Val Cys Val Ser
        35                  40
```

<210> SEQ ID NO 149
<211> LENGTH: 41
<212> TYPE: PRT
<213> ORGANISM: Caenorhabditis elegans
<220> FEATURE:
<221> NAME/KEY: SITE
<222> LOCATION: (1)..(41)
<223> OTHER INFORMATION: AcmA cell wall binding domain homologue

<400> SEQUENCE: 149

```
Ala Thr Ile Thr Pro Gly Asn Thr Cys Phe Asn Ile Ser Val Ala Tyr
 1               5                  10                  15

Gly Ile Asn Leu Thr Asp Leu Gln Lys Thr Tyr Asp Cys Lys Ala Leu
                    20                  25                  30

Glu Val Gly Asp Thr Ile Cys Val Ser
        35                  40
```

<210> SEQ ID NO 150
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 150

```
Ile Glu Val Ile Lys Gly Asp Thr Cys Trp Phe Leu Glu Asn Ala Phe
 1               5                  10                  15

Lys Thr Asn Gln Thr Glu Met Glu Arg Ala Asn Glu Gly Val Lys Cys
                    20                  25                  30

Asp Asn Leu Pro Ile Gly Arg Met Met Cys Val Trp
        35                  40
```

<210> SEQ ID NO 151
<211> LENGTH: 44
<212> TYPE: PRT
<213> ORGANISM: Caenorhabditis elegans
<220> FEATURE:
<221> NAME/KEY: SITE
<222> LOCATION: (1)..(44)

<223> OTHER INFORMATION: AcmA cell wall binding domain homologue

<400> SEQUENCE: 151

His Thr Ile Lys Ser Gly Asp Thr Cys Trp Lys Ile Ala Ser Glu Ala
1               5                   10                  15

Ser Ile Ser Val Gln Glu Leu Glu Gly Leu Asn Ser Lys Lys Ser Cys
            20                  25                  30

Ala Asn Leu Ala Val Gly Leu Ser Glu Gln Glu Phe
        35                  40

<210> SEQ ID NO 152
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 152

Ile His Val Lys Glu Gly Asp Thr Cys Tyr Thr Ile Trp Thr Ser Gln
1               5                   10                  15

His Leu Thr Glu Lys Gln Phe Met Asp Met Asn Glu Glu Leu Asn Cys
            20                  25                  30

Gly Met Leu Glu Ile Gly Asn Glu Val Cys Val Asp
        35                  40

<210> SEQ ID NO 153
<211> LENGTH: 41
<212> TYPE: PRT
<213> ORGANISM: Caenorhabditis elegans
<220> FEATURE:
<221> NAME/KEY: SITE
<222> LOCATION: (1)..(41)
<223> OTHER INFORMATION: AcmA cell wall binding domain homologue

<400> SEQUENCE: 153

Ala Thr Val Thr Pro Gly Ser Ser Cys Tyr Thr Ile Ser Ala Ser Tyr
1               5                   10                  15

Gly Leu Asn Leu Ala Glu Leu Gln Thr Thr Tyr Asn Cys Asp Ala Leu
            20                  25                  30

Gln Val Asp Asp Thr Ile Cys Val Ser
        35                  40

<210> SEQ ID NO 154
<211> LENGTH: 44
<212> TYPE: PRT
<213> ORGANISM: Caenorhabditis elegans
<220> FEATURE:
<221> NAME/KEY: SITE
<222> LOCATION: (1)..(44)
<223> OTHER INFORMATION: AcmA cell wall binding domain homologue

<400> SEQUENCE: 154

Ile Glu Ile Leu Asn Gly Asp Thr Cys Gly Phe Leu Glu Asn Ala Phe
1               5                   10                  15

Gln Thr Asn Asn Thr Glu Met Glu Ile Ala Asn Glu Gly Val Lys Cys
            20                  25                  30

Asp Asn Leu Pro Ile Gly Arg Met Met Cys Val Trp
        35                  40

<210> SEQ ID NO 155
<211> LENGTH: 46

```
<212> TYPE: PRT
<213> ORGANISM: Bacillus subtilis
<220> FEATURE:
<221> NAME/KEY: SITE
<222> LOCATION: (1)..(46)
<223> OTHER INFORMATION: AcmA cell wall binding domain homologue

<400> SEQUENCE: 155

His Thr Val Gln Lys Lys Glu Thr Leu Tyr Arg Ile Ser Met Lys Tyr
 1               5                  10                  15

Tyr Lys Ser Arg Thr Gly Glu Glu Lys Ile Arg Ala Tyr Asn His Leu
            20                  25                  30

Asn Gly Asn Asp Val Tyr Thr Gly Gln Val Leu Asp Ile Pro
        35                  40                  45

<210> SEQ ID NO 156
<211> LENGTH: 49
<212> TYPE: PRT
<213> ORGANISM: Citrobacter freundii
<220> FEATURE:
<221> NAME/KEY: SITE
<222> LOCATION: (1)..(49)
<223> OTHER INFORMATION: AcmA cell wall binding domain homologue

<400> SEQUENCE: 156

Tyr Thr Leu Lys Thr Gly Glu Ser Val Ala Gln Leu Ser Lys Ser Gln
 1               5                  10                  15

Gly Ile Ser Val Pro Val Ile Trp Ser Leu Asn Lys His Leu Tyr Ser
            20                  25                  30

Ser Glu Ser Glu Met Met Lys Ala Ser Pro Gly Gln Gln Ile Ile Leu
        35                  40                  45

Pro

<210> SEQ ID NO 157
<211> LENGTH: 49
<212> TYPE: PRT
<213> ORGANISM: Escherichia coli
<220> FEATURE:
<221> NAME/KEY: SITE
<222> LOCATION: (1)..(49)
<223> OTHER INFORMATION: AcmA cell wall binding domain homologue

<400> SEQUENCE: 157

Tyr Thr Leu Lys Thr Gly Glu Thr Val Ala Asp Leu Ser Lys Ser Gln
 1               5                  10                  15

Asp Ile Asn Leu Ser Thr Ile Trp Ser Leu Asn Lys His Leu Tyr Ser
            20                  25                  30

Ser Glu Ser Glu Met Met Lys Ala Ala Pro Gly Gln Gln Ile Ile Leu
        35                  40                  45

Pro

<210> SEQ ID NO 158
<211> LENGTH: 47
<212> TYPE: PRT
<213> ORGANISM: Micrococcus luteus
<220> FEATURE:
<221> NAME/KEY: SITE
<222> LOCATION: (1)..(47)
<223> OTHER INFORMATION: AcmA cell wall binding domain homologue

<400> SEQUENCE: 158

Ile Val Val Lys Ser Gly Asp Ser Leu Trp Thr Leu Ala Asn Glu Tyr
 1               5                  10                  15
```

```
Glu Val Glu Gly Gly Trp Thr Ala Leu Tyr Glu Ala Asn Lys Gly Ala
            20                  25                  30

Val Ser Asp Ala Ala Val Ile Tyr Val Gly Gln Glu Leu Val Leu
            35                  40                  45

<210> SEQ ID NO 159
<211> LENGTH: 51
<212> TYPE: PRT
<213> ORGANISM: Bacillus subtilis
<220> FEATURE:
<221> NAME/KEY: SITE
<222> LOCATION: (1)..(51)
<223> OTHER INFORMATION: AcmA cell wall binding domain homologue

<400> SEQUENCE: 159

Ile Glu Val Gln Gln Gly Asp Thr Leu Trp Ser Ile Ala Asp Gln Val
  1               5                  10                  15

Ala Asp Thr Lys Lys Ile Asn Lys Asn Asp Phe Ile Glu Trp Val Ala
            20                  25                  30

Asp Lys Asn Gln Leu Gln Thr Ser Asp Ile Gln Pro Gly Asp Glu Leu
            35                  40                  45

Val Ile Pro
        50

<210> SEQ ID NO 160
<211> LENGTH: 55
<212> TYPE: PRT
<213> ORGANISM: Streptococcus pyogenes
<220> FEATURE:
<221> NAME/KEY: SITE
<222> LOCATION: (1)..(55)
<223> OTHER INFORMATION: AcmA cell wall binding domain homologue

<400> SEQUENCE: 160

Tyr Thr Val Lys Tyr Gly Asp Thr Leu Ser Thr Ile Ala Glu Ala Met
  1               5                  10                  15

Gly Ile Asp Val His Val Leu Gly Asp Ile Asn His Ile Ala Asn Ile
            20                  25                  30

Asp Leu Ile Phe Pro Asp Thr Ile Leu Thr Ala Asn Tyr Asn Gln His
            35                  40                  45

Gly Gln Ala Thr Thr Leu Thr
        50                  55

<210> SEQ ID NO 161
<211> LENGTH: 57
<212> TYPE: PRT
<213> ORGANISM: Bacillus subtilis
<220> FEATURE:
<221> NAME/KEY: SITE
<222> LOCATION: (1)..(57)
<223> OTHER INFORMATION: AcmA cell wall binding domain homologue

<400> SEQUENCE: 161

Tyr Thr Val Lys Lys Gly Asp Thr Leu Trp Asp Ile Ala Gly Arg Phe
  1               5                  10                  15

Tyr Gly Asn Ser Thr Gln Trp Arg Lys Ile Trp Asn Ala Asn Lys Thr
            20                  25                  30

Ala Met Ile Lys Arg Ser Lys Arg Asn Ile Arg Gln Pro Gly His Trp
            35                  40                  45

Ile Phe Pro Gly Gln Lys Leu Ile Pro
        50                  55
```

<210> SEQ ID NO 162
<211> LENGTH: 58
<212> TYPE: PRT
<213> ORGANISM: Bacillus subtilis
<220> FEATURE:
<221> NAME/KEY: SITE
<222> LOCATION: (1)..(58)
<223> OTHER INFORMATION: AcmA cell wall binding domain homologue

<400> SEQUENCE: 162

Tyr Thr Val Lys Lys Gly Asp Thr Leu Trp Asp Leu Ala Gly Lys Phe
 1               5                  10                  15

Tyr Gly Asp Ser Thr Lys Trp Arg Lys Ile Trp Lys Val Asn Lys Lys
                20                  25                  30

Ala Met Ile Lys Arg Ser Lys Arg Asn Ile Arg Gln Pro Gly His Trp
            35                  40                  45

Ile Phe Pro Gly Gln Lys Leu Lys Ile Pro
        50                  55

<210> SEQ ID NO 163
<211> LENGTH: 45
<212> TYPE: PRT
<213> ORGANISM: Lactococcus lactis
<220> FEATURE:
<221> NAME/KEY: SITE
<222> LOCATION: (1)..(45)
<223> OTHER INFORMATION: Consensus repeat, Xaa stands for any amino acid

<400> SEQUENCE: 163

Tyr Xaa Val Lys Xaa Gly Asp Thr Leu Xaa Xaa Ile Ala Xaa Xaa Xaa
 1               5                  10                  15

Xaa Xaa Xaa Xaa Xaa Xaa Leu Xaa Xaa Xaa Asn Xaa Xaa Leu Xaa Xaa
                20                  25                  30

Xaa Xaa Xaa Ile Xaa Xaa Gly Gln Xaa Ile Xaa Val Xaa
            35                  40                  45

<210> SEQ ID NO 164
<211> LENGTH: 45
<212> TYPE: PRT
<213> ORGANISM: Lactococcus lactis
<220> FEATURE:
<221> NAME/KEY: SITE
<222> LOCATION: (1)..(45)
<223> OTHER INFORMATION: Consensus repeat, Xaa stands for any amino acid

<400> SEQUENCE: 164

His Xaa Ile Arg Xaa Xaa Glu Ser Val Xaa Xaa Leu Ser Xaa Xaa Xaa
 1               5                  10                  15

Xaa Xaa Xaa Xaa Xaa Xaa Ile Xaa Xaa Xaa Xaa Xaa Xaa Ile Xaa Xaa
                20                  25                  30

Xaa Xaa Xaa Leu Xaa Xaa Xaa Xaa Xaa Leu Xaa Ile Xaa
            35                  40                  45

<210> SEQ ID NO 165
<211> LENGTH: 45
<212> TYPE: PRT
<213> ORGANISM: Lactococcus lactis
<220> FEATURE:
<221> NAME/KEY: SITE
<222> LOCATION: (1)..(45)
<223> OTHER INFORMATION: Consensus repeat, Xaa stands for any amino acid

<400> SEQUENCE: 165

Xaa Xaa Leu Xaa Xaa Xaa Xaa Xaa Ile Xaa Xaa Val Xaa Xaa Xaa Xaa
 1               5                  10                  15

```
-continued

Xaa Xaa Xaa Xaa Xaa Xaa Xaa Xaa Xaa Xaa Xaa Xaa Xaa Xaa Xaa Xaa
            20                  25                  30

Xaa Xaa Xaa Val Xaa Xaa Xaa Xaa Xaa Val Xaa Leu Xaa
        35                  40              45
```

IMMUNIZATION WITH BACTERIAL GHOST-BASED VACCINES

CROSS-REFERENCE TO RELATED APPLICATIONS

This application is a divisional of application Ser. No. 10/321,857, filed Dec. 16, 2002, now U.S. Pat. No. 7,067,639, which itself is a continuation of International Application Number PCT/NL02/00383 filed on Jun. 11, 2002, designating the United States of America, published in English on Dec. 19, 2002 as PCT International Publication WO 02101026 A2, the contents of the entirety of both which are incorporated by reference.

STATEMENT ACCORDING TO 37 C.F.R. § 1.52(e)(5)-SEQUENCE LISTING SUBMITTED ON COMPACT DISC

Pursuant to 37 C.F.R. § 1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "SeqList-CRF.txt" which is 88 KB and created on Dec. 9, 2005.

TECHNICAL FIELD

The present invention relates generally to biotechnology, and, more particularly, pertains to a method for obtaining cell-wall material of Gram-positive bacteria with an improved capacity for binding a proteinaceous substance comprising an AcmA cell-wall binding domain, as well as pharmaceutical compositions including the obtained cell-wall material.

BACKGROUND

Heterologous surface display of proteins (Stahl and Uhlen, TIBTECH May 1997, 15, 185-192) on recombinant microorganisms via the targeting and anchoring of heterologous proteins to the outer surface or the cell wall of host cells, such as yeast, fungi, mammalian cells, plant cells, and bacteria, has been possible for several years. Display of heterologous proteins at the surface of these cells has taken many forms including the expression of reactive groups such as antigenic determinants, heterologous enzymes, single-chain antibodies, polyhistidyl tags, peptides, and other compounds. Heterologous surface display has been applied as a tool for applied and fundamental research in microbiology, molecular biology, vaccinology and biotechnology. Another application of bacterial surface display has been the development of live-bacterial-vaccine delivery systems. The cell-surface display of heterologous antigenic determinants has been considered advantageous for inducing antigen-specific immune responses in live recombinant cells used for immunization. Another application has been the use of bacterial surface display in generating whole-cell bioadsorbents or biofilters for environmental purposes, microbiocatalysts, and diagnostic tools.

Generally, chimeric proteins include an anchoring or targeting portion that is specific and selective for the recombinant organism, wherein the anchoring portion is combined with the reactive group, such as the antigenic determinant, heterologous enzyme, single-chain antibody, polyhistidyl tag, peptide, or other compound. A well-known anchoring portion comprises the so-called LPXTG (SEQ ID NO:1) box, which covalently binds to a Staphylococcus bacterial surface, i.e., in the form of a fully integrated membrane protein. In this manner, at least two polypeptides of different genetic origins may be joined by a normal peptide bond to produce a chimeric protein. For example, PCT International Patent Publication No. WO 94/18330, which relates to the isolation of compounds from complex mixtures and the preparation of immobilized ligands (bioadsorbents), discloses a method for obtaining a ligand comprising anchoring a binding protein in or at the exterior of a cell wall of a recombinant cell. The binding protein is essentially a chimeric protein produced by the recombinant cell and includes an N-terminal part derived from an antibody that is capable of binding to a specific compound, wherein the N-terminal part is joined to a C-terminal anchoring part, derived from an anchoring protein purposely selected for being functional in the specific recombinant cell chosen. PCT International Patent Publication No. WO 97/08553 discloses a method for selectively targeting proteins to the cell wall of Staphylococcus sp., using anchoring proteins which include long stretches of at least 80-90 amino acid long amino acid cell-wall-targeting signals. The signals are derived from the lysostaphin gene or amidase gene of Staphylococcus and encode for proteins that selectively bind to Staphylococcus cell-wall components.

Vaccine delivery or immunization systems with attenuated bacterial vector strains that express distinct antigenic determinants against a wide variety of diseases are currently being developed. Mucosal vaccines for nasal or oral passages using these attenuated bacterial vectors have received a great deal of attention. For example, both systemic and mucosal antibody responses against an antigenic determinant of hornet venom have been detected in mice orally colonized with a genetically engineered human oral commensal Streptococcus gordonii strain that expresses the hornet venom antigenic determinant on its surface (Medaglini et al., PNAS 1995, 2; 6868-6872). A protective immune response was also elicited by oral delivery of a recombinant bacterial vaccine that included tetanus toxin fragment C constitutively expressed in Lactococcus lactis (Robinson et al., Nature Biotechnology 1997, 15; 653-657). Mucosal immunization is considered an effective means of inducing IgG and secretory IgA antibodies directed against specific pathogens of mucosal surfaces.

Immunogens expressed by bacterial vectors may be presented in a particulate form to antigen-presenting cells, such as M-cells, of the immune system and therefore should be less likely to induce tolerance when compared to soluble antigens. Additionally, the existence of a common mucosal immune system permits immunization of one specific mucosal surface in order to induce secretion of antigen-specific IgA and other specific immune responses at distant mucosal sites. A drawback to using bacterial vectors for immunization is the potential of the bacterial strain causing inflammation or disease and potentially leading to fever or bacteremia. Instead of using attenuated bacterial strains that may become pathogenic, recombinant commensal bacteria, such as Streptococcus sp. or Lactococcus sp., may be used as vaccine carriers.

A potential problem with recombinant commensal microorganisms is that they may colonize the mucosal surfaces and generate a long-term exposure to the target antigens expressed and released by the recombinant microorganisms which may cause immune tolerance.

Additionally, the use of genetically modified microorganisms that contain recombinant nucleic acid has met considerable opposition from the public as a whole, stemming from a low-level acceptance of products which contain recombinant DNA or RNA. Similar objections exist against even the use of attenuated pathogenic strains or against proteins, or parts of proteins, derived from pathogenic strains. Further, the heterologous surface display of proteins described herein entails the use of anchoring or targeting proteins specific and selective for a limited set of microorganisms, which are of recombinant or pathogenic nature which greatly restricts their potential applications.

The protein anchor of *L. lactis*, AcmA (cA), its homologs and functional derivatives (PCT International Patent Publication No. WO99/25836) bind in a non-covalent manner to a wide variety of Gram-positive bacteria. Binding also occurs to isolated cell-wall material. The ligand to which the protein anchor of *L. lactis* binds in these cell walls is currently unknown.

The use of a gram-positive, food-grade bacterium, such as *Lactococcus lactis*, offers significant advantages over the use of other bacteria, such as *Salmonella*, as a vaccine delivery vehicle. For instance, *L. lactis* does not replicate in or invade human tissues and reportedly possesses low intrinsic immunity (Norton et al. 1994). Further, mucosal-delivered *L. lactis* that expresses tetanus toxin fragment C has been shown to induce antibodies that protect mice against a lethal challenge with tetanus toxin even if the carrier bacteria was killed prior to administration (Robinson et al. 1997). The killed bacteria still contain recombinant DNA that will be spread into the environment, especially when used in wide-scale oral immunization programs. However, the uncontrollable shedding of recombinant DNA into the environment may have the risk of being taken up by other bacteria or other microorganisms.

SUMMARY OF THE INVENTION

Disclosed is a method for improving binding of a proteinaceous substance to cell-wall material of a Gram-positive bacterium. The proteinaceous substance comprises at least one repeat, but may comprise two or three repeat sequences of an AcmA cell-wall binding domain, homolog or functional derivative thereof. The method comprises treating the cell-wall material with a solution capable of removing a cell-wall component, such as a protein, lipoteichoic acid or carbohydrate, from the cell-wall material and contacting the proteinaceous substance with the treated cell-wall material. Improved binding may be obtained by treating the cell-wall material with a solution capable of removing a cell-wall component. The cell-wall material may be subsequently stored until it is contacted with a desired fusion protein. The fusion protein may comprise an AcmA cell-wall binding domain, homolog or functional derivative thereof where the cell-wall material is contacted with the fusion protein. The method of the present invention may be used to obtain cell-wall material with an improved capacity for binding a proteinaceous substance comprising the AcmA cell-wall binding domain, homolog or functional derivative thereof.

Also disclosed is a method for removing components from a bacterial cell wall comprising treating whole cells with a solution capable of removing a cell-wall component such as a protein, lipoteichoic acid or carbohydrate from the cell-wall material. The cell-wall material obtained by the present invention yields cell-wall material with at least 20%, better 30%, best 40% or even 50% of relatively empty, but intact, cell envelopes which include inert spherical microparticles. The inert spherical microparticles will be referred to herein as bacterial "ghosts." The term "ghosts" reflects the size and shape of the bacterium from which the ghosts are obtained.

Also disclosed is a method for obtaining cell-wall material of a Gram-positive bacterium with an improved capacity for binding with a proteinaceous substance comprising an AcmA cell-wall binding domain, homolog or functional derivative thereof. The method comprises treating the cell-wall material with a solution capable of removing a cell-wall component such as a protein, lipoteichoic acid or carbohydrate from the cell-wall material, wherein the cell-wall material comprises spherical peptidoglycan microparticles referred to herein as ghosts.

Methods to extract bacterial cell-wall material with a solution have been described in EP 0 545 352 A and Brown et al. (Prep. Biochem. 6:479, 1976). A method to obtain purified soluble peptidoglycan from bacteria by exposure to TCA has been disclosed. The cited references describe procedures in which cells are mechanically disrupted, wherein the resulting cell fragments are treated with TCA to extract peptidoglycans from the cell wall. The cited methods provide a peptidoglycan preparation and a lysed, randomly fragmented cell-wall preparation from which cell-wall components have been removed. However, these methods do not yield ghosts. Furthermore, the methods do not allow targeting with a proteinaceous substance comprising an AcmA cell-wall binding domain, homolog or functional derivative thereof.

The method of the present invention is aimed at yielding ghosts from which cell-wall components have been removed. The use of ghosts for display of proteinaceous substances has advantages over the use of the disrupted cell-wall material. For example, binding the proteinaceous substance to bacterial ghosts results in a higher packing density when compared to binding a substance to mechanically disrupted cell-wall material. A high density surface display of proteins is favorable for application in industrial processes. In one embodiment, the present invention discloses a method for obtaining the cell-wall material not involving rupture.

Cell-wall material obtained by mechanical disruption methods suffers from several practical drawbacks. Because cells are completely broken with mechanical disruption, intracellular materials are released from the cell and cell-wall fragments need to be separated from a complex mixture of proteins, nucleic acids, and other cellular components. The released nucleic acids may increase the viscosity of the solution and complicate processing steps, especially chromatography. The cell debris produced by mechanical lysis also often includes small cell fragments which are difficult to remove. These problems are overcome when ghosts are produced using methods of the present invention. The uniform composition of a ghost preparation including particle size and shape offers other advantages for subsequent purification and isolation steps. The invention thus discloses a method of obtaining cell-wall material not involving rupture of the cell wall, wherein the resulting cell-wall material comprises ghosts.

The use of bacterial ghosts is often preferable when compared to the use of mechanically disrupted cell-wall bacteria for the surface display of immunogenic determinants. In contrast to mechanical disruption procedures, ghosts are produced by a process that preserves most of the bacteria's native spherical structure. Bacterial ghosts are better able to bind to and/or are more easily taken up by specific cells or tissues than mechanically disrupted cell-wall material. The ability of bacterial ghosts to target macrophages or dendritic cells enhances their functional efficacy. Thus, the non-recombinant, non-living ghost system disclosed by the present invention is well suited as a vaccine delivery vehicle. Accordingly, the invention discloses a method for obtaining ghosts, wherein the ghosts have an improved capacity for binding with a proteinaceous substance and have an enhanced induction of the cellular immune response.

The invention also discloses a method for binding a proteinaceous substance to the cell-wall material of a Gram-positive bacterium, wherein the proteinaceous substance comprises an AcmA cell-wall binding domain, homolog or functional derivative thereof. The method comprises treating the cell-wall material with a solution capable of removing a cell-wall component such as a protein, lipoteichoic acid or carbohydrate from the cell-wall material, and subsequently contacting the proteinaceous substance with the cell-wall material. The cell-wall material comprises ghosts which have been produced by the present invention which does not involve rupture of the bacterial cell-wall.

In another embodiment, the solution capable of removing the cell-wall material has a pH that is lower than the calculated Pi value of the AcmA cell-wall binding domain, homolog or functional derivative thereof. Particularly, the solution comprises an acid such as acetic acid (HAc), hydrochloric acid (HCl), sulphuric acid ($H_2SO_4$), trichloro acetic acid (TCA), trifluoro acetic acid (TFA), and monochloroacetic acid (MCA). The concentration of the acid in the solution will be dependent on the desired pH value which may be determined by calculation using a computer program such as DNA star or Clone Manager. For instance, when the calculated pI is >8, pH values of about 6 to 4 may suffice for effecting appropriate binding. When pI values are calculated to be lower, such as around 6, pH values of 3-4 may be selected. When domains with calculated pI values ranging from 8 to 12 are encountered, using the solution comprising 0.06 to 1.2 M TCA, or comparable acid, may suffice.

The binding may be improved by heating the cell-wall material or ghosts in the solution. However, precise requirements for the heating may vary depending on the cell-wall material or ghosts. However, heating for 5-25 minutes at approximately boiling temperature (i.e., 100° C.) will often generate the desired cell-wall material with improved binding capacity. The cell-wall material may then be washed and pelleted (e.g., by centrifugation) from the treatment solution and subsequently stored (e.g., by freezing or freeze-drying) until further use. Such cell-wall material includes spherical peptidoglycan microparticles that usually reflect the size and shape of the bacterium from which they were obtained.

In one embodiment, the cell-wall material is derived from a *Lactococcus*, a *Lactobacillus*, a *Bacillus* or a *Mycobacterium* sp. The cell walls of Gram-positive bacteria include complex networks of peptidoglycan layers, proteins, lipoteichoic acids and other modified carbohydrates. Generally, chemical treatment of the cell-wall material may be used to remove cell-wall components such as proteins, lipoteichoic acids and carbohydrates, wherein the chemical treatment yields purified peptidoglycan (Morata de Ambrosini et al. 1998). Sodium dodecyl sulphate (SDS) is also commonly used to remove proteins. Trichloro acid (TCA) is known to specifically remove lipoteichoic acids and carbohydrates from cell-wall isolates. Phenol, formamide and mixtures of chloroform and methanol are other examples of organic solvents that may be used to enhance the purification of peptidoglycan.

In the present invention, the effect of the pretreatment of whole cells of gram-positive bacteria with these and other chemicals in relation to binding technology provides the possibility to obtain bacterial ghosts or cell-wall material derived from the bacteria which possess new traits (i.e., different binding properties) without the introduction of recombinant DNA.

In another embodiment, the present invention discloses the incorporation of cell-wall material with improved binding capacity for AcmA-type anchors into a composition, such as a pharmaceutical composition, with a proteinaceous substance comprising an AcmA-type anchor. Reactive groups, such as antigenic determinants, heterologous enzymes, single-chain antibodies, polyhistidyl tags, peptides, and other compounds may be bound to the cell-wall material as disclosed herein by providing reactive groups with an AcmA-type anchor, and subsequently contacting the cell-wall material with the reactive groups to improve binding capacity. Other reactive groups include fluorescing protein, luciferase, binding protein or peptide, antibiotics, hormones, non-peptide antigenic determinants, carbohydrates, fatty acids, aromatic substances or reporter molecules.

In another embodiment, the invention discloses the use of cell-wall material in generating bioadsorbents or biofilters for environmental purposes, microbiocatalysts, and diagnostic tools. For instance, the use of immobilized biocatalysts, such as enzymes or whole microbial cells, has increased steadily during the past decade in the food, pharmaceutical and chemical industries. The immobilized biocatalysts are more stable, easier to handle, and can be used repeatedly in industrial processes in comparison to their free counterparts. Immobilization of enzymes typically requires a chemical step to link the enzyme to an insoluble support. However, chemical treatments may negatively affect the enzymes. Alternatively, enzymes may be immobilized by incorporation in gels with the disadvantage that diffusion of the substrate into the gel slows down the process.

As disclosed herein, large-scale immobilization of enzymatically active proteins may be accomplished by surface displaying proteins on gram-positive cells or cell-wall material. For instance, the immobilization of a fusion protein comprising α-amylase or β-lactamase fused to the AcmA-protein anchor domain has been demonstrated herein in *L. lactis*. The addition of the AcmA-anchor fusion protein resulted in the stable attachment of heterologous proteins to the surface of *L. lactis* and other gram-positive bacteria. Further, pre-treating *L. lactis* cells and other gram-positive cells with acid as described herein results in a high density surface display of heterologous proteins and is a prerequisite for application in industrial processes. Further, the carrier or gram-positive cells may be obtained in high yield and be non-recombinant. Thus, a method disclosed herein may be used to economically produce the immobilized enzyme and make the AcmA-protein anchor a useful approach for the surface display of enzymes on gram-positive cells.

Another industrial application of an immobilized enzyme is the isomerization of glucose which is catalyzed by glucose isomerase and used during the production of high-fructose corn syrup. This process may be made economically feasible by immobilizing the glucose isomerase. The productivity of glucose isomerase is improved by increasing the stability of epoxide hydrolase in organic solvents by immobilization to microbial cells or cell-wall material as described herein.

Immobilized enzymes may also be used to treat waste water or industrial effluent. For instance, industrial effluents containing low value chemicals produced during synthesis of the commodity chemicals epichlorohydrin and propylene oxide may be treated by using immobilized haloalkane dehalogenase to recycle these low value products into the manufacturing process.

The invention further discloses chimeric or hybrid AcmA-type anchors for the preparation of a composition that has new binding properties. The AcmA-type anchors can be divided into two groups of hybrids based on their pI (see, Table 3). A large group includes hybrids with a pI higher than 8, but lower than 10, and a smaller group includes hybrids with a relatively low pI (i.e., <5). Hybrid AcmA-type anchors are disclosed with at least one AcmA-type domain and a relatively high calculated pI, and another AcmA-type domain is disclosed with a relatively lower calculated pI. The resulting hybrid anchor has an intermediate calculated pI which is useful when release of the bound proteinaceous substance at a higher pH is contemplated. Such a composition may be routed through the stomach, which has a relative low pH, such that the composition releases its anchor bound reactive groups in the intestines, which have a higher pH.

The invention also discloses a proteinaceous substance comprising an AcmA cell-wall binding domain, homolog or functional derivative thereof wherein the binding domain is a hybrid of at least two different AcmA-type cell-wall binding domains, homologs or functional derivatives thereof. The proteinaceous substance may comprise an AcmA cell-wall binding domain, homolog or functional derivative thereof where the binding domain is a hybrid of at least two different AcmA repeat sequences and has a calculated pI lower than 10. For instance, a hybrid protein anchor including the A1 and A2 repeat sequences of AcmA and the D1 repeat sequence of AcmD may be constructed. Such a hybrid domain may comprise at least one AcmA-type domain with a relatively high calculated pI and another AcmA-type domain with a relatively lower calculated pI. The domain with the relatively high pI may be derived from, or be functionally equivalent to, the AcmA-type domain of the lactococcal cell-wall hydrolase AcmA. Of course, many other domains with a high pI are known, such as those disclosed in Table 3. A domain with a relatively low pI may be derived from, or be functionally equivalent to, the AcmA-type domain of the lactococcal cell-wall hydrolase AcmD. However, other domains with relatively low pI are known, including those disclosed in Table 3.

The invention further discloses a proteinaceous substance comprising a hybrid domain with at least two stretches of amino acids, wherein each stretch corresponds to a domain repeat sequence and is located adjacent to each other. The stretches may be separated by one or more amino acid residues of a short distance, i.e., 3-6 to 10-15 amino acids apart, by a medium distance, i.e., 15-100 amino acids apart, or by longer distances, i.e., >100 amino acid residues apart.

In another embodiment, the invention discloses a proteinaceous substance with a hybrid AcmA domain that further comprises a reactive group. Reactive groups that may be used include, without limitation, antigenic determinants, heterologous enzymes, single-chain antibodies or fragments thereof, polyhistidyl tags, fluorescing proteins, luciferase, binding proteins or peptides, antibiotics, hormones, non-peptide antigenic determinants, carbohydrates, fatty acids, aromatic substances, inorganic particles such as latex, and reporter molecules. The reactive group may also include AcmA cell-wall binding domains, homologs or functional derivatives thereof wherein the binding domain is a hybrid of at least two different AcmA cell-wall binding domains, homologs or functional derivatives thereof that are useful in heterologous surface display and are broadly reactive with cell-wall components of a broad range of micro-organisms. As used herein, the AcmA cell-wall binding domains, homologs and functional derivatives thereof will also be referred to as hybrid AcmA domains.

The invention further discloses reactive groups which are non-protein moieties, including substances such as antibiotics, hormones, aromatic substances, inorganic particles, or reporter molecules. The substances may be constructed by binding an antibiotic, such as penicillin, tetracycline or various other antibiotics, a hormone, such as a steroid hormone, or any other compound to a binding domain produced by the present invention. Such binding may be achieved using various techniques known in the art and may function to label or "flag" the binding domain. For instance, a binding domain may be bound to a reporter molecule such as fluorescent nanoparticles, i.e., FITC or HRPO, wherein tools are generated that may be used in diagnostic assays to detect microorganisms possessing peptidoglycan. Similarly, a binding domain may be bound to an antibiotic and used for in vivo parenteral administration into the bloodstream of humans or animals, or used in vitro to bind microorganisms with peptidoglycan in order to increase the concentration of the antibiotic around the microorganism which may be killed by the antibiotics.

The invention further discloses a reactive group which is a protein moiety which may include, without limitation, antigenic determinants, enzymes, single-chain antibodies or fragments thereof, polyhistidyl tags, fluorescing proteins, binding proteins or peptides. For instance, a protein including a reactive group which is another protein or polypeptide is disclosed. The invention also discloses a nucleic acid molecule encoding the protein produced using the methods of the invention. Such a nucleic acid molecule, comprising single-stranded or double-stranded DNA, RNA or DNA-RNA duplex, comprises nucleic acid sequences which encode a hybrid binding domain. The nucleic acid molecule may also comprise nucleic acid sequences encoding the reactive group polypeptide and may further comprise other nucleic acid sequences encoding a signal peptide comprising promoter sequences or regulatory nucleic acid sequences.

A vector comprising a nucleic acid molecule encoding a proteinaceous substance provided by the invention is also disclosed. Examples of vectors include, without limitation, a plasmid, a phage or a virus, wherein the vectors may be constructed using nucleic acids of the invention and routine skills known in the art. Viral vectors include baculovirus vectors or comparable vector viruses through which a protein produced by the present invention may be expressed or produced in cells, such as insect cells.

A host cell or expression system including a nucleic acid molecule or a vector produced using methods of the present invention is also disclosed. The host cell expressing a protein of the present invention may be a microorganism to which the protein is attached. The host cell, or expression system, may be a Gram-positive bacterium, a Gram-negative bacterium, a yeast cell, an insect cell, a plant cell, a mammalian cell, or a cell-free expression system, such as a reticulocyte lysate. The host cell or expression system may be constructed or obtained using a nucleic acid or vector of the present invention and routine skills known in the art.

In a further embodiment, the invention discloses a pharmaceutical composition comprising cell-wall material with an improved binding capacity with an immunogen bound thereto which may be useful for vaccination purposes, i.e., a vaccine. The vaccine may be used to invoke immunity against pathogens, such as malaria, which undergo life cycle stages where the pathogen is not in the blood but hides in cells.

The vaccines may be delivered to mucosal surfaces instead of being injected since mucosal surface vaccines are easier and safer to administer. An *L. lactis*-derived cell-wall material may be used for mucosal vaccination since this bacterium is of intestinal origin and no adverse immune reactions are generally expected from *L. lactis*.

The vaccine of the invention may also be administered by injection. When the vaccine is administered through injection, cell-wall material may be derived from a *Mycobacterium* sp. since mycobacterial cell-wall preparations have beneficial adjuvant properties. The mycobacterial cell-wall vaccine may be mixed with the proteinaceous substance carrying the immunogenic determinants used in the vaccine.

A vaccine produced using a method of the present invention will likely have a reduced risk of generating undesirable immune responses against cell-wall compounds of unwanted immunogens because the unwanted immunogens are not included in the vaccine.

BRIEF DESCRIPTION OF THE DRAWINGS

FIG. 2A. Fluorescence microscopic images of bacterial cells with externally bound MSA2::cA. *Lb. curvatis, Lb. sake* and *L. lactis* cells that were not pretreated prior to binding.

FIG. 2B. Fluorescence microscopic images of bacterial cells with externally bound MSA2::cA. *L. lactis* cells that were TCA-pretreated prior to binding. The light colored areas indicate the position where the reporter protein MSA2::cA binds. The difference between *L. lactis* cells that were not pretreated with TCA (in FIG. 2A) and those that were TCA pretreated is apparent (in FIG. 2B).

FIG. 6. Alignment of cA repeats with cD repeats. AcmA (A1) (SEQ ID NO:16) is aligned to AcmD (D1) (SEQ ID NO:19). AcmA (A2) (SEQ ID NO:17) is aligned to AcmD (D2) (SEQ ID NO:20). AcmA (A3) (SEQ ID NO:18) is aligned to AcmD (D3) (SEQ ID NO:21). Consensus repeats SEQ ID NOS: 163, 164 and 165 are aligned. The amino acids that are in agreement with the consensus sequence are shown at the bottom of the figure (defined in PCT Publication WO99/25836) are underlined. The asterisks indicate residues that are identical between the compared repeats.

FIG. 8. Fluorescence microscopy image of TCA-pretreated *L. lactis* cells incubated with MSA2::cA or MSA2::cD. Light colored areas indicate the position were the reporter fusion protein binds. It appears that binding only occurred with MSA2::cA and not with MSA2::cD.

FIG. 11. Fluorescence microscopy image of MSA2::cA binding to *Lb. casei* with or without TCA pretreatment. The light colored areas represent bound MSA2::cA. TCA pretreatment improves binding of MSA2::cA and *Lb. casei*.

FIG. 12. Fluorescence microscopy image of MSA2::cA and MSA2::cD binding to *M. smegmatis* pretreated with TCA. The light colored areas represent bound MSA2 fusion protein. As illustrated, only MSA2::cA binds.

FIG. 14A. Fluorescence microscopy image of MSA2::cA surface expression in the recombinant strain NZ9000 (pNG3041). The light colored areas indicate the position of MSA2 fusion protein. The recombinant strain producing MSA2::cA has the protein on the surface in some specific spots.

FIG. 14B. Fluorescence microscopy image of MSA2::cP surface expression in the recombinant strain NZ9000 (pNG3043). The recombinant strain producing MSA2::cP has more on the surface organized in several areas.

FIG. 14C. Fluorescence microscopy image of MSA2::cA binding to TCA pretreated *L. lactis* cells. The surface of the TCA-pretreated non-recombinant *L. lactis* with bound MSA2::cA is completely covered with the protein.

DETAILED DESCRIPTION

EXAMPLE 1

Acid Pretreatment of Gram-Positive Bacteria Enhances Binding of AcmA Protein Anchor Fusions Materials and Methods.

Bacterial Strains and Growth Conditions. *Lactococcus lactis* strain MG1363 (Gasson 1983) or derivatives thereof, such as MG1363ΔacmA (Buist et al. 1995) or NZ9000ΔacmA, were used as recipients for binding of reporter fusion protein. NZ9000 (Kuipers et al. 1997), which carries one of the reporter plasmids, was used as a production strain. *L. lactis* strains were grown in M17 broth (Oxoid) supplemented with 0.5% glucose in standing cultures at 30° C. Chloramphenicol was added to the M17 medium to an end-concentration of 5 μg/ml when appropriate. For expression, mid-log phase cultures were induced for 2 hours with the culture supernatant of the nisin producing *L. lactis* strain NZ9700 as described by Kuipers et al. (1997). *Lactobacillus casei*, ATCC393, was grown in MRS broth (Oxoid) in standing cultures at 30° C. *Mycobacterium smegmatis*, ATCC700084, was grown in Middlebrook medium (Oxoid) at 37° C. in aerated cultures. *Bacillus subtilis*, 168, was grown in TY broth (per liter: 10 g tryptone, 5 g yeast extract, 5 g NaCl pH 7.4) at 37° C. in aerated cultures.

Figure 1:
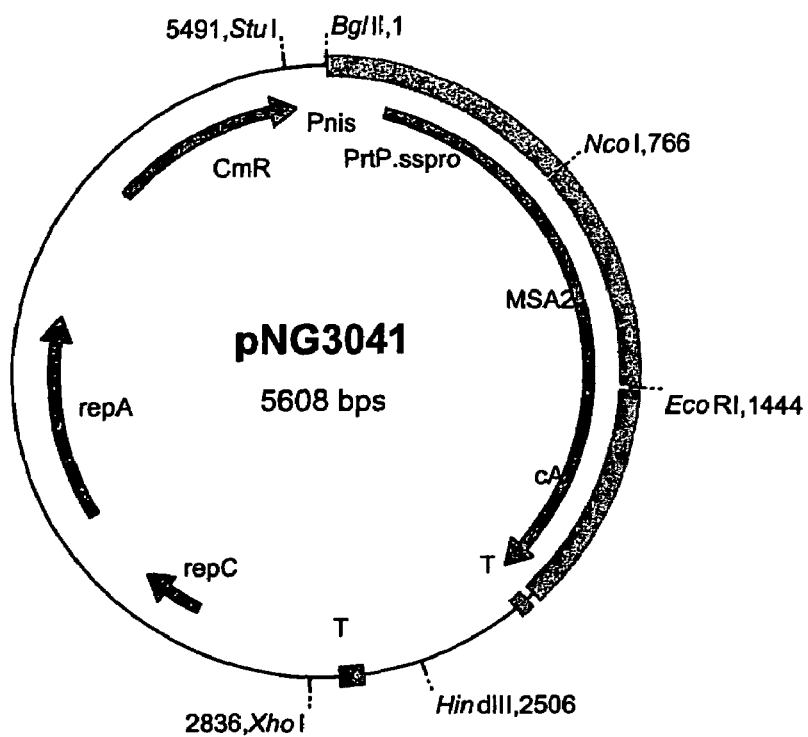
FIG. 1. Schematic map of plasmid pNG3041 that encodes the reporter protein MSA2::cA that is secreted as a proprotein using the lactococcal PrtP signal- and prosequences (PrtP.sspro). Pnis represents the nisin inducible promoter of the nisA gene. T represents the transcriptional terminator. CmR is the chloramphenicol resistance gene. repC and repA are genes involved in the replication of the plasmid.

Construction of Reporter Plasmids. The merozoite surface antigen 2 (MSA2) of *Plasmodium falciparum* strain 3D7 (Ramasamy et al. 1999) fused to the three repeats of AcmA (MSA2::cA) was used as the reporter anchor protein. The reporter anchor protein is encoded by plasmid pNG3041 based on the nisin inducible expression vector pNZ8048 (Kuipers et al. 1997) and contains a modified multiple cloning site in which the hybrid reporter gene was cloned. An in-frame fusion of the reporter was made at the 5' end, the lactococcal PrtP signal- and prosequence, and at the 3' end, the AcmA protein anchor sequence. The sequence of the MSA2 gene that was included in the construct corresponds to nucleotides (nt) 61 to 708 in GenBank accession number A06129. Primers used for the amplification of the MSA2 gene were MSA2.1 (5'-ACCATGGCAAAAAATGAAAG-TAAATATAGC (SEQ ID NO:2)) and MSA2.4 (5'-CG-GTCTCTAGCTTATAAGCTTAGAATTCGG-GATGTTGCTGCTCCACAG (SEQ ID NO:3)). The primers contain tags with restriction endonuclease recognition sites that were used for cloning. For cloning of the PrtP signal and prosequence (nt 1206 to 1766 in Kok et al. 1988), the primers PrtP.sspro.fw (5'-CCGTCTCCCATGCAAAG-GAAAAAAGA AAGGGC (SEQ ID NO:4)) and PrtP.sspro-.rev (AAAAAAAGCTTGAATTCCCAT GGCAGTCG-GATAATAAACTTTCGCC (SEQ ID NO:5)) were used. The primers include restriction sites that were used for cloning. The AcmA protein anchor gene fragment (nt 833 to 1875) was obtained by subcloning a PvuII-HindIII fragment from plasmid pAL01 (Buist et al. 1995). Restriction endonuclease enzymes and Expand High Fidelity PCR polymerase were used in accordance with the instructions of the supplier (Roche). The final expression vector was designated pNG3041 (FIG. 1).

A construct including a stop codon introduced after the MSA2 sequence in pNG3041 was designated pNG304. The protein secreted using this construct is substantially the same as the protein expressed from the pNG3041 plasmid except that the protein produced from pNG304 does not contain the AcmA protein anchor. The protein produced from pNG304 is used as a negative control in the binding assays. A vector was also made in which the AcmA protein anchor was exchanged for a protein anchor. The putative cell-wall binding domain of L. lactis AcmD (Bolotin et al. 2001) was cloned (nt 1796 to 2371 in GenBank accession number AE006288) using primers pACMB2 (5'-CGCAAGCTTCTGCAGAGCTCTTA-GATTCTAATT GTTTGTCCTGG (SEQ ID NO:6)) and pACMB3 (5'-CGGAATTCAAGGAGGAGAAATA TCAG-GAGG (SEQ ID NO:7)) to produce the plasmid pNG3042. pNG3042 contains an in-frame fusion between MSA2 and the protein anchor of AcmD (MSA2::cD) and differs from plasmid pNG3041 only in the gene fragment encoding the protein anchor.

Cell Pretreatment and Binding Conditions. Chemical pretreatment of L. lactis NZ9000ÄacmA was done with 10% TCA (0.6 M) in the following manner. Cells of 0.5 ml stationary phase cultures were sedimented by centrifugation and washed once with 2 volumes of demineralized water. Cells were resuspended in 1 volume of a 10% TCA solution and incubated by placing the reaction tube in boiling water for 15 minutes. Subsequently, cells were washed once with 2 volumes PBS (58 mM $Na_2HPO_4.2H_2O$, 17 mM $NaH_2PO_4.H_2O$, 68 mM NaCl; pH 7.2) and three times with 2 volumes demineralized water. The cells were used directly for binding experiments or stored (as described herein) until further use.

The following chemicals and conditions were used to examine the effect of different chemicals on the binding capacity of L. lactis cells for AcmA-type protein anchor fusions: acetic acid (HAc), hydrochloric acid (HCl), sulfuric acid ($H_2SO_4$), trifluoroacetic acid (TFA), and monochloro acetic acid (MCA). The acids were used at a final concentration of 0.6 M and incubated for 15 minutes in boiling water. SDS, dimethyl formamide (DMF) and dimethyl sulfoxide (DMSO) were used at a concentration of 10%. The SDS pretreatment was incubated for 15 minutes in boiling water and DMF and DMSO treatments were incubated at room temperature for 15 minutes. Cells were also pretreated with phenol (Tris buffer saturated) and incubated for 15 minutes at 55° C. Other chemicals pretreated at the 55° C. incubation temperature were: 4 M guanidine hydrochloride (Gn-HCl), 37% formaldehyde, chloroform:methanol ($CHCL_3$: $CH_3OH$ (2:1)) and 0.1% sodium hypochlorite (NaOCl). In addition, incubation with 25 mM dithiothrietol (DTT) for 30 minutes at 37° C. and a pretreatment with hexane (100%) were analyzed.

The effect of enzymatic pretreatment of cells with lysozyme was also tested. For lysozyme pretreatment, the cells were resuspended in buffer (20% sucrose, 10 mM Tris pH 8.1, 10 mM EDTA, 50 mM NaCl) with lysozyme (2 mg/ml) and incubated at 55° C. for 15 minutes. After the chemical and enzymatic pretreatments, the washing steps were the same as the washing steps used for the TCA-treated cells. TCA pretreatment of Bacillus subtilis, Lactobacillus casei and Mycobacterium smegmatis was done as described herein for L. lactis.

Cell-free culture supernatants containing MSA2::cA, MSA2::cD or MSA2 without anchor were incubated in four-fold excess for 10 minutes at room temperature with pretreated cells (e.g., cells from 0.5 ml culture were incubated with 2.0 ml culture supernatant). After binding, cells were sedimented by centrifugation, washed twice in 2 volumes of demineralized water, resuspended in SDS-denaturation buffer, heated for 5 minutes at 98° C., subjected to SDS-PAGE, and analyzed by Western blot analysis.

Storage Conditions. Cell-free supernatants containing MSA2::cA, MSA2::cD or MSA2 were stored at −20° C. with or without 10% glycerol prior to binding. TCA-pretreated L. lactis cells were stored at −80° C. in 10% glycerol prior to binding. TCA pretreated L. lactis cells with bound MSA2::cA were stored at +4° C. or −80° C. with or without 10% glycerol. Cells stored in 10% glycerol were washed once with 1 volume of demineralized water prior to binding.

Cell pellets (in demineralized water) of TCA-pretreated L. lactis cells with or without bound MSA2::cA were frozen by contacting the vials with liquid nitrogen and removing the water with lyophilization. Alternatively, non-frozen cell pellets were dried under vacuum at 30° C. for 2 hours prior to binding.

Western Blotting. For detection of MSA2 proteins, cell pellets corresponding to 500 µl culture were resuspended in 50 µl SDS-denaturation buffer. Cell-free culture supernatants (1 ml) were concentrated by phenol-ether precipitation (Sauvé et al. 1995), vacuum dried and resuspended in 50 µl SDS-denaturation buffer. Proteins were separated with standard SDS-PAGE techniques. After separation, proteins were electroblotted onto PVDF membranes (Roche). In immunoblots, MSA2 proteins were detected with 1:10,000 diluted rabbit MSA2-specific antiserum (Ramasamy et al. 1999) and 1:5,000 diluted anti-rabbit IgG-conjugated alkaline phosphatase (Roche) using known procedures.

Fluorescence Microscopy. 100 µl cell suspensions incubated with MSA2::cA, MSA2::cD or MSA2 fusion proteins were washed twice with demineralized water and resuspended in an equal volume of PBS containing 1% BSA and MSA2-specific rabbit antiserum diluted to 1:200. After incubation for 20 minutes at room temperature, the cells were washed three times with 2 volumes PBS. Subsequently, the cells were incubated for 20 minutes in 1 volume PBS with 1% BSA and 1:100 diluted Oregon green labeled goat anti-rabbit immunoglobulin G (Molecular Probes). After washing once with 2 volumes PBS and twice with 2 volumes demineralized water, the cells were resuspended in 100 µl demineralized water. A 10 µl aliquot of the resuspended cells was spread onto a Polysin microslide (Menzel-Gläser), air dried, and examined under a fluorescence microscope (Zeiss).

Electron microscopy. TCA-pretreated *L. lactis* cells incubated with MSA2::cA, MSA2::cD or MSA2 were collected and washed as described herein. Immunogold labeling was performed on whole mount preparations of glutaraldehyde fixed cells on Formvar-carbon coated nickel grids using Auroprobe 15 nm goat anti-rabbit IgG gold marker (Amersham). Primary antibodies against MSA2 were diluted 1:1000 in PBS-glycine buffer. The labeled samples were stained with 0.1% uranyl acetate (W/V in water) and examined in a Philips CM10 transmission electron microscope at 100 kV.

Pretreatment of *L. Lactis* Cells with Different Chemicals. The cA protein anchor of *L. lactis* AcmA can be used to bind fusion proteins to a wide variety of Gram-positive bacteria. However, the amount of fusion protein that binds varies greatly among this group of bacteria. Binding of MSA2::cA that covers the entire cell surface of some lactobacilli was observed, whereas other bacteria such as *L. lactis* showed only limited localized binding (FIG. 2A). This phenomenon may be due to the fact that the cell walls of some bacterial species contain components that interfere with cA anchor binding. Since chemicals like SDS, TCA, chloroform/methanol and others may be used to remove components from isolated bacterial cell walls (Morata de Ambrosini et al. 1998), the effect of the removal of cell-wall components from *L. lactis* whole cells on the binding of the reporter fusion protein MSA2::cA was investigated. *L. lactis* cells were pretreated as described herein with various chemicals or with lysozyme.

Figure 3:
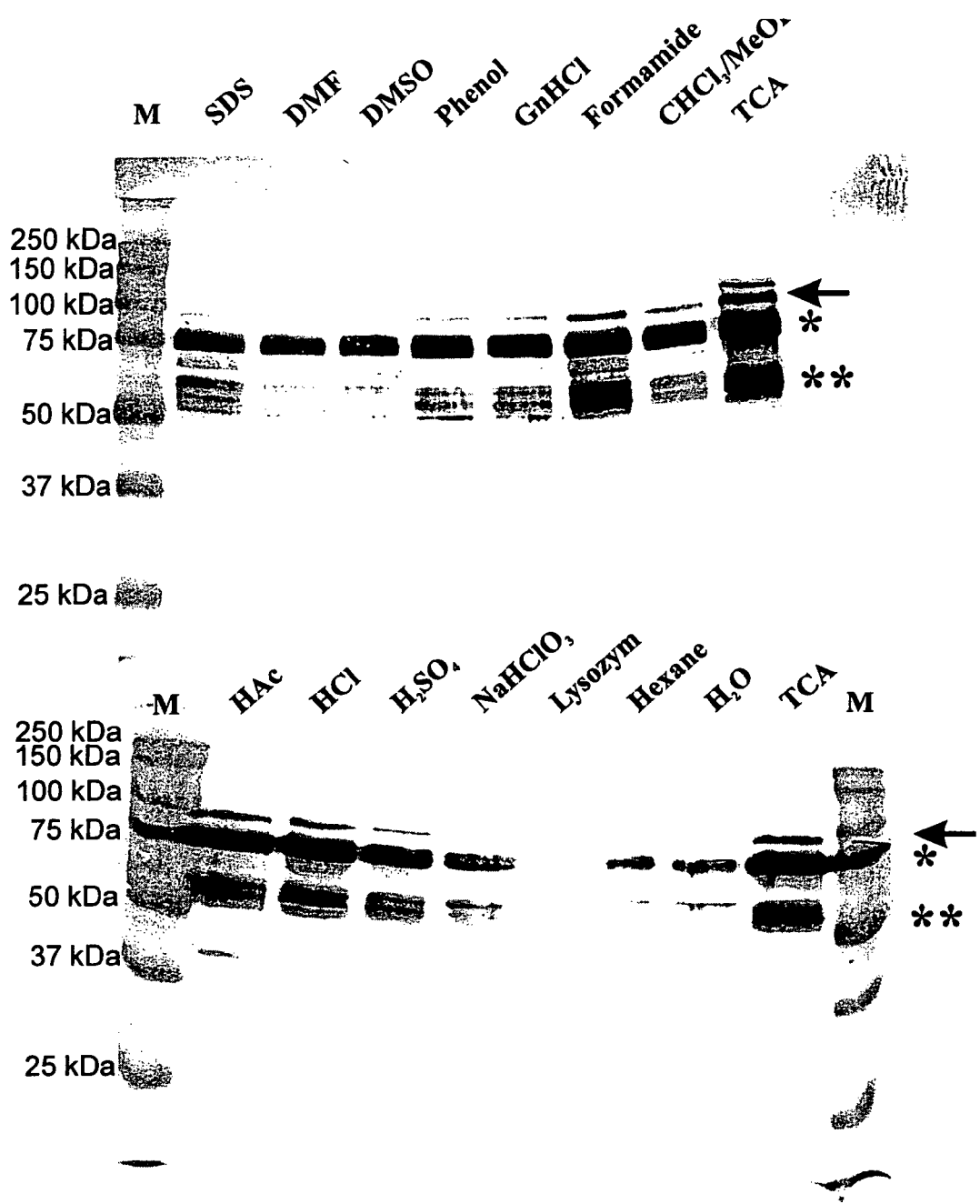
FIG. 3. Western blots of chemically pretreated *L. lactis* cells that were washed after the pretreatment and incubated with MSA2::cA to allow binding. Unbound MSA2::cA was removed by washing. The drawing shows the MSA2::cA that was bound to the chemically pretreated cells and detected using an antibody specific for MSA2. The different pretreatments are indicated above the lanes. MSA2::cA is produced by the producer cells as a proprotein, pro-MSA2::cA. Some pro-MSA2::cA is present in the medium used for binding and binds as indicated by the arrow. A membrane bound protease, HtrA, of the producer cells cleaves off the prosequence, resulting in mature MSA2::cA, which also binds to the pretreated cells as indicated by the asterisk. HtrA also cleaves off the repeats of the cA anchor. Since there are three repeats, MSA2 proteins of several sizes are present in the medium of the producer. As long as more than one repeat is present, binding can still occur. The double asterisks point to MSA2::cA from which one or two repeats have been cleaved. M is a molecular weight marker. The molecular weights are indicated in the left margin. The two blots have different signal intensities. As a reference, both blots contain the same TCA-pretreated samples. The difference in signal intensity is due to differences in stain developing time. It is apparent that the TCA and other acid pretreatments produce pronounced effects on the subsequent binding of MSA2::cA. The conclusions for all chemical pretreatments are summarized in Table 1.

FIG. 3 shows typical Western blots of pretreated whole cells to which MSA2::cA was bound. Mature MSA2::cA migrates at a position of a 75 kDa protein (indicated by an asterisk). The arrow represents MSA2::cA that contains the PrtP prosequence. The double asterisks represent MSA2::cA from which one or two of the repeats have been removed. A cell membrane anchored protease HtrA has been shown to be involved in processing proproteins and in removing repeats from AcmA (Poquet et al. 2000). From the results of FIG. 3, it may be concluded that pretreatment with TCA (lanes 8 and 16 contain the same samples, the difference in signal intensity is due to differences in stain developing time), HCl, $H_2SO_4$ and HAc substantially improves the subsequent binding of MSA2::cA (compare with the negative control in lane 15). Other tested acids, TFA and MCA, had similar effects (not shown). Phenol, GnHCl, formamide and chloroform/methanol pretreatments showed a moderate improvement of binding (lanes 4, 5, 6, 7, respectively). Minor binding improvements were observed after pretreatment with SDS, DMF, DMSO and DTT. The results are summarized in Table 1. Based on the results, it appears that pretreatment of *L. lactis* cells with the acids TCA, TFA, MCA, HCl, $H_2SO_4$ and HAc are the most effective agents for improving binding of cA anchor fusion proteins to lactococcal cells. Acids such as TCA are known to remove lipoteichoic acids from cell walls.

Figure 4:
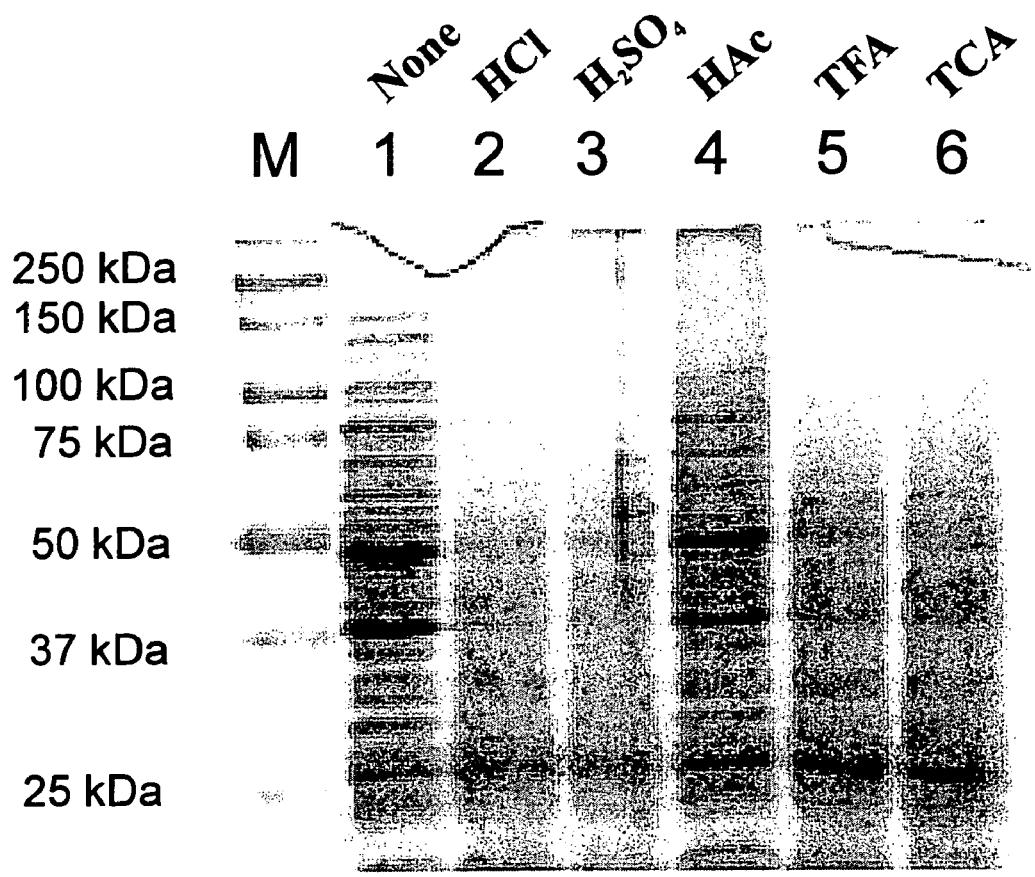
FIG. 4. Coomassie stained SDS-PAGE gel with chemically pretreated *L. lactis* cells. Pretreatments: (1) no-treatment; (2) HCl; (3) $H_2SO_4$; (4) HAc; (5) TFA; and (6) TCA. It is apparent that treatment of the cells with HCl, $H_2SO_4$, TFA or TCA significantly removes an amount of protein from the cells.

Whether proteins are removed from the cell walls by these acid treatments was also analyzed. FIG. 4 shows a Coomassie stained gel of lysed pretreated cells. Most of the acid treatments, except for HAc, removed a substantial amount of proteins from the lactococcal cells. Since HAc removed only a trace amount of proteins (compare lane 1 and 4) and SDS pretreatment (which is known to remove proteins from the cell walls) showed only a minor improvement of MSA2::cA binding (FIG. 3, lane 1), it may be concluded that removal of proteins from the cell wall is not critical for improving the binding of cA anchor fusions. This conclusion may be due to the fact that lipoteichoic acids or carbohydrates occupy sites in the cell walls of *L. lactis* that interfere with efficient binding. Alternatively, acid pretreatment may result in altering the compactness of peptidoglycan strands that make cA binding sites more available.

Figure 5:
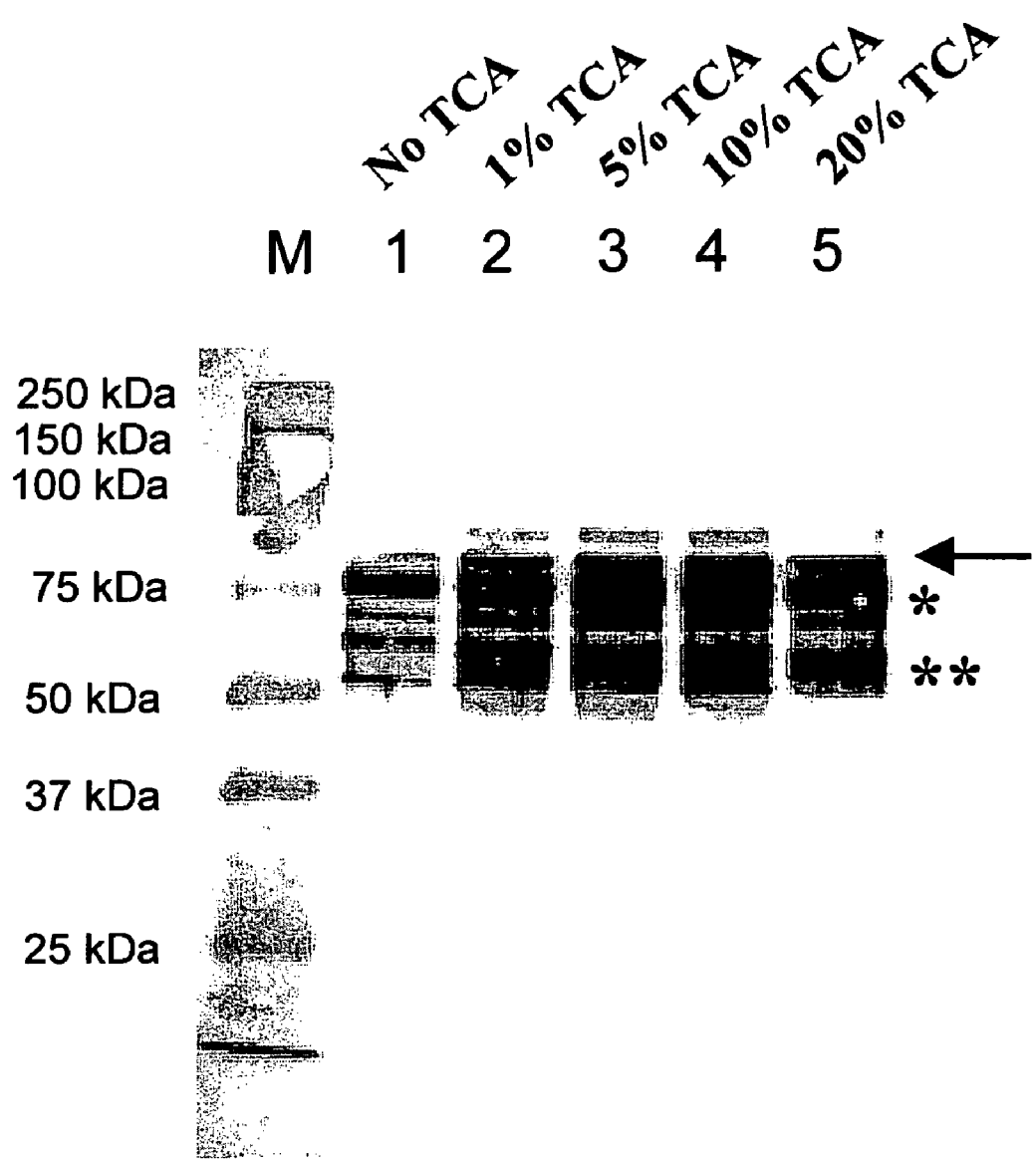
FIG. 5. Western blot of *L. lactis* cells pretreated with different TCA concentrations and externally bound with MSA2::cA. Arrow and asterisks: as in FIG. 3. Pretreatments: (1) no TCA treatment; (2) 1% TCA; (3) 5% TCA; (4) 10% TCA; and (5) 20% TCA. An increase in the binding of MSA2::cA is shown to correlate with increasing amounts of TCA used in the pretreatment.

TCA pretreatment was also used in all other experiments. The optimal TCA concentration in the boiling procedure was determined. TCA percentages of 1, 5, 10 and 20% were tested. Although 1% TCA pretreatment already showed a significant improvement in binding of MSA2::cA and 5% TCA pretreatment showed a further increase, no further improvement was observed at concentrations higher than 10% TCA (FIG. 5). Therefore, the boiling procedure with 10% TCA was selected as the standard procedure for the experiments.

Figure 7:
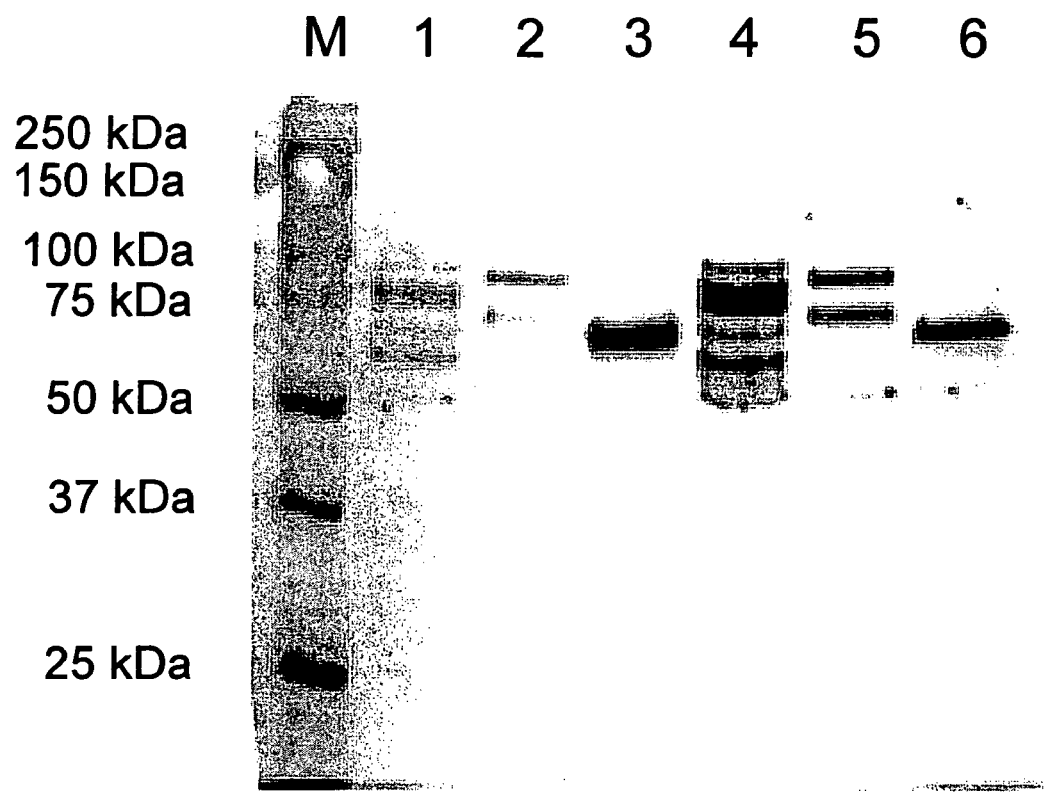
FIG. 7. Binding of various anchor-fusion proteins to *L. Lactis* with and without TCA pretreatment. Multiple bands shown in one lane are caused by the different processed forms of MSA2 fusions. Lanes: (1) non-pretreated *L. lactis*+MSA2::cA; (2) non-treated *L. lactis*+MSA2::cD; (3) non-pretreated *L. lactis*+MSA2; (4) TCA-pretreated *L. lactis*+MSA2::cA; (5) TCA-pretreated *L. lactis*+MSA2::cD; and (6) TCA-pretreated *L. lactis*+MSA2. The effect of TCA pretreatment on the binding of MSA2::cA is shown (i.e., compare lanes 1 and 4). A minor improvement for MSA2::cD and no improvement for MSA2 without anchor is observed. Since there is a signal for MSA2 without the anchor means that MSA2 by itself has a weak affinity for bacterial cell walls. However, MSA2::cD or MSA2 binding to the pretreated cells cannot be detected using fluorescence or electron microscopy (see text). The difference in results is probably due to a difference in sensitivity of the techniques.
Figure 9:
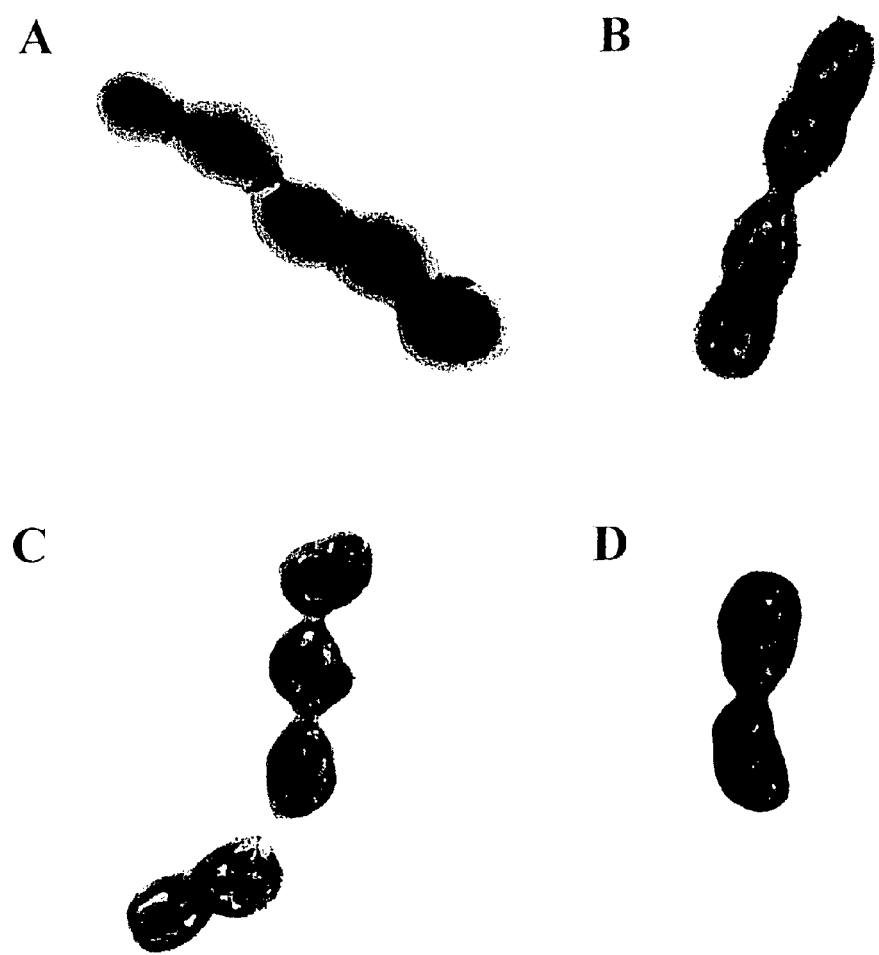
FIG. 9A. Electron microscopy images of *L. lactis* cells incubated with different MSA2 constructs. The black dots represent the position of bound MSA2 fusion protein. Image A depicts non-pretreated cells incubated with MSA2::cA.
FIG. 9B. Electron microscopy images of *L. lactis* cells incubated with different MSA2 constructs. The black dots represent the position of bound MSA2 fusion protein. Image B depicts TCA-pre-treated cells incubated with MSA2::cA. Significant binding, shown by black dots, is only visible in the TCA-pre-treated cells incubated with MSA2::cA.
FIG. 9C. Electron microscopy images of *L. lactis* cells incubated with different MSA2 constructs. The black dots represent the position of bound MSA2 fusion protein. Image C depicts TCA-pre-treated cells incubated with MSA2::cD.
FIG. 9D. Electron microscopy images of *L. lactis* cells incubated with different MSA2 constructs. The black dots represent the position of bound MSA2 fusion protein. Image D depicts TCA-pre-treated cells incubated with MSA2.

The binding characteristics of the lactococcal cA homolog cD in an MSA2 fusion were analyzed using the standard TCA pretreatment procedure. Two of the three AcmD repeats are highly homologous to those of AcmA. An alignment is shown in FIG. 6. Secreted MSA2 without an anchoring domain was included in these experiments as a negative control. In Western blots, the effect of TCA pretreatment on the binding of MSA2::cA was evident (FIG. 7, compare lanes 1 and 4). The effect of TCA pretreatment was also studied using fluorescence microscopy (FIG. 2, compare *L. lactis* in A and B; FIG. 8) and electron microscopy (FIG. 9, compare A and B). Independent of the technique used, the effect of TCA pretreatment on the binding of MSA2::cA can be detected.

The binding of MSA2::cD to non-TCA-pretreated *L. lactis* cells was low as detected in Western blots (FIG. 7, lane 2) and was undetectable in fluorescence microscopy and electron microscopy (FIG. 9A). TCA pretreatment only had minor effects on the intensity of the MSA2::cD signal in Western blots (FIG. 7, lane 5). At the same time, no MSA2::cD specific signal associated with the pretreated cells could be observed in fluorescence microscopy (FIG. 8) and only low levels of labeling were observed in electron microscopy (FIG. 9C). Some cell-associated signal was observed for MSA2 without anchoring domain for both non-TCA pretreated and TCA-pretreated *L. lactis* cells (FIG. 7, lanes 3 and 6, respectively). However, for MSA2::cD, this was not observed in fluorescence microscopy (not shown) and only minor labeling signals were found in electron microscopy (FIG. 9D). Taken together, it may be concluded that: (i) the reporter protein MSA2 does have some low degree of affinity for bacterial cell walls that can be detected in Western blots; (ii) the cA anchor domain specifically stimulates the binding of the reporter fusion to non-pretreated cells; (iii) chemical pretreatment, especially with acids, enhances this binding; and (iv) the cD anchor domain does not promote binding of fusion proteins under the conditions applied.

The fluorescence microscopic images and electron microscopic images of TCA pretreated lactococcal cells (FIGS. 2, 8 and 9) showed that pretreatment leaves the integrity of the cell intact. However, cells are no longer viable (plating efficiency 0) and therefore may be considered as inert spherical peptidoglycan microparticles with a diameter of approximately 1 µm, "ghost cells."

Figure 10:
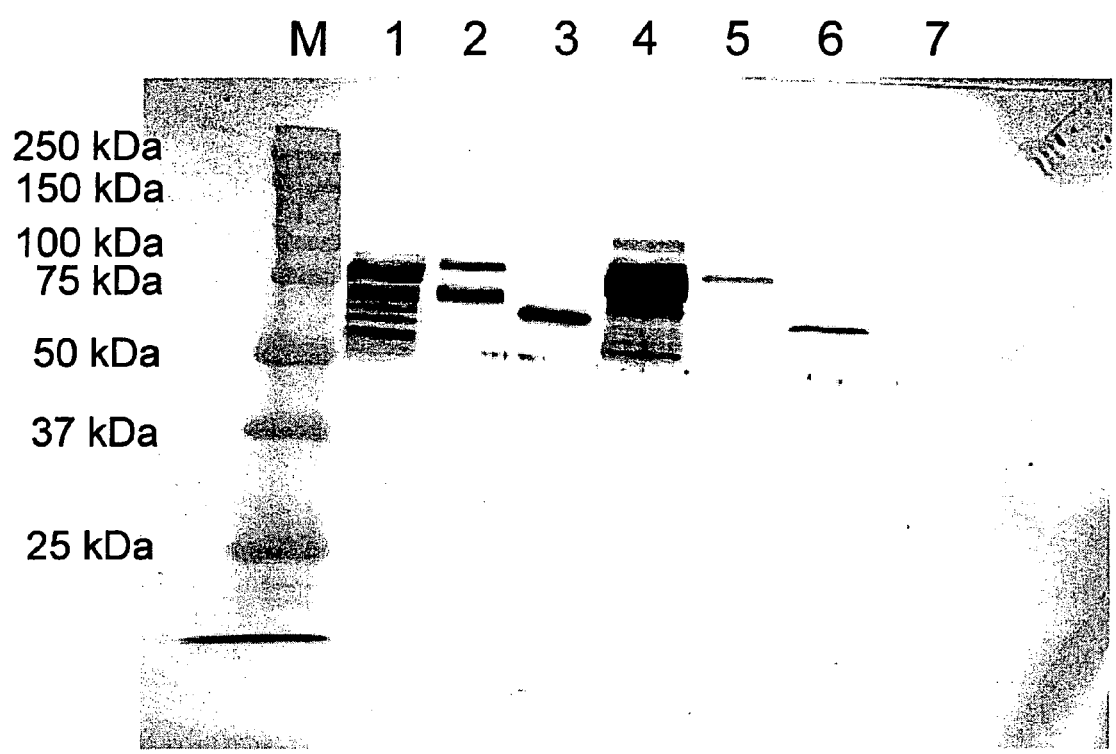
FIG. 10. Binding of different anchor-fusion proteins to *B. subtilis* with and without TCA pretreatment. The drawing is a Western blot similar to FIGS. 3 and 7. Lanes: (1) non-pretreated cells+MSA2::cA; (2) non-pretreated cells+MSA2::cD; (3) non-pretreated cells+MSA2; (4) TCA-pretreated cells+MSA2::cA; (5) TCA-pretreated cells+MSA2::cD; (6) TCA-pretreated cells+MSA2; and (7) non-pretreated *B. subtilis* (negative control). TCA pretreatment improves the binding of MSA2::cA in a manner similar to *L. lactis* (i.e., compare lanes 1 and 4). Only background binding is observed for MSA2::cD and MSA2 without anchor.

Binding to Other Gram-Positives. The binding of MSA2::cA, MSA2::cD and MSA2 without anchor domain to the Gram-positive bacteria B. subtilis, Lb. casei and M. smegmatis was also analyzed. FIG. 10 shows a Western blot summarizing binding of MSA2::cA, MSA2::cD and MSA2 to non-pretreated and TCA-pretreated B. subtilis cells. As for L. lactis, an increase in binding is observed for MSA2::cA. An MSA::cA specific signal could also be visualized in fluorescence microscopy of non-pretreated B. subtilis cells, but with a highly improved signal for the TCA-pretreated cells (not shown). Binding of MSA2::cD and MSA2 to non-pretreated or TCA-pretreated cells could not be demonstrated in fluorescence microscopy (not shown).

Similar results were obtained for Lb. casei and M. smegmatis. The improved binding of MSA2::cA to TCA-pretreated Lb. casei cells is shown in FIG. 11. For MSA2::cD and MSA2, no fluorescence signals were detected (not shown). The TCA pretreatment of M. smegmatis also had a positive effect on the binding of MSA2::cA, whereas no binding was observed for MSA2::cD or MSA2 (FIG. 12). Taken together, it may be concluded that acid pretreatment, such as with TCA, improves the binding of cA protein anchor fusions to the cell surface of Gram-positive bacteria.

Binding strength and storage conditions. The strength of the MSA2::cA binding to TCA-pretreated L. lactis cells was analyzed with a treatment of LiCl after the binding. LiCl is commonly used to remove proteins from bacterial cell walls. From the Western blot of FIG. 13, it may be concluded that 8 M LiCl partially removes MSA2::cA from the L. lactis cells (compare lanes 4 and 5). Therefore, although MSA2::cA binds non-covalently to cell walls, the binding interactions are most likely very strong.

Cell-free culture supernatants with MSA2::cA were stored with or without 10% glycerol at −20° C. MSA2::cA stored in this manner for several weeks had the same capacity to bind to TCA-pretreated L. lactis cells (not shown).

Figure 13:
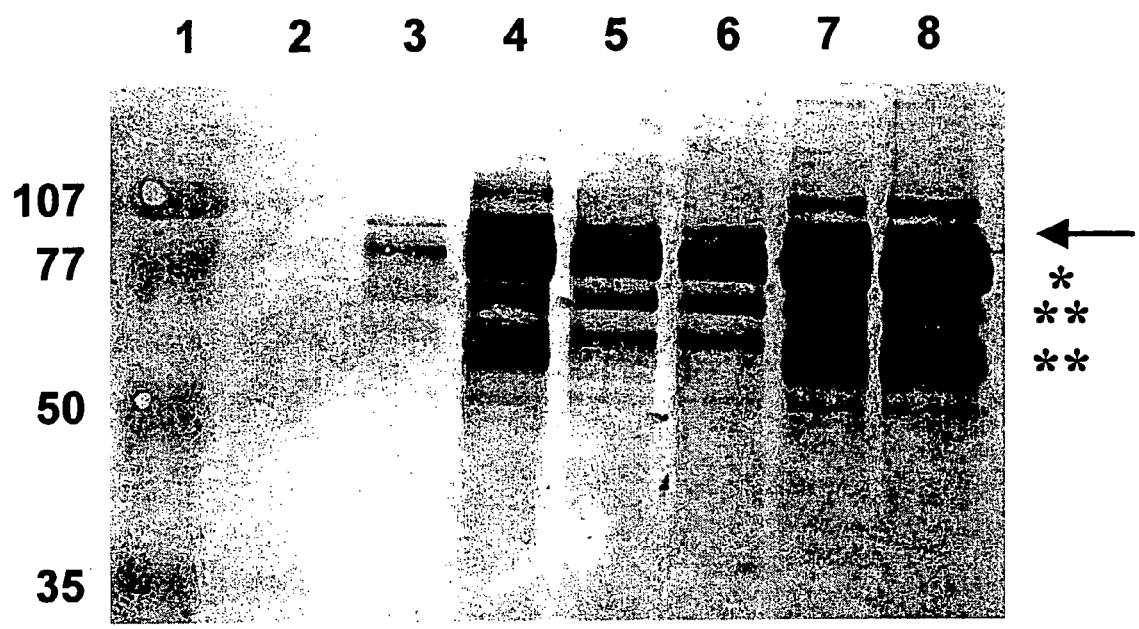
FIG. 13. Western blot of *L. lactis* cells with externally bound MSA2::cA treated with LiCl or stored under different conditions. The bands in the various lanes represent the amount of MSA2::cA that remained bound to the TCA-pretreated cells. Arrow and asterisks: as in FIG. 3. Lanes: (1) marker; (2) non-pretreated *L. lactis* incubated without MSA2::cA; (3) non-pretreated *L. lactis* incubated with MSA2::cA; (4) TCA-pretreated *L. lactis* incubated with MSA2::cA; (5) TCA-pretreated *L. lactis* incubated with MSA2::cA, subsequently washed with 8 M LiCl; (6) TCA-pretreated *L. lactis* incubated with MSA2::cA, subsequently stored in water for 3 weeks at 4° C.; (7) TCA-pretreated *L. lactis* incubated with MSA2::cA, subsequently stored in 10% glycerol for 3 weeks at −80° C.; and (8) TCA-pretreated *L. lactis* incubated with MSA2::cA, subsequently stored in water for three weeks at −80° C. As illustrated, TCA pretreatment improves binding of MSA2::cA to *L. lactis* cells (i.e., compare lanes 3 and 4). Washing with 8 M LiCl and storage in water for 3 weeks at 4° C. has minor effects on the bound MSA2::cA (i.e., compare lane 4 with 5 and 6). Storage at −80° C. has no effect on the bound MSA2::cA (i.e., compare lane 4 with 7 and 8).

TCA-pretreated L. lactis cells with bound MSA2::cA were stored for 3 weeks at +4° C. in demineralized water or at −80° C. in demineralized water with or without 10% glycerol. The samples were analyzed in Western blots. Storing pretreated cells with bound MSA2::cA for 3 weeks in water at +4° C. only resulted in a loss of signal of about 50% (FIG. 13, compare lanes 4 and 6). Whether this loss of signal was due to degradation or due to release of the protein into the water was not determined. Storage at −80° C. with or without 10% glycerol had no effect on the binding (FIG. 13, compare lanes 4, 7 and 8).

In addition, the effects of drying and lyophilization on the binding of MSA2::cA to TCA-pretreated L. lactis cells were studied. Drying of pretreated cells had no observable negative effect on binding of MSA2::cA afterwards. Dried pretreated cells with bound MSA2::cA could be resuspended in water without losing bound fusion protein. This was also observed for lyophilized cells with bound MSA2::cA. Lyophilization of TCA-pretreated cells prior to binding resulted in loss of the binding capacity for MSA2::cA (results not shown).

From these data, it may be concluded that: (i) in spite of the non-covalent character of cA anchor binding to cell walls, the binding is very strong; (ii) cell-free culture supernatants can be stored safely at −20° C.; and (iii) drying of TCA-pretreated cells provides an efficient and simple method for storage of such cells either with or without bound cA-anchor fusions.

EXAMPLE 2

Oral Immunizations of Rabbits with Non-Recombinant *Lactococcus lactis* Preloaded with the *Plasmodium falciparum* Malaria Antigen MSA2 Fused to the Lactococcal AcmA Protein Anchor In Example 1, a technology is described that efficiently binds protein hybrids when externally added to the cell surface of non-recombinant gram-positive bacteria by means of an AcmA-type protein anchor. This technology provides the possibility to provide bacteria or bacterial cell walls with new traits without introducing recombinant DNA into them. The immunogenicity in rabbits of the *Plasmodium falciparum* merozoite surface protein, MSA2 of strain 3D7 (Ramasamy et al. 1999), presented on the cell surface of non-recombinant non-living L. lactis cells as an AcmA anchor fusion protein was investigated.

Materials and Methods.

Bacterial Strains and Growth Conditions. The L. lactis strain which produces MSA2::cA, the strain's growth conditions, the induction for expression, the TCA pretreatment of the L. lactis recipient cells and the binding of MSA2::cA to the cells was described in Example 1 with the following modification: a ratio of 1 (TCA-pretreated cells) to 5 (cell-free culture supernatant with MSA2::cA) was used for binding. An L. lactis NZ9000 strain carrying plasmid pNG3043 was used as a positive control in the immunization experiments (was positive in a previous, unpublished experiment). Plasmid pNG3043 encodes an MSA2 hybrid protein that contains the lactococcal PrtP cell-wall anchoring domain at its C-terminus (MSA2::cP) instead of the AcmA protein anchor. The PrtP cell-wall anchoring domain contains the LPXTG (SEQ ID NO:1) motif that enables a membrane-linked sortase to covalently couple the protein to the cell wall (Navarre and Schneewind 1994). The cP domain used in construct pNG3043 corresponds to nt 6539 to 6914 in Kok et al. (1988). Primers used for the amplification of this fragment were PrtP.cwa.fw3 (5'-ATATAAAGCTTGCAAAGTCT-GAAAACGAAGG (SEQ ID NO:8)) and PrtP.cwa.rev (5'-CCGTCTCAAGCTCACTATTCTTCACGTTGTTTCCG (SEQ ID NO:9)). The primers include restriction endonuclease recognition sites for cloning. Plasmid pNG3043 differs from plasmid pNG3041 in the cell-wall binding domain. Growth conditions and induction of expression of strain NZ9000ΔacmA(pNG3043) were the same as for strain NZ9000ΔacmA(pNG3041).

Rabbit Immunizations. Ten barrier-reared, New Zealand white rabbits obtained from Harlan laboratories, The Netherlands, were used in groups of 2 for experimental immunizations. The care and use of animals were according to WHO guidelines (WHO/LAB/88.1). The rabbits were ear bled prior to immunization to obtain preimmune sera. Details of the rabbits and immunogens are as follows:

Rabbits A1 and A2 were subcutaneously immunized with NZ9000ΔacmA(pNG3041) cells (recombinant, MSA2::cA partly surface anchored).

Rabbits B1 and B2 were subcutaneously immunized with NZ9000ΔacmA (negative control).

Rabbits C1 and C2 were orally immunized with NZ9000ΔacmA(pNG3043) cells (recombinant, MSA2::cP surface anchored).

Rabbits D1 and D2 were orally immunized with NZ9000ΔacmA(pNG3041) cells (recombinant, MSA2::cA surface anchored).

Rabbits E1 and E2 were orally immunized with TCA treated NZ9000ΔacmA to which MSA2::cA had been bound from NZ9000ΔacmA(pNG3041) culture supernatant (non-recombinant, MSA2::cA surface anchored).

Stocks of NZ9000ΔacmA(pNG3043) with MSA2::cP expressed at its surface were stored in aliquots of $10^{11}$ cells in growth medium containing 10% glycerol at −80° C. The cells remain viable under these conditions and retain MSA2 on the surface as demonstrated by immunofluorescence (not shown). The first immunization was carried out with freshly grown bacteria. For subsequent immunizations, stocks of bacteria were freshly thawed, washed and resuspended in buffer at the appropriate concentration for immunizations.

On the other hand, the non-pretreated NZ9000ΔacmA (negative control), the non-pretreated NZ9000ΔacmA (pNG3041) and the TCA-pretreated NZ9000ΔacmA with the externally bound MSA2::cA were prepared daily from fresh cultures.

Subcutaneous injections were performed with a total of $5 \times 10^9$ cells in 100 μL PBS without any adjuvant into two sides on either side of the spine. The subcutaneous injections were repeated two more times at three-week intervals. Prior to oral immunization, the rabbits were deprived of water and food for two to four hours. The rabbits were then fed $5 \times 10^{10}$ cells resuspended in 1 ml of 0.5% sucrose. Each dose was repeated for three successive days to obtain reproducible oral immunization. Altogether, three series of oral immunizations were given at three-week intervals. Adverse effects consequent to the immunizations, including granulomas at the sites of subcutaneous injections, were not observed, indicating that L. lactis was well tolerated by the animals.

Serum Antibody Responses. Rabbits were ear bled two weeks after each immunization to obtain sera for antibody assays. The sera were stored at −20° C. until use. Ten-fold serial dilutions of the antisera in 2% BSA in PBS were used in immunofluorescence assays (IFA) to determine the titer of the antibodies against MSA2 on the surface of 3D7 P. falciparum merozoites. IFA was performed on acetone-methanol fixed late stage 3D7 P. falciparum parasites as previously described (Ramasamy 1987). For detection of antibody isotypes, Oregon Green conjugated goat anti-rabbit Ig (Molecular Probes) was used as the second antibody. For detection of IgG antibodies, a fluorescein conjugated, affinity purified, mouse monoclonal with specificity against rabbit IgG chains (Rockland) was used.

Results and Discussion.

Surface Expression of MSA2 in Different L. Lactis Strains. Coomassie staining of SDS-PAGE gels and fluorescence microscopy were used to determine, in a semi-quantitative way, the number of MSA2 molecules expressed and surface exposed by the recombinant lactococcal strains carrying plasmid pNG3041 or pNG3043 that produce MSA2::cA or MSA2::cP, respectively, and by the non-recombinant TCA-pretreated L. lactis cells to which MSA2::cA had been bound from the outside. The recombinant strains were estimated to produce approximately $1.4 \times 10^5$ molecules of MSA2::cA or MSA2::cP. The surface exposure of MSA2::cA and MSA2::cP differed considerably as shown by fluorescence microscopy in FIG. 14. The non-recombinant TCA-pretreated L. lactis cells with bound MSA2::cA showed a uniform staining of the entire cell surface. However, the semiquantitative SDS-PAGE analysis indicated that about $1 \times 10^4$ molecules of MSA2::cA per cell were represented.

Accordingly, it may be concluded that the number of surface-exposed MSA2::cA and MSA2::cP on the recombinant lactococcal strains is less than 10% of the total number of molecules produced by these strains. The other molecules are most likely trapped in the membrane or the cell wall. Similar observations were made by Norton et al. (1996) for the expression of TTFC fused to the cP cell-wall anchoring domain. In that study, only membrane-associated or cell-wall-associated TTFC could be demonstrated and no surface-exposed TTFC::cP was demonstrated. Thus, it appears that binding from the outside to TCA-pretreated cells is a more efficient method to surface-exposed proteins on L. lactis cells.

Anti-MSA2 Antibody Responses in Orally Immunized Rabbits. Characteristics of the anti-MSA2 antibody response to the immunizations are summarized in Table 2. The oral immunizations with the recombinant L. lactis that produces MSA2::cP (rabbits C1 and C2) were done before (unpublished results) and used as a positive control. In the previous experiment, a similar antibody response was found. The present experiment showed that specific antibodies against near native MSA2 were detectable after two immunizations for group A, D and E rabbits, and that antibody titers increased in all instances after a third immunization. IgG antibodies were predominant after three immunizations in either the subcutaneous or oral route. A comparatively weak anti-MSA2 surface IFA, attributable to the generation of cross-reactive antibodies (as described herein), was also observed after three control subcutaneous immunizations with L. lactis cells alone.

Taken together, the results indicate that: (i) MSA2 produced by lactococcal cells elicits serum antibodies that recognize native P. falciparum parasite MSA2; (ii) MSA2-specific $T_h$ cells are activated through mucosal immunization due to the presence of systemic IgG antibodies (Table 2) that can be boosted (unpublished results); and (iii) oral immunizations with MSA2::cA bound to non-recombinant non-living TCA-pretreated L. lactis cells are as efficient in evoking specific serum antibody responses as the live recombinant strain producing MSA2::cA that was administered subcutaneously or orally, or as efficient as the live recombinant strain producing MSA2::cP that binds MSA2 covalently to its cell wall delivered orally.

Figure 15:
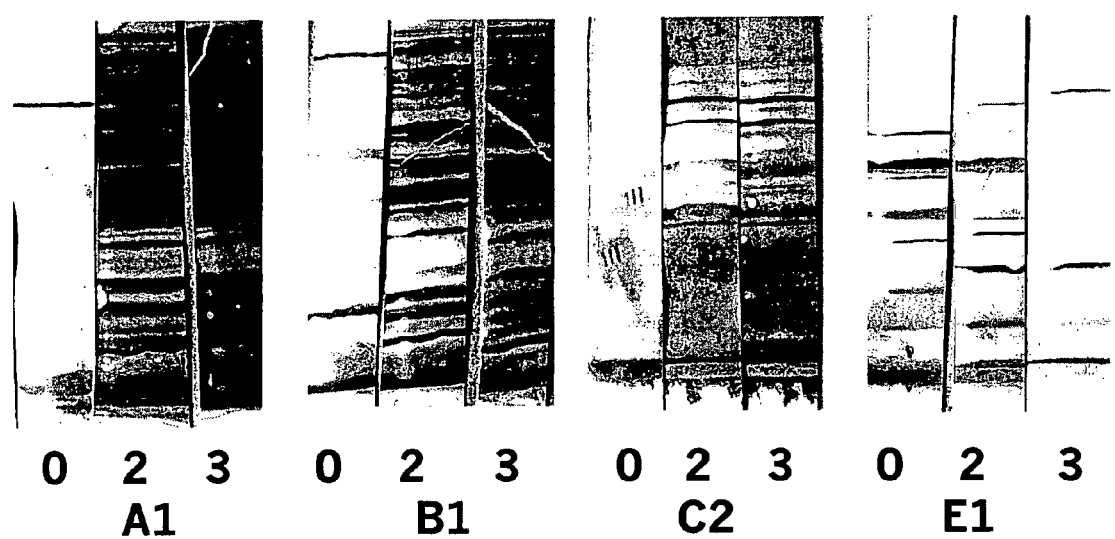
FIG. 15. Western blots of *L. lactis* total protein extracts reacted with rabbit immune serum diluted at 1:100. 0: preimmune serum. 2 and 3: serum after the second and third immunization, respectively. A1: subcutaneously immunized rabbit with NZ9000ΔacmA(pNG3041) cells (recombinant, MSA2::cA surface anchored). B1: subcutaneously immunized rabbit with NZ9000ΔacmA (negative control). C2: orally immunized rabbit with NZ9000ΔacmA(pNG3043) cells (recombinant, MSA2::cP surface anchored). E1: orally immunized rabbit with TCA-pretreated NZ9000ΔacmA to which MSA2::cA had been externally bound (non-recombinant, MSA2::cA surface anchored). The staining bands in the lanes illustrates that *L. lactis* proteins react with the indicated rabbit antiserum. It is visible that the non-recombinant TCA-pretreated strain with bound MSA2::cA (E1) evokes a minimal response to *L. lactis* proteins indicating that the response to the carrier is reduced, while the response to the malaria antigen is not negatively influenced (see, Table 2).

Anti-lactococcal Antibody Responses. Western blots (FIG. 15) demonstrated significant antibody responses against L. lactis antigens after two and three immunizations of the rabbits. The responses were notably greater after subcutaneous (group A and B rabbits) than oral immunization with L. lactis (group C rabbits). Oral immunization with the TCA-pretreated lactococcal cells (group E rabbits) elicited antibodies that reacted at a lower intensity with fewer L. lactis antigens than oral immunization with viable L. lactis cells. This is most likely due to the fact that proteins are removed from the lactococcal cells by the TCA pretreatment (see, Example 1). The lower anti-carrier response observed for the TCA-pretreated (non-recombinant) cells renders this type of delivery vehicle more suitable for repeated immunization strategies than its untreated (recombinant) counterpart.

EXAMPLE 3 pH-Dependent Cell-Wall Binding of AcmA Protein Anchor Homologs and Hybrids

The cell-wall binding domain or anchor of the lactococcal cell-wall hydrolase AcmA includes three repeats of 45 amino acids that show a high degree of homology (Buist et al. 1995). These three repeats belong to a family of domains that meet the consensus criteria as defined in PCT publication WO 99/25836 and can be found in various surface-located proteins in a wide variety of organisms. Another feature that most of these domains have in common is that their calculated pI values are high, approximately 8 or higher (Table 3). The pH used in previous binding experiments with MSA2::cA (i.e., Examples 1 and 2) was approximately 6, indicating that the binding domain was positively charged.

Figure 16:
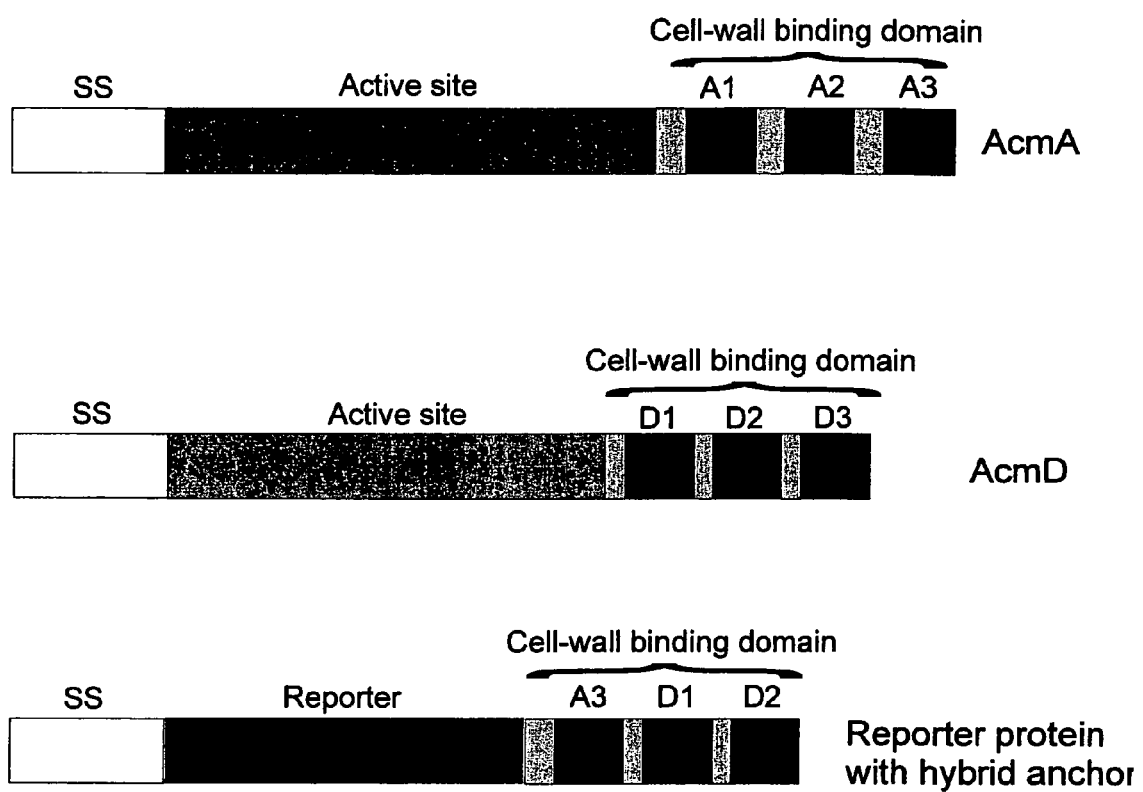
FIG. 16. Schematic representation of the domains in AcmA and AcmD. SS represents signal sequence. Both enzymes include a cell-wall binding domain that includes 3 repeats indicated by A1, 2, 3 and D1, 2, 3. The alignments of these repeats are shown in FIG. 6. In addition, an example of one of the hybrid protein anchors is described in Table 5.

The AcmA protein anchor homolog of the lactococcal cell-wall hydrolase AcmD (cD) (Bolotin et al. 2001) also includes three repeats (FIG. 16) with a calculated pI that is lower (approximately pI 3.8) than that of the cA domain (Table 4). Consequently, the cD anchor was negatively charged at the binding conditions used in Example 1. No binding of the MSA2::cD reporter protein occurred under these conditions as demonstrated herein. Therefore, the influence of the pH during binding of a cD fusion protein (MSA2::cD) was investigated. Furthermore, a hybrid protein anchor including the three cD repeats and one cA repeat that has a calculated pI value that is higher than that of the cD repeats alone was constructed. The hybrid protein anchor showed better binding pH values above the pI of the cD repeats alone, indicating that the pH binding range of AcmA-type protein anchors can be manipulated by using the pI values of the individual repeats in hybrids.

Materials and Methods.

Bacterial strains, growth and induction conditions, TCA pretreatment of *L. lactis* cells, incubation of the MSA2 protein anchor fusion proteins to TCA-pretreated cells, washing conditions, protein gel electrophoresis, Western blotting and immunodetection were the same as described herein with reference to Example 1. The cell-free culture supernatants with MSA2::cA, MSA2::cD or A3D1D2D3 have a pH of approximately 6.2. The influence of pH was examined by adjusting the pH of the cultures by the addition of HCl or NaOH to obtain the required pH.

Plasmid Constructions. The plasmid that expresses the MSA2::cD fusion was described herein with reference to Example 1. Plasmid pPA43 is based on the same expression plasmid and contains an in-frame fusion of the lactococcal signal sequence of Usp45 (ssUsp; van Asseldonk et al. 1990. Gene 95: 155-160), the c-myc epitope for detection purposes, the A3 cA repeat and repeats D1, D2 and D3 of cD. Primers used for cloning A3 were cArepeat3.fw (CCG TCT CCA ATT CAA TCT GCT GCT GCT TCA AAT CC (SEQ ID NO:10)) and cA repeat3.rev (TAA TAA GCT TAA AGG TCT CCA ATT CCT TTT ATT CGT AGA TAC TGA CCA ATT AAA ATA G (SEQ ID NO:11)) (the primers include the A3 specific sequences). The primers used for cloning the three cD repeats were cDrepeat1.fw (CCGTCTCCAATTTCAGGAG-GAACTGCTGTTACAACTAG) (SEQ ID NO:12) and cDrepeat3.rev (TAATAAGCTTAAAGGTCTCCAATTC-CAGCAACTTGCAAAACTTCTCCT AC) (SEQ ID NO:13) (the primers include the cD specific sequences).

Results and Discussion.

Figure 17:
FIG. 17. Western blot showing the effect of pH supernatant on binding of MSA2::cD to TCA-pretreated *L. lactis* cells. As previously described, the Western blot shows the amount of MSA2::cD bound by the cells. In addition, the amount of MSA2::cD that was not bound and remained in the medium after binding is shown. The arrow indicates the expected position for pro-MSA2::cD and the asterisk indicates the position of mature MSA2::cD. Lanes: (1) pH during binding 6.2, cells; (2) pH during binding 6.2, supernatant after binding; (3) pH during binding 3.2, cells; (4) pH during binding 3.2, supernatant after binding; and (5) positive control: *L. lactis*, TCA-pretreated with bound MSA2::cA at pH 6.2. It is visible that MSA2::cD binds better at pH 3.2 than at pH 6.2 (i.e., compare lanes 1 and 3).

Binding of MSA2::cD at Low pH. Since binding of MSA2::cD was not observed at a pH (the pH of the culture medium after growth and induction is about 6.2) higher than the calculated pI for the cD domain (i.e., pI 3.85), binding was studied when the pH of the medium was adjusted to pH 3.2. TCA-pretreated *L. lactis* cells were used as the binding substrate and the relative amounts of bound MSA2::cD were analyzed in Western blots. The amounts of unbound reporter protein remaining in the culture supernatant after binding were also analyzed. FIG. 17 shows a clear increase in bound MSA2::cD when binding is performed at pH 3.2 (compare lanes 1 and 3). At the same time, less unbound reporter protein remained in the supernatant (compare lanes 2 and 4). This result indicates that positive charges are important for binding of cA-type anchoring domains.

Binding of cAcD Hybrid Anchors. Analysis of the pI values of the cA homologs in Table 3 indicates that two classes of repeats can be distinguished: a majority (99 out of 148) of homologs that have a high pI value (>8) and a smaller group (33 out 148), of which cD is a representative, that has pI values lower than 6. Based on the experimental results, it is shown that these types of anchoring domains only bind to bacterial cell walls at a pH that is lower than the anchoring domains pI. Notably, most cell-wall binding domain homologs include repeats with a pI that are representatives of one of the two groups, i.e., only repeats with a high or low pI. Some proteins with cell-wall binding domains, e.g., those of DniR of *Trepanoma pallidum* and an amidase of *Borrelia burgdorferi*, include repeats with high and low pI. Since the binding pH of such "natural hybrid" cell-wall binding domains is below the intermediate pI value of the total number of repeats present in the domain, a hybrid cell-wall protein anchor was constructed using the cA and cD repeats with an intermediate pI value. Table 5 lists the native AcmA and AcmD anchors and a number of examples of cA/cD hybrids. The constructed hybrid protein anchor (A3 D1D2D3) has a calculated pI value of approximately 5.1. A protein anchor including only D1D2D3 shows little binding at a pH above its calculated pI (as described herein). The A3 (pI 10) domain shows similar binding at pH 5 and pH 7.

Figure 18:
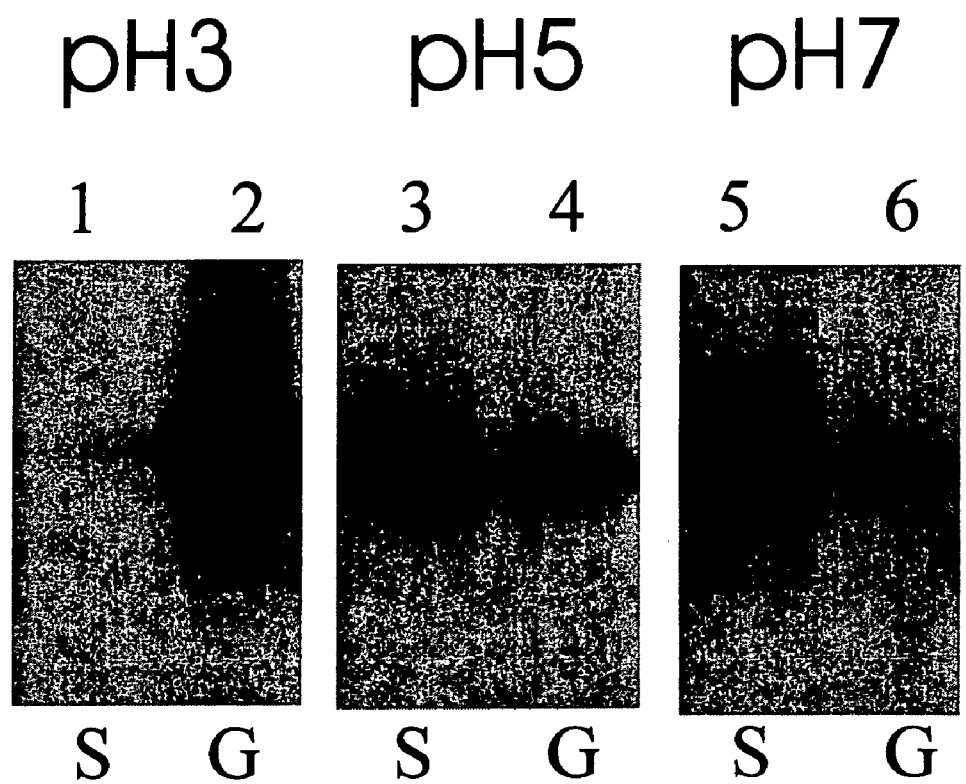
FIG. 18. Western blot of medium supernatant (S) after binding to ghost cells at the indicated pH's and ghost (G) with the bound protein anchor. Lanes 1 and 2 illustrate binding at pH 3; lanes 3 and 4 illustrate binding at pH 5; lanes 5 and 6 illustrate binding at pH 7. The drawing shows considerable binding at pH 5. At pH 5, the native cD anchor (D1D2D3) shows little binding. The addition of the A3 repeat, which has a high pI value, results in increased binding at pH 5.

The binding of the hybrid anchor A3D1D2D3 was tested at pH 3, pH 5 and pH 7. At pH 3, most protein had been bound to the ghost cells (FIG. 18). At pH 5, there was considerable binding (+/−40%), whereas there was only minimal binding at pH 7 (+/−20%). This result indicates the pH range of binding for cD repeats was shifted to higher pH values by the addition of one cA repeat (A3) that caused a shift in calculated pI values of 3.8 to 5.1. The increase of binding at pH 5 for the A3D1D2D3 hybrid cannot be attributed to binding of the A3 repeat alone. If this was the case, then the same level of binding should occur at pH 7 since the A repeats show the same binding at these pH values. In addition, the increased binding at pH 5 is not an additive effect in the sense that an extra binding domain results in increased binding. It has previously been shown that addition of one repeat to the cA anchor did not result in increased binding. The binding at the higher pH values of the A3D1D2D3 repeats, as compared to the D1D2D3 repeats alone, thus may be attributed to the increase in the calculated pI value of the hybrid cA/cD anchor.

This demonstrates that pH binding properties of these types of protein anchors may be manipulated on the basis of the pI values of individual repeats present in the hybrid anchor.

EXAMPLE 4

Induction of Cellular Immune Responses in Mice after Oral Immunizations with Lactococcal Ghosts Displaying the Malaria *Plasmodium falciparum* Antigen MSA2 Fused to the Lactococcal AcmA Protein Anchor Non-genetically modified non-living *Lactococcus lactis* cells (ghosts) preloaded with the *Plasmodium falciparum* MSA2 antigen fused to the AcmA protein anchor (MSA2::cA) were used to orally immunize mice in a similar way as described herein with reference to Example 2. In this experiment, the question of whether immunizations through the oral route with the non-recombinant non-living Ghosts carrying MSA2::cA on their surface (Ghosts-MSA2::cA) can elicit typical Th1-type immune responses, such as IgG2 antibodies and gamma-interferon (γIFN)-producing T cells in the spleen is addressed. These responses are particularly relevant to obtain immunity for pathogens, such as malaria, that undergo stages in their life cycle where they are not in the blood but hide in cells.

Materials and Methods.

Groups of five mice of different strains were used for immunization. The strains of mice used were Balb/c (with the major histocompatibility locus allotype of H2d), C57 Black (H2b), C3H (H2k) and ICR (outbred, i.e., of varying H2 types). Oral immunizations were performed at three weekly intervals. Immunizations were performed with MSA2::cA absorbed onto the surfaces of TCA-treated *Lactococcus lactis* cells (Ghosts-MSA2::cA) or with recombinant *L. lactis* that displayed MSA2 on the surface through the use of a covalently linked cell-wall anchor (*L. lactis*(MSA2::cP)) as described herein with reference to Example 2. The mice were tail bled to obtain serum samples two weeks after the second, third and fourth immunizations. Fecal pellets were collected and extracted to examine intestinal IgA antibody production. The mice were sacrificed at the end of each experiment and the spleens were removed for examining T-cell responses by ELISPOT. MSA2-his tag produced in *E. coli* was used as antigen in the ELISA and ELISPOT assay. The growth of bacterial strains and the preparation of Ghost cells were as described herein with reference to Example 2.

Results and Discussion.

Kinetics and Isotypes of the Serum IgG Antibodies Generated Oral Immunizations. Differences in the kinetics of the antibody response and the isotype distribution were observed between different murine strains. The antibody response was also different when living recombinant *L. lactis* (MSA2::cP) or Ghosts-MSA2::cA were used as immunogens. With Ghosts-MSA2::cA, high serum antibody levels were detectable in the C3H mice after two immunizations. IgG antibodies were detectable in all four murine strains after three and four immunizations. Antibody titers were highest in C3H mice. IgG antibodies that reacted with native MSA2 on parasites were detected in the sera of immune mice by fluorescence microscopy (IFA) confirming that the immunizing form of the protein elicits biologically relevant antibodies. Control immunizations were performed with Ghosts alone where no MSA2-specific antibodies were elicited. In parallel experiments using MSA2cP as the immunogen, high serum IgG antibody levels were only seen with Balb/c mice after two immunizations. After three and four immunizations, good antibody responses developed in C3H mice. Antibody titers were highest in Balb/c mice.

Significant differences existed between the strains in the isotypes of the elicited serum IgG antibodies in response to immunization with Ghosts-MSA2::cA. Balb/c mice showed higher levels of IgG2a and IgG2b antibodies, some IgG3 antibodies and negligible IgG1, which demonstrates a possible Th1 bias. On the other hand, C57 Black and C3H mice had high IgG1, IgG2a and IgG2b, and lower IgG3 antibodies to MSA2, which is more characteristic of a mixed Th1 and Th2 response. ICR mice, as expected, showed a range of responses. Some ICR mice had the Balb/c and others the C3H/C57 Black pattern of IgG isotypes.

Formation of Mucosal Antibodies. IgA antibodies were detected by ELISA in the fecal pellets of the ICR and Balb/c mice, but were not detected in C3H or C57 Black mice when immunization was performed with living recombinant *L. lactis*(MSA2::cP) or Ghost-MSA2::cA.

T-Cell Responses. The increase of the intensity of the IgG ELISA reactions seen in mice immunized with Ghosts-MSA2::cA with each immunization demonstrates that boosting takes place and that a Th-dependent antibody response exists in these animals. The IgG isotype distribution further confirms this conclusion. Therefore, Th cells are generated in ICR, Balb/c, C57 Black and C3H mice.

The ELISPOT assay for detecting gamma-interferon (γIFN) producing cells detects mainly CD8$^+$ Tc cells, which are an important component of the immune response to many pathogens, including malaria parasites. His-tagged MSA2 produced in *E. coli* was used as antigen in the assay. MSA2-specific γIFN producing cells could be detected in the spleens of Balb/c, C57 Black and C3H mice that were immunized with Ghosts-MSA2::cA. MSA2-specific γIFN producing cells were not observed in the spleens of control mice immunized with Ghosts alone or with the living recombinant *L. lactis*(MSA2-cP). The latter group showed a high level of non-specific γIFN producing cells. The high background observed may be due to ongoing inflammation.

The sensitization of MSA2-specific Tc cells in the spleen after immunization with the non-recombinant non-living *L. lactis* Ghost system carrying a foreign protein is a novel finding which is applicable to malaria since protection against sporozoite-infection is associated with γIFN producing cells being produced in the spleen.

The non-recombinant non-living Ghost system can be used in oral immunizations to elicit typical Th1-type immune responses. These types of responses are particularly relevant to obtain immunity for pathogens that undergo stages in their life cycle where the pathogens are not in the blood but rather hide in cells. The responses are more pronounced and more specific for the Ghost system than for the living recombinant system. The Ghost system has the additional advantage of eliminating the risk of spreading recombinant DNA into the environment.

EXAMPLE 5

Protection of Mice for Lethal *Streptococcus pneumoniae* Challenge after Oral Immunizations with Lactococcal Ghosts Preloaded with PpmA Antigen Fused to the Lactococcal AcmA Protein Anchor

*Streptococcus pneumoniae* is the leading etiological agent of severe infections including septicemia, meningitis, pneumonia, and otitis media. Recent studies on the molecular epidemiology and pathogenesis of *S. pneumoniae* have identified pneumococcal proteins with vaccine potential. One of these proteins, the protease maturation protein PpmA, has been shown to elicit immune protective potential in a mouse pneumonia model.

The non-genetically modified lactococcal ghosts have been shown to be an efficient carrier for use in oral immunizations of rabbits and mice in order to elicit strong anti-malaria immune responses. The construction of lactococcal ghosts that display the *S. pneumoniae* PpmA fused to the lactococcal AcmA cell-wall binding domain on their surface is described herein. The ability of these ghosts to protect orally immunized mice from a lethal nasal dose of *S. pneumoniae* was investigated.

Materials and Methods.

Bacterial Strains and Growth Conditions. *L. lactis* was grown and ghost cells were prepared as described herein with reference to Example 1. *S. pneumoniae* was grown as described before (Gingles et al. 2001, *Infect. Immun.* 69: 426-434).

Construction of ppmA Protein Anchor Fusion Expression Plasmid. The expression plasmid for ppmA protein anchor fusion (PpmA::cA) was substantially similar to the expression plasmid for the MSA2 protein anchor fusion as described herein with reference to Example 2. For the secretion of PpmA::cA, the secretion signal sequence of the Usp45 protein (ssUsp) of *L. lactis* (van Asseldonk et al. 1990. Gene 95: 155-160) was used. The PpmA gene was cloned by PCR using primers ppmA.1 (CGGTCTCACATGTCGAAAGGGTCAGAAGGTG CAGACC) (SEQ ID NO:14) and ppmA.2 (CGGTCTCGAATTGCTTCGTTTGATGTAC-TACTG CTTGAG) (SEQ ID NO:15) resulting in plasmid pPA32 which contains ppmA as an in-frame fusion with ssUsp45 and the protein anchor (ssUsp::ppmA::cA). Expression of the fusion gene results in the secreted product PpmA::cA. The primers include an Eco31I restriction enzyme recognition site that was used for digestion of the PCR fragment. This restriction digest produced NcoI and EcoRI sticky ends which were used for cloning. The primers also included the ppmA sequences. Chromosomal DNA of *S. pneumoniae* strain D39 was used as a template for the PCR reactions.

Preparation of the Vaccine. Three liters of M17 medium with PpmA::cA, obtained after growth and used to induce producer cells for expression of *L. lactis* (pPA32) was centrifuged and filter sterilized (0.2 µm) to remove the producer cells. Ghost cells were prepared from 0.5 liter of *L. lactis* NZ9000(ΔacmA). After binding, the ghost cells with PpmA::cA (Ghosts-PpmA::cA) were isolated by centrifugation and washed with PBS. The ghost cells were stored in PBS in aliquots of $2.5 \times 10^{10}$ Ghosts/ml at $-80°$ C. Two control groups included: (i) Ghosts without bound PpmA::cA; for the sample preparation, the same amounts of ghost cells were used and the same centrifugation and washing steps were performed, but the binding step was omitted; and (ii) soluble PpmA was isolated as a his-tagged fusion.

Mice Immunizations. Groups of 10 mice (CD-1) were used in the immunizations. Oral doses included $5 \times 10^9$ Ghosts with or without PpmA::cA (50 µg) or 50 µg soluble PpmA in PBS. Nasal doses included $5 \times 10^8$ Ghosts with or without PpmA::cA (5 µg) or 5 µg soluble PpmA. $10^8$ Ghosts-PpmA::cA (1 µg) were subcutaneously injected. For intranasal immunizations, the mice were slightly anesthetized with Isofluorane.

Intranasal Challenge. The groups of orally immunized mice were intranasally challenged 14 days after the last booster immunization with a dose of $10^6$ colony forming units (CFU) *S. pneumoniae* D39 as described (Kadioglu et al. 2000, *Infect. Immun.* 68: 492-501). Mice were monitored after the challenge for visible clinical symptoms for 7 days, at which point the experiment was ended. Mice that were alive after 7 days were considered to have survived the pneumococcal challenge and mice that became moribund during the 7-day period were judged to have reached the endpoint of the assay. The time the animal became moribund was recorded, and the animal was sacrificed by cervical dislocation.

ELISA Analysis. Serum samples were taken from each mouse before the intranasal challenge and stored at $-20°$ C. before use. Microtiter plates were coated with 100 µg PpmA/ml in 0.05 carbonate buffer. Serial 10-fold dilutions of pooled serum of each group were incubated on the plates as described (Gingles et al. 2001, *Infect. Immun.* 69: 426-434). Anti-mouse immunoglobulin-horseradish peroxidase conjugate was used for detection and the absorbance was measured at 492 nm.

Results and Discussion.

Figure 19:
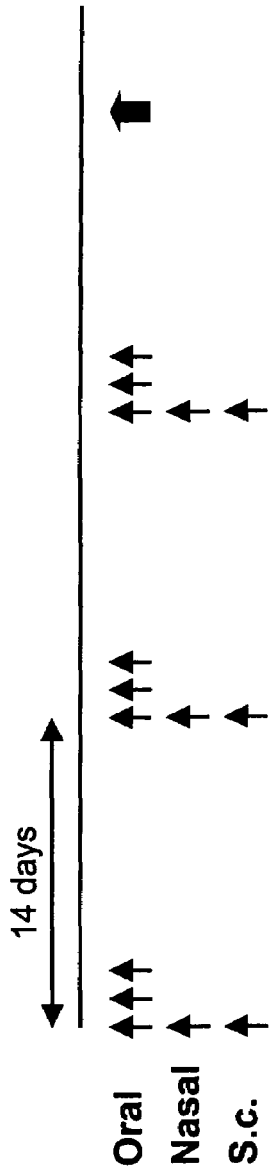
FIG. 19. Immunization schedule. Mice immunizations were started at day 1 and repeated after 14 and 28 days. A lethal nasal challenge with *S. pneumoniae* was given 14 days after the last oral immunization. S.c. represents subcutaneous immunization.
Figure 20:
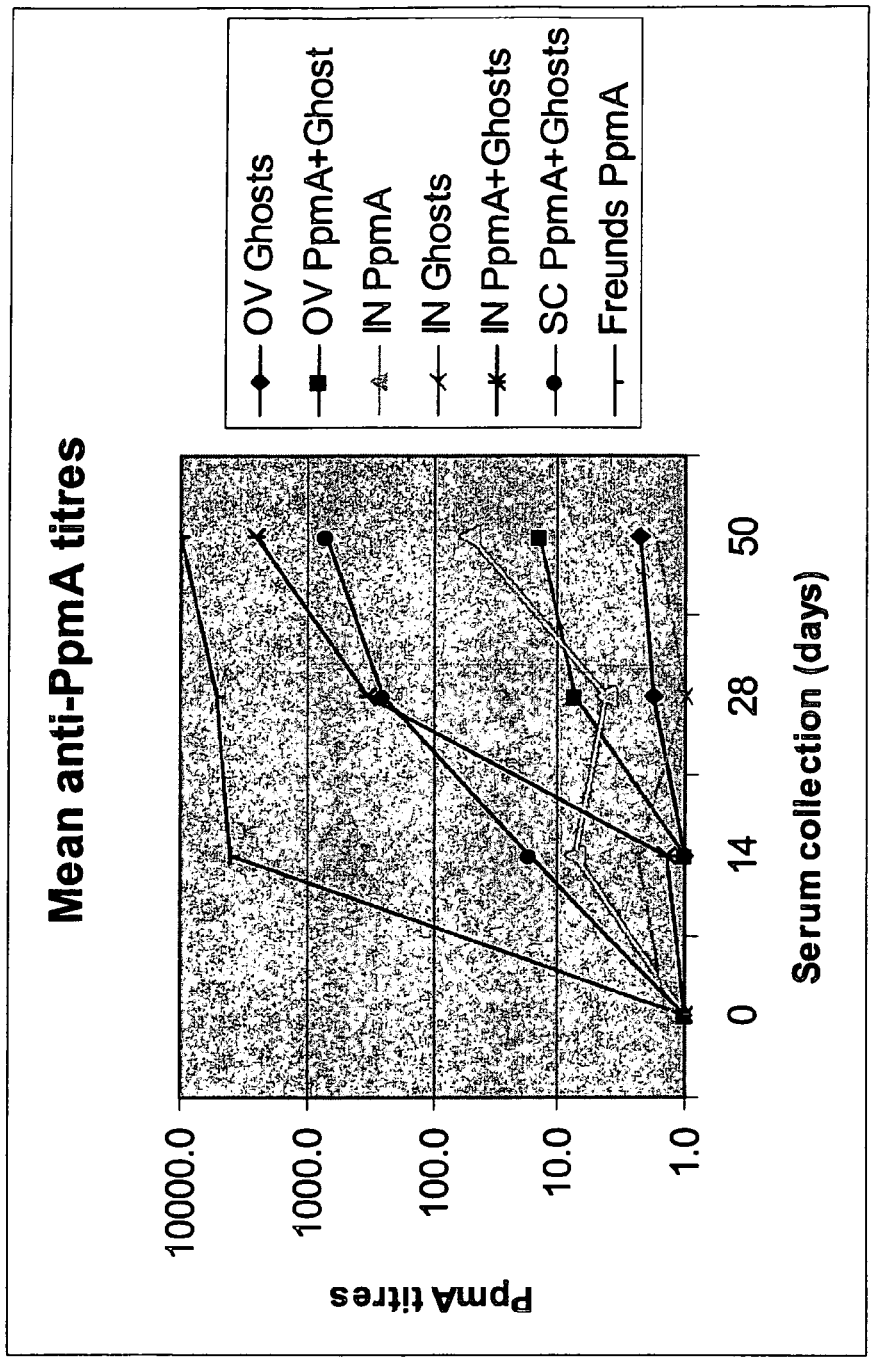
FIG. 20. Serum antibody response. Mean anti-PpmA serum antibody titers. OV represents orally immunized; IN represents intranasally immunized; SC represents subcutaneously immunized; Freund's PpmA refers to soluble PpmA subcutaneously administered with Freund's complete adjuvants. High titers were obtained with the intranasally and subcutaneously administered Ghosts-PpmA::cA.

Serum Antibody Response. Mice were immunized orally, nasally and subcutaneously according to the scheme shown in FIG. 19. Anti-PpmA antibody titers in the blood serum were determined for each group by ELISA assays. The results are given in FIG. 20. As expected, ghosts alone administered orally or nasally, OV Ghosts or IN Ghosts, respectively, did not induce anti-PpmA antibodies. Soluble PpmA given by the nasal route resulted in only a low anti-PpmA antibody titer, which agrees with the general findings that soluble antigens are not very immunogenic when given by the mucosal routes. Ghosts-PpmA::cA provided by the oral route (OV PpmA+ Ghost) induced only a low level of anti-PpmA serum antibodies. This contrasts the results for the oral immunization experiments described herein with reference to Examples 2 and 4 with MSA2::cA. However, the contrast may be antigen-type related.

Intranasal administration of Ghosts-PpmA::cA resulted in a high titer of anti-PpmA antibodies (IN PpmA+Ghosts). A high titer was also obtained by subcutaneous administration of Ghosts-PpmA::cA. These titers were lower by a factor of 5 to 10 when compared to soluble PpmA that was subcutaneously administered and formulated with the strong Freund's complete adjuvant (Peter Adrian, Erasmus University Rotterdam, The Netherlands, unpublished results). In addition, the Freund's PpmA vaccine contained 50 µg PpmA per dose, whereas the intranasally administered Ghosts-PpmA:cA contains only 5 µg/dose and the subcutaneous Ghost-PpmA::cA vaccine contains only 1 µg PpmA/dose. This result demonstrates the adjuvant effect of the ghost cells. Side effects of the orally, nasally or subcutaneously administered ghosts were not observed, which is in contrast to the severe side effects that are usually seen with the use of Freund's adjuvants.

The results demonstrate that high titer serum antibodies can be obtained by the mucosal route of administration. These data also show that ghost cells may be safely used in traditionally injected vaccines without side effects in order to induce high titer serum antibodies.

Figure 21:
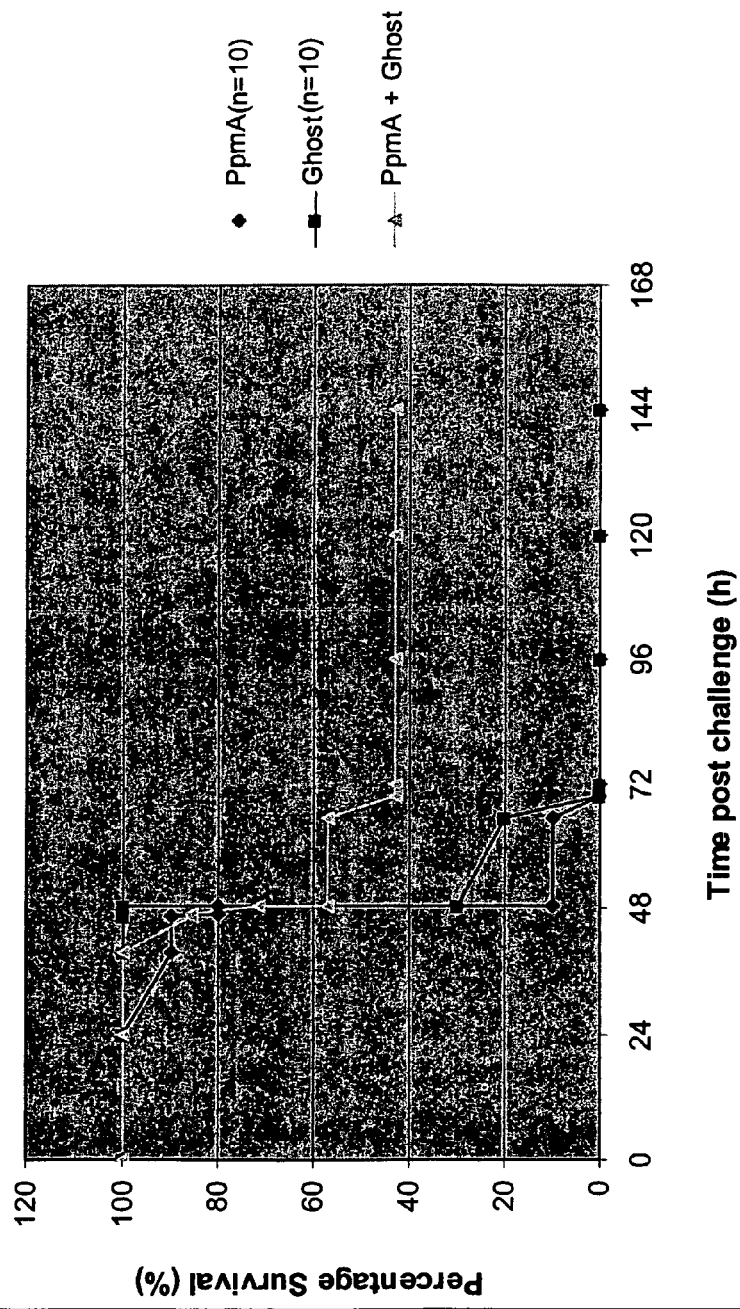
FIG. 21. Survival times. The orally vaccinated mice were challenged with a lethal dose of *S. pneumonia*. Mice vaccinated with soluble PpmA or Ghost alone died within 72 hours. Forty percent of the mice immunized with Ghosts-PpmA::cA survived the challenge, indicating they were protected by the vaccination.

Protection Against Challenge. The mice orally immunized with soluble PpmA, Ghosts alone or Ghosts-PpmA::cA were challenged 14 days post-immunization with a lethal intranasal dose of *S. pneumoniae*. The mice immunized with soluble PpmA or Ghosts alone died within 72 hours after challenge. The group immunized with Ghosts-PpmA::cA showed a survival rate of 40% (FIG. 21). These results show that mucosal immunization of mice with Ghosts-PpmA induces protective immunity against a lethal *S. pneumoniae* challenge. In conclusion, the non-recombinant non-living Ghost system may be used to elicit high titer serum antibodies and the mucosal route of administration may be used to obtain protective immunity against a mucosally acquired pathogen.

TABLE 1

Effect of different pretreatments of *L. lactis* on binding of MSA2::cA.

| Treatment | Signal on Western blot |
|---|---|
| H₂O | − |
| 10% TCA (0.6M) | ++++ |
| 0.6M HAc | ++++ |
| 0.6M HCl | ++++ |
| 0.6M H₂SO₄ | ++++ |
| 0.6M TFA | ++++ |
| 0.6M MCA | ++++ |
| Phenol | ++ |
| 4M GnHCl | ++ |
| 37% formaldehyde | ++ |
| CHCl₃/MeOH | ++ |
| 10% SDS | + |
| 10% DMF | + |
| 10% DMSO | + |
| 25 mM DTT | + |
| 0.1% NaHClO* | − |
| Hexane | − |
| Lysozyme* | − |

*Lysis of cells occurred during treatment or washing steps.

TABLE 2

MSA2 antibody titers of rabbit serum determined by IFA on *Plasmodium falciparum* 3D7 asexual blood stage parasites.

| Rabbit serum | Immunogen | Immunization | | | |
|---|---|---|---|---|---|
| | | P | $2^{nd}$ | $3^{rd}$ | $3^{rd}$ IgG |
| A1 | s.c. *L. lactis* [MSA2::cA] | 0 | 2 | 4 | 4 |
| A2 | s.c. *L. lactis* [MSA2::cA] | 0 | 2 | 5 | 5 |
| B1 | s.c. *L. lactis* | 0 | 0 | 1 | n.d. |
| B2 | s.c. *L. lactis* | 0 | 0 | 1 | n.d. |
| C1 | oral *L. lactis* [MSA2::cP] | 0 | 3 | 5 | 5 |
| C2 | oral *L. lactis* [MSA2::cP] | 0 | 2 | 5 | 5 |
| D1 | oral *L. lactis* [MSA2::cA] | 0 | 2 | 4 | 5 |
| D2 | oral *L. lactis* [MSA2::cA] | 0 | 2 | 4 | 5 |
| E1 | oral TCA *L. lactis* + MSA2::cA | 0 | 2 | 5 | 5 |
| E2 | oral TCA *L. lactis* + MSA2::cA | 0 | 2 | 5 | 4 |

*L. lactis* strain used: NZ9000ΔacmA (lactococcal cells lacking the cell wall hydrolase AcmA).

*L. lactis* [MSA2::cA] and *L. lactis* [MSA2::cP] are the recombinant strains with surface-expressed MSA2, cell wall anchored through the non-covalent AcmA binding domain (cA) or the covalent PrtP anchoring domain (cP), respectively.

TCA *L. lactis* + MSA2::cA are the non-recombinant TCA-pretreated lactococcal cells to which MSA2::cA had been bound externally.

P: pre-immune serum.

S.C.: subcutaneous injection.

Titers are expressed as the negative logarithms of the lowest ten-fold dilution of sera giving a detectable reaction on the merozoite surface. The last column represents the IgG fraction of the antibody response.

0: indicates no detectable reaction at a 1:10 dilution of the serum.

n.d.: not done.

TABLE 3

AcmA cell wall binding domain homologs and their calculated pI values.
(the pI values are indicated directly behind the amino acid sequences)

| Organism | Gene | Sequence | | pI | Range | | Acc. | Type |
|---|---|---|---|---|---|---|---|---|
| Lactococcus lactis | *acmA | YTVKSGDTLWGISQRYGISVAQIQSAN NLKST IIYIGQKLVLT | SEQ ID NO:16 | 9.75 | 245-287 | (33) | 437 U1769600 | muramidase |
| | | VKVKSGDTLWALSVKYKTSIAQLKSWN HLSSD TIYIGQNLIVS | SEQ ID NO:17 | 9.64 | 321-363 | (31) | | |
| | | HKVVKGDTLWGLSQKSGSPIASIKAWN HLSSD TILIGQYLRIK | SEQ ID NO:18 | 10.06 | 395-437 | | | |
| | *acmD | YKVQEGDSLSAIAAQYGTTVDALVSAN SLENANDIHVGEVLQVA | SEQ ID NO:19 | 4.15 | 194-237 | | QGCI25 | |
| | | YTVKSGDSLYSIAEQYGMTVSSLMSAN GIYDVNSMLQVGQVLQVTV | SEQ ID NO:20 | 3.78 | 258-303 | | | |
| | | YTIQNGDSIYSIATANGMTADQLAALN GFGIND MIHPGQTIRI | SEQ ID NO:21 | 4.15 | 319-361 | | | |
| ØTuc2009 | *lys | YVVKQGDTLSGIASNWGTNWQELARQN SLSNPNMIYAGQVISFT | SEQ ID NO:22 | 6.31 | 332-375 | (10) | 428 L31364 | glycosidase (muramidase) |
| | | YTVQSGDNLSSIAILLGTTVQSLVSMN GISNPNLIYAGQTLNY | SEQ ID NO:23 | 3.45 | 386-428 | | | |
| Ø-LC3 | *lysB | YIVKQGDTLSGIASNLGTNWQELARQN SLSNPNMIYSGQVISLT | SEQ ID NO:24 | 6.31 | 333-376 | (10) | 429 U04309 | muramidase |
| | | YTVQSGDNLSSIARRLGTTVQSLVSMN GISNPNLIYAGQTLNY | SEQ ID NO:25 | 8.79 | 387-429 | | | |
| Enterococcus faecalis | *autolysin | YTVKSGDTLNKIAAQYGVSVANLRSWN GISGD LIFVGQKLIVK | SEQ ID NO:26 | 9.74 | 363-405 | (25) | 671 P37710 | muramidase |
| | | YTVKSGDTLNKIAAQYGVTVANLRSWN GISGD LIFVGQKLIVK | SEQ ID NO:27 | 9.74 | 431-473 | (25) | | |
| | | YTIKSGDTLNKIAAQYGVSVANLRSWN GISGD LIFAGQKIIVK | SEQ ID NO:28 | 9.74 | 499-541 | (25) | | |
| | | YTIKSGDTLNKISAQFGVSVANLRSWN GIKGD LIFAGQTIIVK | SEQ ID NO:29 | 9.85 | 567-609 | (19) | | |
| | | HTVKSGDSLWGLSMQYGISIQKIKQLN GLSGD TIYIGQTLKVG | SEQ ID NO:30 | 9.35 | 629-671 | | | |

TABLE 3-continued

AcmA cell wall binding domain homologs and their calculated pI values.
(the pI values are indicated directly behind the amino acid sequences)

| Organism | Gene | Sequence | SEQ ID NO | pI | Range (count) | Accession | Description |
|---|---|---|---|---|---|---|---|
| hirae | *mur2 | YTVKSGDSVWGISHSFGITMAQLIEWN NIKNN FIYPGQKLTIK | SEQ ID NO:31 | 9.35 | 257-299 (38) | P39046 | muramidase |
| | | YTVKSGDSVWKIANDHGISMNQLIEWN NIKNN FVIPGQQLVVS | SEQ ID NO:32 | 7.14 | 338-380 (33) | | |
| | | YTVKAGESVWSVSNKFGISMNQLIQWN NIKNN FIYPGQKLIVK | SEQ ID NO:33 | 9.91 | 414-456 (32) | | |
| | | YTVKAGESVWGVANKNGISMNQLIEWN NIKNN FIYPGQKLIVK | SEQ ID NO:34 | 9.64 | 489-531 (33) | | |
| | | YTVKAGESVWGVANKHHITMDQLIEWN NIKNN FIYPGQEVIVK | SEQ ID NO:35 | 7.31 | 565-607 (15) | | |
| | | YTVKAGESVWGVADSHGITMNQLIEWN NIKNN FIYPGQQLIVK | SEQ ID NO:36 | 7.15 | 623-665 | | |
| Listeria monocytogenes | *P60 | VVVEAGDTLWGIAQSKGTTVDAIKKAN NLTTD KIVPGQKLQVN | SEQ ID NO:37 | 8.61 | 30-72 (130) | P21171 | adherence and invasion protein P60 |
| | | HAVKSGDTIWALSVKYGVSVQDIMSWN NLSSS SIVGQKLAIK | SEQ ID NO:38 | 9.35 | 203-245 | | |
| innocua | *P60 | VVVEAGDTLWGIAQSKGTTVDAIKKAN NLTTD KIVPGQKLQVN | SEQ ID NO:39 | 8.61 | 30-72 (129) | Q01836 | adherence and invasion protein P60 |
| | | HNVKSGDTIWALSVKYGVSVQDIMSWN NLSSS SIVGQKPAIK | SEQ ID NO:40 | 8.35 | 201-243 | | |
| ivanovii | *P60 | VVVEAGDTLWGIAQDKGTTVDALKKAN NLTSD KIVPGQKLQIT | SEQ ID NO:41 | 6.35 | 30-72 (125) | Q01837 | adherence and invasion protein P60 |
| | | YTVKSGDTIWALSSKYGTSVQNIMSWN NLSSS SIVGQVLAVK | SEQ ID NO:42 | 9.37 | 198-240 (73) | | |
| | | YTVKSGDTLSKIATTFGTTVSKIKALN GLNSD NLQVGQVLKVK | SEQ ID NO:43 | 9.89 | 314-356 | | |
| seeligeri | *P60 | VVVEAGDTLWGIAQDNGTTVDALKKAN KLTTD KIVPGQKLQVT | SEQ ID NO:44 | 6.35 | 30-72 (127) | Q01838 | adherence and invasion protein P60 |
| | | HTVKSGDTIWALSVKYGASVQDLMSWN NLSSS SIVGQNIAVK | SEQ ID NO:45 | 8.64 | 200-242 (77) | | |
| | | YTVKSGDTLGKIASTFGTTVSKIKALN GLTSD NLQVGDVLKVK | SEQ ID NO:46 | 9.62 | 320-362 | | |

TABLE 3-continued

AcmA cell wall binding domain homologs and their calculated pI values.
(the pI values are indicated directly behind the amino acid sequences)

| Organism | Gene | Sequence | SEQ ID NO | pI | Range | Acc. No. | Description |
|---|---|---|---|---|---|---|---|
| welshimeri | *P60 | VVVEAGDTLWGIAQSKGTTVDALKKAN NLTSD KIVPGQKLQVT | SEQ ID NO:47 | 8.61 | 30-72 (125) | 524 M80348 | adherence and invasion protein P60 |
| | | HTVKSGDTIWALSVKYGASVQDLMSWN NLSSS SIVVGQKIAVK | SEQ ID NO:48 | 9.35 | 198-240 (75) | | |
| | | YTVKSGDSLSKIANTFGTSVSKIKALN NLTSD NLQVGTVLKVK | SEQ ID NO:49 | 9.89 | 316-358 | | |
| grayi | *P60 | VVVASGDTLWGIASKTGTTVDQLKQLN KLDSD RIVPGQKLTIK | SEQ ID NO:50 | 9.42 | 30-72 (104) | 511 Q01835 | adherence and invasion protein P60 |
| | | YKVKSGDTIWALSVKYGVPVQKLIEWN NLSSS SIVVGQTIAVK | SEQ ID NO:51 | 9.57 | 177-219 (79) | | |
| | | YKVQNGDSLGKIASLFKVSVADLTNWN NLNATITIYAGQELSVK | SEQ ID NO:52 | 8.59 | 299-342 | | |
| Haemophilus influenzae | *amiB | HIVKKGESLGSLSNKYHVKVSDIIKLN QLKRK TLWLNESIKIP | SEQ ID NO:53 | 10.11 | 294-336 | 432 P44493 | N-acetylmuramoyl-L-alanine amidase |
| | | HKVTKNQTLYAISREYNIPVNILLSLN PHLKNG KVITGQKIKLR | SEQ ID NO:54 | 10.49 | 387-430 | | |
| | *yebA | YTVTEGDTLKDVLVLSGLDDSSVQPLI ALDPELAHLKAGQQPYWI | SEQ ID NO:55 | 3.87 | 131-174 | 475 P44693 | homologous to endopeptidase of Staphylococcus |
| | lppB | YKVNKGDTMPLIAYLAGIDVKELAALN NLSEPNYNLSLGQVLKIS | SEQ ID NO:56 | 6.40 | 147-190 | 405 P44833 | outer membrane lipoprotein |
| somnus | lppB | YKVRKGDTMFLIAYISGMDIKELATLN NMSEPYHLSIGQVLKIA | SEQ ID NO:57 | 8.56 | 120-164 | 279 L10653 | outer membrane lipoprotein |
| Helicobacter pylori | dniR | HVVLPKETLSSIAKRYQVSISNIQLAN DLKDS NIFIHQRLIIR | SEQ ID NO:58 | 10.02 | 319-361 | 372 AE000654 | regulatory protein DniR |
| Pseudomonas aeruginosa | lppB | YIVRRGDTLYSIAFRFGWDWKALAARN GIAPPYTIQVGQAIQFG | SEQ ID NO:59 | 10.06 | 69-113 | 297 P45682 | Lipoprotein |
| Putida | nlpD | YIVKPGDTLFSIAFRYGWDYKELAARN GIPAPYTIRPGQPIRFS | SEQ ID NO:60 | 9.77 | 44-87 | 244 Y19122 | lipoprotein |
| Sinorhizobium meliloti | nlpD | IMVRQGDTVVLARRFGVPEKEILKAN GLKSASQVEPGQRLVIP | SEQ ID NO:61 | 10.27 | 166-209 | 512 U81296 | Lipoprotein |

TABLE 3-continued

AcmA cell wall binding domain homologs and their calculated pI values.
(the pI values are indicated directly behind the amino acid sequences)

| Organism | gene | Sequence | SEQ ID NO | pI | Range | Length | Accession | Description |
|---|---|---|---|---|---|---|---|---|
| Synechocystis sp. | nlpD | HQVKEGESLWQISQAFQVDAKAIALAN SISTDTELQAGQVLNIP | SEQ ID NO:62 | 4.38 | 87-130 | 715 | D90915 | Lipoprotein |
| | slr0878 | HVVKAGETIDSIAAQYQLVPATLISVN NQLSSGQVTPGQTLIP | SEQ ID NO:63 | 5.41 | 4-47 | 245 | D90907 | Hypothetical protein |
| Aquifex aeolicus | nlpDl | YKVKKGDSLWKIAKEYKTSIGKLLELN PKLKNRKYLRPGEKICLK | SEQ ID NO:64 | 10.08 | 26-70 (24) | 349 | AE000700 | Lipoprotein |
| | | YRVKRGDSLIKIAKKFGVSVKEIKRVN KLKGN RIVVGQKLKIP | SEQ ID NO:65 | 10.95 | 95-137 (37) | | | |
| | | YRVRRGDTLIKIAKRFRTSVKEIKRIN RLKGN LIRVGQKLKIP | SEQ ID NO:66 | 12.11 | 174-216 | | | |
| Volvox carteri | | YTIQPGDTFWAIAQRRGTTVDVIQSLN PGVVPTRLQVGQVINVP | SEQ ID NO:67 | 9.03 | 42-85 | 309 | AF058716 | chitinase |
| f. nagariensis | | YTIQPGDTFWAIAQRRGTTVDVIQSLN PGVNPARLQVGQVINVP | SEQ ID NO:68 | 9.03 | 106-149 | | | |
| Staphylococcus aureus | ProtA | HVVKPGDTVNDIAKANGTTADKIAADN KLADKNMIKPGQELVVD | SEQ ID NO:69 | 5.58 | 431-474 | 524 | A04512 | protein A |
| | lytN | YTVKKGDTLSAIALKYKTTVSNIQNTN NIANPNLIFIGQKLVP | SEQ ID NO:70 | 10.03 | 177-220 | 383 | AF106851 | autolysin homolog |
| Colletotrichum | cih1 | HKVKSGESLTTIAEKYDTGICNIAKLN NLADPNFIDLNQDLQIP | SEQ ID NO:71 | 4.76 | 110-153 (31) | 230 | AJ001441 | glycoprotein |
| lindemuthianum | | YSVVSGDTLTSIAQALQITLQSLKDAN PGVVPEHLNVGQKLNVP | SEQ ID NO:72 | 5.46 | 185-228 | | | |
| Chlamydophila | amiB | IVYREGDSLSKIAKKYKLSVTELKKIN KLDSD AIYAGQRLCLQ | SEQ ID NO:73 | 9.46 | 159-201 | 205 | AE001659.1 | N-Acetylmuramoyl-L-Ala Amidase |
| Pneumoniae | CPn0593 | YVVQDGDSLWLIAKRFGIPMDKIIQKN GLNHH RLFPGKVLKLIP | SEQ ID NO:74 | 10.01 | 316-358 | 362 | AE001643 | Muramidase |
| | NlpD | VVVKKGDFLERIARANHTTVAKLMQIN DLTTT QLKIGQVIKVP | SEQ ID NO:75 | 10.17 | 124-166 | 233 | AE001670 | Muramidase |
| | | YIVQEGDSPWTIALRNHIRLDDLLKNN DLDEYKARRLKPGDQLRIR | SEQ ID NO:76 | 8.64 | 188-233 | | | |
| Chlamydia trachomatis | NlpD | VIVKKGDFLERIARSNHTTVSALMQLN DLSST QLQIGQVLRVP | SEQ ID NO:77 | 9.99 | 138-180 | 245 | AE001348 | Muramidase |

TABLE 3-continued

AcmA cell wall binding domain homologs and their calculated pI values.
(the pI values are indicated directly behind the amino acid sequences)

| Organism | Gene | Sequence | SEQ ID | pI | Range | Length | Accession | Description |
|---|---|---|---|---|---|---|---|---|
| | | YVVKEGDSPWAIALSNGIRLDELLKLN GLDEQKARRLRPGDRLRIR | SEQ ID NO:78 | 10.00 | 200-245 | | | |
| | papQ | HIVKQGETLSKIASKYNIPVVELKKLN KLNSD TIFTDQRIRLP | SEQ ID NO:79 | 9.89 | 155-197 | 200 | AE001330 | |
| Prevotella intermedia | phg | HTVRSNESLYDISQQYGVRLKNIMKAN RKIVKRGIKAGDRVVL | SEQ ID NO:80 | 10.72 | 266-309 | 309 | AF017417 | hemagglutinin |
| Leuconostoc oenos Ø10MC | lys | YTVQSGDTLGAIAAKYGTTYQKLASLN GIGSPYIIIPGEKLKVS | SEQ ID NO:81 | 9.23 | 335-378 | 432 | | endolysin |
| | | YKVASGDTLSAIASKYGTSVSKLVSLN GLKNANYIVGENLKIK | SEQ ID NO:82 | 9.68 | 389-432 | | | |
| Oenococcus oeni Øfog44 | Lys44 | YTVRSGDTLGAIAAKYGTTYQKLASLN GIGSPYIIIPGEKLKVS | SEQ ID NO:83 | 9.58 | 335-378 | 432 | AF047001 | Lysin |
| | | YKVASGDTLSAIASKYGTSVSKLVSLN GLKNANYIVGQTLRIK | SEQ ID NO:84 | 9.95 | 389-432 | | | |
| Thermotoga maritime | TM0409 | YKVQKNDTLYSISLNFGIGSPSLLLDWN PGLDPHSLRVGQEIVIP | SEQ ID NO:85 | 5.49 | 26-69 | 271 | AE001720 | |
| | | YTVKKGDTLDAIAKRFFTTATFIKEAN QLKSY TIYAGQKLFIP | SEQ ID NO:86 | 9.73 | 76-118 | | | |
| | TM1686 | HVVKRGETLWSIANQYGVRVGDIVLIN RLEDDPRIVAGQVLKIG | SEQ ID NO:87 | 8.76 | 212-255 | 395 | AE001809 | |
| | dniR | HTIRSGDTLYALARRYGLGVDTLKAHN RAHSATHLKIGQKLIIP | SEQ ID NO:88 | 10.58 | 607-650 | 779 | AE001237 | membrane-bound lytic murein transglycosylase D |
| | | HVVQQGDTLWSLAKRYGVSVENLAEEN NLAVDATLSLGMILKTP | SEQ ID NO:89 | 4.81 | 734-777 | | | |
| Treponema pallidum | TP0155 | YEVREGDVVGRIAQRYDISQDAIISLN KLRSTRALQVGQLLKIP | SEQ ID NO:90 | 9.58 | 87-130 | 371 | AE001200 | |
| | TP0444 | HVIAKGETLFSLSRRYGVPLSALAQAN NLANVHQLVPGQRIVVP | SEQ ID NO:91 | 10.98 | 67-110 | 342 | AE001221 | |
| Borrelia burgdorferi | BB0262 | HKIKPGETLSHVAARYQITSETLISFN EIKDVRNIKPNSVIKVP | SEQ ID NO:92 | 9.72 | 183-226 (6) | 417 | AE001137 | Hypothetical protein |
| | | YIVKKNDSISSIASAYNVPKVDILDSN NLDNE VLFLGQKLFIP | SEQ ID NO:93 | 4.58 | 233-275 | | | |

TABLE 3-continued

AcmA cell wall binding domain homologs and their calculated pI values.
(the pI values are indicated directly behind the amino acid sequences)

| | | | | | | |
|---|---|---|---|---|---|---|
| | *BB0625 | YKVVKGDTLPSIAIKYKVKVSDLKRIN KLNVD NIKAGQIILIP | SEQ ID NO:94 | 10.02 | 44-86 (28) | 697 AE001164 | N-acetylmuramoyl-L-alanine amidase |
| | | YTAKEGDTIESISKLVGLSQEEIIAWN DLRSK DLKVGMKLVLT | SEQ ID NO:95 | 5.00 | 115-157 (7) | | |
| | | YMVRKGDSLSKLSQDFDISSKDILKFN FLNDD KLKIGQQLFLK | SEQ ID NO:96 | 9.20 | 165-207 (8) | | |
| | | HYVKRGETLGRIAYIYGVTAKDLVALN GNRAI NLKAGSLLNVL | SEQ ID NO:97 | 10.05 | 216-258 (27) | | |
| | | HSVAVGETLYSIARHYGVLIEDLKNWN NLSSN NIMHDQKLKIF | SEQ ID NO:98 | 7.41 | 286-328 | | |
| | BB0761 | YKVKKGDTFPKIANKINGMQSGIATIN LLDSP AVSVGQEILIP | SEQ ID NO:99 | 9.34 | 59-102 | 295 AE001176 | |
| Lactobacillus Øgle | *lys | YTVVSGDSWNKIAQRNGLSMYTLASQN GKSIYSTIYPGNKLIIK | SEQ ID NO:100 | 9.83 | 399-442 | 442 X90511 | lysin |
| Bacillus subtilis | *lytE | IKVKKGDTLWDLSRKYDTTISKIKSEN HLRSD IIVVGQTLSIN | SEQ ID NO:101 | 9.55 | 28-70 (17) | 334 U38819.1 | D-Glutamate-M-diaminopimelate endopeptidase |
| | | YKVKSGDSLWKISKKYGMTINELKKLN GLKSD LLRVGQVLKLK | SEQ ID NO:102 | 10.16 | 88-130 (20) | | |
| | | YKVKSGDSLSKIASKYGTTVSKLKSLN GLKSD VIVNQVLKVK | SEQ ID NO:103 | 10.03 | 151-193 | | |
| | spoVID | CIVQQEDTIERLCERYEITSQQLIRMN SLALDDELKAGQILYIP | SEQ ID NO:104 | 4.20 | 525-568 | 575 P37963 | stage VI sporulation protein D |
| | yaaH | MVKQGDTLSAIASQYRTTNDITETN EIPNPDSLVVGQTIVIP | SEQ ID NO:105 | 3.89 | 1-43 (5) | 427 P37531 | Hypothetical protein |
| | | YDVKRGDTLTSIARQFNTTAAELARVN RIQLNTVLQIGFRLYIP | SEQ ID NO:106 | 10.32 | 49-92 | | |
| | yhdD | IKVKSGDSLWKLAQTYNTSVAALTSAN HLSTT VLSIGQTLTIP | SEQ ID NO:107 | 9.56 | 29-71 (22) | 488 Y14079 | Hypothetical protein |
| | | YTVKSGDSLWLIANEFKMTVQELKKLN GLSSD LIRAGQKLKVS | SEQ ID NO:108 | 9.62 | 94-136 (39) | | |
| | | YKVQLGDSLWKIANKVNMSIAELKVLN NLKSD TIYVNQVLKTK | SEQ ID NO:109 | 9.72 | 176-218 (23) | | |

TABLE 3-continued

AcmA cell wall binding domain homologs and their calculated pI values.
(the pI values are indicated directly behind the amino acid sequences)

| | | | | | |
|---|---|---|---|---|---|
| | YTVKSGDSLWKIANNYNLTVQQIRNIN NLKSD VLVGQVLKLIT | SEQ ID NO:110 | 9.65 | 242-284 (24) | |
| | YTVKSGDSLWVIAQKFNVTAQQIREKN NLKTD VLGVGQKLVIS | SEQ ID NO:111 | 9.72 | 309-351 | |
| yojL | IKVKSGDSLWKLSRQYDTTISALKSEN KLKST VLVVGQSLKVP | SEQ ID NO:112 | 9.93 | 29-71 (18) | 414 Z99114 similar to cell wall binding protein |
| | YTVAYGDSLWMIAKNHKMSVSELKSLN SLSSD LIRPGQKLKIK | SEQ ID NO:113 | 9.81 | 90-132 (26) | |
| | YTVKLGDSLWKIANSLNMTVAELKTLN GLTSD TLYPKQVLKIG | SEQ ID NO:114 | 9.27 | 159-201 (25) | |
| | YKVKAGDSLWKIANRLGVTVQSIRDKN NLSSD VLQIGQVLTIS | SEQ ID NO:115 | 9.84 | 227-269 | |
| yocH | ITVQKGDTLWGISQKNGVNLKDLKEWN KLTSD KIIAGEKLTIS | SEQ ID NO:116 | 9.25 | 28-70 (9) | 287 AF027868 similar to papQ |
| | YTIKAGDTLSKIAQKFGTVNNLKVWN NLSSD MIYAGSTLSVK | SEQ ID NO:117 | 9.64 | 80-122 | |
| ykvP | HHVTPGETLSIIASKYNVSLQQLMELN HFKSD QIYAGQIIKIR | SEQ ID NO:118 | 8.65 | 345-387 | 399 Z99111 Hypothetical protein |
| *xlyB | YHVKKGDTLSGIAASHGASVKTLQSIN HITDPNHIKIGQVIKLP | SEQ ID NO:119 | 9.72 | 179-222 | 317 Z99110 N-acetylmuramoyl-L-alanine amidase |
| yrbA | HIVQKGDSLWKIAEKYGVDVEEVKKLN TQLSNPDLIMPGMKIKVP | SEQ ID NO:120 | 8.51 | 4-48 | 387 Z99118 similar to spore coat protein |
| ydhD | HIVGPGDSLFSIGRRYGASVDQIRGVN GLDET NIVPGQALLIP | SEQ ID NO:121 | 5.49 | 4-46 | 439 Z99107 |
| ykuD | YQVKQGDTLNSIAADFRISTAALLQAN PSLQA GLTAGQSIVIP | SEQ ID NO:122 | 6.10 | 4-46 | 164 Z99111 |
| *xlyA | YVVKKGDTLTSIARAFPGVTVAQLQEWN NIEDPNLIRVGQVLIVS | SEQ ID NO:123 | 4.65 | 161-204 | 297 P39800 N-acetylmuramoyl-L-alanine amidase |
| *orf15 | YKVKSGDNLTKIAKKHNTVATLLKLN PSIKDPNMIRVGQTINVT | SEQ ID NO:124 | 10.23 | 163-207 (6) | 258 P11187 |
| ØPBSX | | | | | |
| ØPZA | | | | | |
| (=0-29) | HKVKSGDTLSKIAVDNKTTVSRLMSLN PEITNPNHIKVGQTIRLS | SEQ ID NO:125 | 10.17 | 214-258 | P07540 |

TABLE 3-continued

AcmA cell wall binding domain homologs and their calculated pI values.
(the pI values are indicated directly behind the amino acid sequences)

| | | | | | | |
|---|---|---|---|---|---|---|
| ØB103 | *orf15 | HVVKKGDTLSEIAKKIKTSTKTLLELN PTIKNPNKIYVGQRINVG | SEQ ID NO:126 | 10.11 | 165-209 (9) | 263 X99260 | lysozyme |
| sphaericus | *Pep I | YKIKRGETLTGIAKKNKTTVSQLMKLN PNIKNANNIYAGQTIRLK | SEQ ID NO:127 | 10.61 | 219-263 | | |
| | | ILIRPGDSLWYFSDLFKIPLQLLLDSN RNINPQ LLQVGQRIQIP | SEQ ID NO:128 | 8.86 | 3-46 (6) | 396 X69507 | carboxypeptidase I |
| Salmonella dublin | nlpD | YTTQGDSLWQIAQNKNLPLNAILLVN PEIQPS RLHIGQTIQVP | SEQ ID NO:129 | 7.15 | 53-96 | | |
| | | YTVKKGDTLFYIAWITGNDFRDLAQRN SISAPYSLNVGQTLQVG | SEQ ID NO:130 | 8.64 | 121-164 | 377 AJ006131 | |
| Escherichia coli | *yebA | YVVSTGDTLSSILNQYGIDMGDISQLA AADKELRNLKIGQQLSWT | SEQ ID NO:131 | 4.13 | 77-121 | 419 p24204 | homologous to endopeptidase of Staphylococcus |
| | mltD | YTVRSGDTLSSIASRLGVSTKDLQQWN KLRGS KLKPGQSLTIG | SEQ ID NO:132 | 10.58 | 343-385 (16) | 452 P23931 | membrane-bound lytic murein transglycosylase d precursor |
| | | YRVRKGDSLSSIAKRHGVNIKDVMRWN SDTAN LQPGDKLTLF | SEQ ID NO:133 | 10.18 | 402-443 | | |
| | UUG | YTVKRGDTLYRISRTTGTSVKELARLN GISPPYTIEVGQKLKLG | SEQ ID NO:134 | 10.16 | 50-93 | 259 U28375 | Hypothetical protein |
| | nlpD | YTVKKGDTLFYIAWITGNDFRDLAQRN NIQAPYALNVGQTLQVG | SEQ ID NO:135 | 8.64 | 123-166 | 379 P33648 | Lipoprotein |
| Drosophila melanogaster | Q9VNA1 | YTVGNRDTLTSVAARFDTTPSELTHLN RLNSS FIYPGQQLIVP | SEQ ID NO:136 | 7.15 | 329-371 | 1325 AF125384 | Lethal 82FD protein |
| Drosophila melanogaster | Q961P8 | YTVGNRDTLTSVAARFDTTPSELTHLN RLNSS FIYPGQQLIVP | SEQ ID NO:136 | 7.15 | 104-146 | 678 AAK92873 | |
| Caenorhabditis elegans | F43G9.2 | RKVKNGDTLNKLAIKYQVNVAEIKRVN NMVSEQDFMALSKVKIP | SEQ ID NO:137 | 10.01 | 12-55 | 179 Z79755 | |
| Caenorhabditis elegans | F52E1.13 | YTITETDTLERVAASHDCTVGELMKLN KMASR MVFPGQKILVP | SEQ ID NO:138 | 7.08 | 24-66 | 819 U41109 | |
| Caenorhabditis elegans | F07G11.9 | TEIKSGDSCWNIASNAKISVERLQQLN KGMKCDKLPLGDKLCLA | SEQ ID NO:139 | 8.32 | 23-66 (11) | 1614 U64836/ AF016419 | Putative Endochitinase |

TABLE 3-continued

AcmA cell wall binding domain homologs and their calculated pI values.
(the pI values are indicated directly behind the amino acid sequences)

| | | | | | |
|---|---|---|---|---|---|
| | | LKLKAEDTCFKIWSQKLSERQFLGMNEGMDCDKLKVGKEVCVA | SEQ ID NO:140 | 7.84 | 78-121 (21) |
| | | HKIQKGDTCFKIWTTNKISEKQFRNLNKGLDCDKLEIGKEVCIS | SEQ ID NO:141 | 8.65 | 143-186 (21) |
| | | LKIKEGDTCYNIWTSQKISEQEFMELNKGLDCDKLEIGKEVCVT | SEQ ID NO:142 | 4.54 | 208-251 (19) |
| | | YRFKKGDTCYKIWTSHKMSEKQFRALNRGIDCDRLVPGKELCVG | SEQ ID NO:143 | 9.35 | 271-314 (20) |
| | | ITVKPGDTCFSIWTSQKMTQQQFMDINPELDCDKLEIGKEVCVT | SEQ ID NO:144 | 4.21 | 335-378 (23) |
| | | VKINPGDTCFNIWTSQRMTQQQFMDLNKRLDCDKLEVGKEVCVA | SEQ ID NO:145 | 6.30 | 402-445 (21) |
| | | VQINPGDTCFKIWSAQKLTEQQFMELNKGLDCDRLEVGKEVCIA | SEQ ID NO:146 | 4.60 | 467-510 (37) |
| | | TEVKEGDTCFKIWSAHKITEQQFNEMNRGLDCNRLEVGKEVCIV | SEQ ID NO:147 | 5.12 | 548-591 (44) |
| | | IKVKEGDTCFKIWSAQKMTEQQFMEMNRGLDCNKLMVGKEVCVS | SEQ ID NO:148 | 7.85 | 636-679 (66) |
| | | ATITPGNTCFNISVAYGINLT DLQKTYDCKALEVGDTICVS | SEQ ID NO:149 | 3.99 | 746-786 (8) |
| | | IEVIKGDTCWFLENAFKTNQTEMERANEGVKCDNLPIGRMMCVW | SEQ ID NO:150 | 4.67 | 795-838 |
| Caenorhabditis elegans | T01C4.1 | HTIKSGDTCWKIASEASISVQELEGLNSKKSCANLAVGLSEQEF | SEQ ID NO:151 | 5.01 | 23-66 (51) | 1484 U70858 | Putative Endochitinase |
| | | IHVKEGDTCYTIWTSQHLTEKQFMDMNEELNCGMLEIGNEVCVD | SEQ ID NO:152 | 4.12 | 118-161 (25) |
| | | ATVTPGSSCYTISASYGLNLAELQTTYNCDALQVDDTICVS | SEQ ID NO:153 | 3.07 | 187-226 (9) |
| | | IEILNGDTCGFLENAFQTNNTEMEIANEGVKCDNLPIGRNNCVW | SEQ ID NO:154 | 3.85 | 236-279 |
| Bacilius subtilis | # ypbE | HTVQKKETLYRISMKYYKSRTGEEKIRAYNHLNGNDVYTGQVLDIP | SEQ ID NO:155 | 9.45 | 191-136 | 240 L47648 |

TABLE 3-continued

AcmA cell wall binding domain homologs and their calculated pI values.
(the pI values are indicated directly behind the amino acid sequences)

| Organism | Gene | Sequence | SEQ ID NO | pI | Range | aa | Accession | Notes |
|---|---|---|---|---|---|---|---|---|
| Citrobacter fruendii | # eae | YTLKTGESVAQLSKSQGISVPVIWSLN KHLYSSESEMMKASPGQQIILP | SEQ ID NO:156 | 8.59 | 65-113 | 936 | Q07591 | |
| Escherichia coli | # eae | YTLKTGETVADLSKSQDINLSTIWSLN KHLYSSESEMMKAAPGQQIILP | SEQ ID NO:157 | 5.65 | 65-113 | 934 | P43261 | Necessary for close (intimate) attachment of bacteria |
| Micrococcus luteus | # rpf | IVVKSGDSLWTLANEYEVEGGWTAIYE ANKGAVSDAAVIYVGQELVL | SEQ ID NO:158 | 3.85 | 171-218 | 220 | Z96935 | Bacterial Cytokine |
| Bacillus subtilis | # yneA | IEVQQGDTLWSIADQVADTKKINKNDF IEWVADKNQLQTSDIQPGDELVIP | SEQ ID NO:159 | 3.81 | 40-90 | 105 | Z73234 | |
| Streptococcus pyogenes | # | YTVKYGDTLSTIAEAMGIDVHVLGDIN HIANIDLIFPDTILTANYNQHG QATTLT | SEQ ID NO:160 | 4.23 | 47-103 | 393 | U09352 | |
| Bacillus subtilis | # xkdP | YTVKKGDTLWDIAGRFYGNSTQWRKIW NANKTAMIKRSKRNIRQPGHWIFPGQK LKIP | SEQ ID NO:161 | 11.23 | 176-234 | 235 | P54335 | |
| Bacillus subtilis | # yqbP | YTVKKGDTLWDIAGRFYGNSTQWRKIW NANKTAMIKRSKRNIRQPGHWIFPGQK LKIP | SEQ ID NO:161 | 11.23 | 177-234 | 235 | G1225954 | |
| Bacillus subtilis | # | YTVKKGDTLWDLAGKFYGDSTKWRKIW KVNKKAMIKRSKRNIRQPGHWIFPGQK LKIP | SEQ ID NO:162 | 10.75 | 161-218 | 219 | P45932 | | a) Proteins listed were obtained by a homology search in the SWISSPROT, PIR, and Genbank databases with the repeats of AcmA using the BLAST program.
b) *genes encoding cell wall hydrolases.
  # proteins containing repeats that are longer than the consensus sequence.
c) The number of aa residues between the repeats is given between brackets.
d) Number of aa of the primary translation product.
e) Genbank accession number.

Consensus repeat YxVKxGDTLxxIAxxxxxxxxLxxxNxxLxxxxxIxxGQxIxVx (SEQ ID NO:163)
                   H IR  ESV LS         I    I     L  L I
                   L  I   V                     v    V L

TABLE 4

Calculated pI's of individual repeat sequences of the AcmA and AcmD protein anchors.

| AcmA anchor domain | | AcmD anchor domain | |
|---|---|---|---|
| Repeat | Calculated pI | Repeat | Calculated pI |
| A1 | 9.75 | D1 | 4.15 |
| A2 | 9.81 | D2 | 3.78 |
| A3 | 10.02 | D3 | 4.15 |
| A1A2A3 | 10.03 | D1D2D3 | 3.85 |

TABLE 5

Hybrid protein anchors composed of different AcmA and AcmD repeat sequences and their calculated pI's.

| Composition of hybrids | | |
|---|---|---|
| AcmA-repeat sequence | AcmD-repeat sequence | Calculated pI |
| A1A2A3 | — | 10.03 |
| A1A2 | D1 | 9.53 |
| A1A2A3 | D1D2D3 | 8.66 |
| A1 | D2 | 8.45 |
| A3 | D1D2 | 7.39 |
| A1A2 | D1D2D3 | 6.08 |
| A3 | D1D2D3 | 5.07 |
| A1 | D1D2D3 | 4.37 |
| — | D1D2D3 | 3.85 |

REFERENCES

Bolotin et al. (2001) *Genome Res.* 11: 731-753.
Buist et al. (1995) *J. Bacteriol.* 177: 1554-1563.
Gasson (1983) *J. Bacteriol.* 154: 1-9.
Kok et al. (1988) *Appl. Environ. Microbiol.* 54: 231-238.
Kuipers et al. (1997) *Tibtech.* 15: 135-140.
Morata de Ambrosini et al. (1998) *J. Food Prot.* 61: 557-562.
Navarre and Schneewind (1994) *Mol. Microbiol.* 14: 115-121.
Norton et al. (1994) *FEMS Microbiol. Lett.* 120: 249-256.
Norton et al. (1996) *FEMS Immunol. Med. Microbiol.* 14: 167-177.
Poquet et al. (2000) *Mol. Microbiol.* 35: 1042-1051.
Ramasamy (1987) *Immunol. Cell Biol.* 65: 419-424.
Ramasamy et al. (1999) *Parasite Immunol.* 21: 397-407.
Robinson et al. (1997) *Nature Biotechnol.* 15: 653-657.
Sauvé et al. (1995) *Anal. Biochem.* 226: 382-283.

What is claimed is:

1. A method for immunizing a subject, said method comprising:
   administering a vaccine to a mucosal membrane of the subject, said vaccine comprising:
   a proteinaceous substance comprising an immunogenic determinant attached to cell wall material from a Gram positive bacterium, wherein said cell wall material consists essentially of spherical peptidoglycan microparticles, the microparticles being obtainable by treating a cell wall with an acid solution, thus removing a cell wall component selected from the group consisting of a protein, lipotechoic, a carbohydrate, and combinations thereof from said cell wall material;
   so as to immunize the subject.

2. The method according to claim 1, wherein said proteinaceous substance comprises an immunogenic determinant fused to an N-acetyl muramidase cell wall binding domain, homolog or a functional derivative thereof that binds to the treated cell wall material.

3. The method according to claim 1, wherein said Gram positive bacterium is selected from the group consisting of a *Lactococcus*, a *Lactobacillus*, a *Bacillus* and a *Mycobacterium* spp.

4. The method according to claim 2, wherein said immunogenic determinant is of a pathogen origin.

5. The method according to claim 4, wherein said pathogen is *Plasmodium falciparum*.

6. The method according to claim 5, wherein said immunogenic determinant is a malaria antigen merozoite membrane surface antigen 2.

7. The method according to claim 4, wherein said pathogen is *Streptococcus pneumoniae*.

8. The method according to claim 7, wherein said immunogenic determinant is a Streptococcal putative proteinase maturation protein A antigen.

9. A method for immunizing a subject, said method comprising:
   administering a vaccine to a mucosal membrane of the subject, said vaccine comprising:
   cell wall material from a Gram positive bacterium which has not been mechanically disrupted, wherein said cell wall material consists essentially of spherical peptidoglycan microparticles reflecting the size and shape of the Gram positive bacterium, the microparticles being obtainable by treating the cell wall material with an acid solution, thus removing a cell wall component selected from the group consisting of a protein, lipoteichoic acid, a carbohydrate, and combinations thereof from said cell wall material;
   a heterologous polypeptide comprising an immunogenic determinant; and
   means for attaching the heterologous polypeptide to the peptidoglycan microparticle;
   so as to immunize the subject.

10. The method according to claim 9, wherein the means for attaching the heterologous polypeptide to the peptidoglycan microparticle comprises an N-acetyl muramidase cell wall binding domain.

11. The method according to claim 1, wherein the proteinaceous substance is attached to said cell wall material using a method comprising:
    treating said cell wall material with an acid solution, thus removing a cell wall component selected from the group consisting of a protein, a lipoteichoic acid, a carbohydrate, and combinations thereof from said cell wall material;
    thus producing spherical peptidoglycan microparticles; and
    contacting said spherical peptidoglycan microparticles with a proteinaceous substance, thus binding said proteinaceous substance to said spherical peptidoglycan microparticles.

12. The method according to claim 11, wherein said acid solution comprises an acid selected from the group consisting of acetic acid, hydrochloric acid, sulphuric acid, trichloroacetic acid, trifluoroacetic acid, monochloro acetic acid, and mixtures of any thereof.

13. The method according to claim 1, wherein said acid solution comprises an acid selected from the group consisting of acetic acid, hydrochloric acid, sulphuric acid, trichioroacetic acid, trifluoroacetic acid, monochloric acetic acid, and mixtures of any thereof.

14. A method for immunizing a subject against a pathogen, the method comprising:
    administering a vaccine associated with the pathogen, to a mucosal membrane of the subject, the vaccine comprising:
    a proteinaceous substance comprising an immunogenic determinant associated with the pathogen attached to cell wall material from a Gram positive bacterium, wherein the cell wall material consists essentially of spherical peptidoglycan microparticles produced by treating the cell wall material with an acid solution, thus removing a cell wall component selected from the group consisting of a protein, lipotechoic, a carbohydrate, and combinations thereof from the cell wall material;
    so as to immunize the subject against the pathogen.

* * * * *